United States Patent
Barnscheid et al.

(10) Patent No.: US 9,737,490 B2
(45) Date of Patent: Aug. 22, 2017

(54) TAMPER RESISTANT DOSAGE FORM WITH BIMODAL RELEASE PROFILE

(71) Applicant: GRÜNENTHAL GMBH, Aachen (DE)

(72) Inventors: Lutz Barnscheid, Mönchengladbach (DE); Anja Geißler, Stolberg (DE); Klaus Wening, Köln (DE); Stefanie Strauch, Aachen (DE); Jana Pätz, Bornheim (DE); Sebastian Schwier, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/287,348

(22) Filed: May 27, 2014

(65) Prior Publication Data
US 2014/0356428 A1    Dec. 4, 2014

(30) Foreign Application Priority Data
May 29, 2013    (EP) .................................... 13169658

(51) Int. Cl.
| | |
|---|---|
| A61K 9/22 | (2006.01) |
| A61K 9/20 | (2006.01) |
| A61K 31/485 | (2006.01) |
| A61K 31/167 | (2006.01) |
| A61K 45/06 | (2006.01) |
| A61K 9/24 | (2006.01) |

(52) U.S. Cl.
CPC ............ *A61K 9/2086* (2013.01); *A61K 9/209* (2013.01); *A61K 9/2031* (2013.01); *A61K 9/2095* (2013.01); *A61K 31/167* (2013.01); *A61K 31/485* (2013.01); *A61K 45/06* (2013.01)

(58) Field of Classification Search
CPC ...... A61K 9/20; A61K 9/2004; A61K 9/2027; A61K 9/2031; A61K 9/2072; A61K 9/2086; A61K 9/209; A61K 9/2095
USPC ................................................ 424/465-489
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Moorman-Li, R. et al, "A Review of Abuse-Deterrent Opioids for Chronic Nonmalignant Pain." Pharmacy and Therapeutics, vol. 37 No. 7, Jul. 2012, pp. 412-421.

(Continued)

*Primary Examiner* — Micah-Paul Young
(74) *Attorney, Agent, or Firm* — Norris McLaughlin & Marcus, P.A.

(57) ABSTRACT

The invention relates to a pharmaceutical dosage form comprising
(i) at least one formed segment ($S_1$), which contains a first pharmacologically active ingredient ($A_1$) and provides prolonged release thereof, and
(ii) at least one further segment ($S_2$), which contains a second pharmacologically active ingredient ($A_2$) and provides immediate release thereof,
wherein the at least one formed segment ($S_1$) exhibits a higher breaking strength than the at least one further segment ($S_2$) and the at least one formed segment ($S_1$) exhibits a breaking strength of more than 500 N.

16 Claims, 14 Drawing Sheets

(56) References Cited

U.S. PATENT DOCUMENTS

| | | |
|---|---|---|
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Mari et al. |
| 8,858,963 B1 | 10/2014 | Devarakonda et al. |
| 9,192,578 B2 | 11/2015 | McGinity et al. |
| 2001/0038852 A1 | 11/2001 | Kolter et al. |

(56) References Cited

U.S. PATENT DOCUMENTS

| | | |
|---|---|---|
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1* | 5/2003 | Kao .............. A61K 9/209 514/282 |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0192333 A1 | 9/2005 | Hinze et al. |
| 2005/0214223 A1 | 9/2005 | Bartholomaeus et al. |
| 2005/0220877 A1* | 10/2005 | Patel .............. A61K 9/209 424/472 |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1* | 8/2006 | Ashworth .............. A61K 9/2031 424/469 |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 4/2008 | Wada et al. |
| 2008/0085304 A1 | 4/2008 | Baichwal et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Cailly-Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |

(56) References Cited

U.S. PATENT DOCUMENTS

| | | |
|---|---|---|
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0159100 A1 | 6/2011 | Anderson et al. |
| 2011/0187017 A1 | 8/2011 | Haupts |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Gei Ler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 82 | 8/2006 |
| AU | 2006210145 A1 | 8/2006 |
| AU | 2009207796 A1 | 7/2009 |
| AU | 2009243681 A1 | 11/2009 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2317747 A1 | 7/1999 |
| CA | 2343234 A1 | 3/2000 |
| CA | 2352874 A1 | 6/2000 |
| CA | 2414349 | 1/2002 |
| CA | 2456322 A1 | 2/2003 |
| CA | 2502965 A1 | 5/2004 |
| CA | 2503155 | 5/2004 |
| CA | 2534925 A1 | 2/2005 |
| CA | 2534932 A1 | 2/2005 |
| CA | 2489855 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 1663513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101022787 A | 1/2008 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 2/2010 |

(56) References Cited

FOREIGN PATENT DOCUMENTS

| | | |
|---|---|---|
| DE | 10361596 A1 | 9/1929 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 10336400 A1 | 3/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 2/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0780369 A1 | 6/1997 |
| EP | 0785775 A1 | 7/1997 |
| EP | 0761211 A1 | 12/1997 |
| EP | 0809488 A1 | 12/1997 |
| EP | 0820698 A1 | 1/1998 |
| EP | 0820753 A2 | 1/1998 |
| EP | 0857062 A2 | 6/1998 |
| EP | 0864324 A1 | 9/1998 |
| EP | 0864326 A2 | 9/1998 |
| EP | 0598606 B1 | 6/1999 |
| EP | 0075710 B1 | 8/1999 |
| EP | 0980894 A1 | 2/2000 |
| EP | 0988106 A1 | 3/2000 |
| EP | 1014941 A1 | 7/2000 |
| EP | 070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 131 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 10/2005 |
| EP | 1611880 A2 | 1/2006 |
| EP | 1658054 51 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |

(56) References Cited

FOREIGN PATENT DOCUMENTS

| | | |
|---|---|---|
| JP | 03-501737 A | 4/1991 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 213 244 C1 | 6/1999 |
| RU | 2198197 C2 | 2/2003 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | I254634 B | 5/2006 |
| WO | WO 80/00841 A1 | 5/1980 |
| WO | WO 89/05624 A1 | 6/1989 |
| WO | WO 90/03776 A1 | 4/1990 |
| WO | WO 93/06723 A1 | 4/1993 |
| WO | WO 93/10758 A1 | 6/1993 |
| WO | WO 93/10765 A1 | 6/1993 |
| WO | WO 93/11749 A1 | 6/1993 |
| WO | WO 93/23017 A1 | 11/1993 |
| WO | WO 94/06414 A1 | 3/1994 |
| WO | WO 94/08567 A1 | 4/1994 |
| WO | WO 95/17174 A1 | 6/1995 |
| WO | WO 95/20947 A1 | 8/1995 |
| WO | WO 95/22319 A1 | 8/1995 |
| WO | WO 95/30422 A1 | 11/1995 |
| WO | WO 96/00066 A1 | 1/1996 |
| WO | WO 96/03979 A1 | 2/1996 |
| WO | WO 96/14058 A1 | 5/1996 |
| WO | WO 97/00673 A1 | 1/1997 |
| WO | WO 97/33566 A2 | 9/1997 |
| WO | WO 97/49384 A1 | 12/1997 |
| WO | WO 98/20073 A2 | 5/1998 |
| WO | WO 98/28698 A1 | 7/1998 |
| WO | WO 98/35655 A2 | 8/1998 |
| WO | WO 98/51758 A1 | 11/1998 |
| WO | WO 98/35655 A3 | 12/1998 |
| WO | WO 99/12864 A1 | 3/1999 |
| WO | WO 99/32120 A1 | 7/1999 |
| WO | WO 99/44591 A1 | 9/1999 |
| WO | WO99/45887 A2 | 9/1999 |
| WO | WO 99/48481 A1 | 9/1999 |
| WO | WO 00/13647 A1 | 3/2000 |
| WO | WO 00/33835 A1 | 6/2000 |
| WO | WO 00/40205 A2 | 7/2000 |
| WO | WO 01/08661 A2 | 2/2001 |
| WO | WO 01/12230 A1 | 2/2001 |
| WO | WO 01/15667 A1 | 3/2001 |
| WO | WO 01/52651 A2 | 7/2001 |
| WO | WO 01/58451 | 8/2001 |
| WO | WO 01/97783 A1 | 12/2001 |
| WO | WO 02/26061 A1 | 4/2002 |
| WO | WO 02/26262 A2 | 4/2002 |
| WO | WO 02/26928 A1 | 4/2002 |
| WO | WO 02/35991 A2 | 5/2002 |
| WO | WO 02/071860 A1 | 9/2002 |
| WO | WO 02/088217 A1 | 11/2002 |
| WO | WO 02/094254 A2 | 11/2002 |
| WO | WO 03/006723 A1 | 1/2003 |
| WO | WO 03/013433 A2 | 2/2003 |
| WO | WO 03/013476 A1 | 2/2003 |
| WO | WO 03/013479 A1 | 2/2003 |
| WO | WO 03/013538 | 2/2003 |
| WO | WO 03/015531 A2 | 2/2003 |
| WO | WO 03/018015 A1 | 3/2003 |
| WO | WO 03/024426 A1 | 3/2003 |
| WO | WO 03/024430 A1 | 3/2003 |
| WO | WO 03/026624 A1 | 4/2003 |
| WO | WO 03/026743 A2 | 4/2003 |
| WO | WO 03/028698 A1 | 4/2003 |
| WO | WO 03/028990 A1 | 4/2003 |
| WO | WO 03/031546 A1 | 4/2003 |
| WO | WO 03/035029 A1 | 5/2003 |
| WO | WO 03/035053 A1 | 5/2003 |
| WO | WO 03/035054 A1 | 5/2003 |
| WO | WO 03/035177 A2 | 5/2003 |
| WO | WO 03/039561 A1 | 5/2003 |
| WO | WO 03/049689 A2 | 6/2003 |
| WO | WO 03/053417 A2 | 7/2003 |
| WO | WO 03/068392 A1 | 8/2003 |
| WO | WO 03/070191 A1 | 8/2003 |
| WO | WO 03/092648 A1 | 11/2003 |
| WO | WO 03/094812 A1 | 11/2003 |
| WO | WO 03/105808 A1 | 12/2003 |
| WO | WO 2004/004693 A1 | 1/2004 |
| WO | WO 2004/093801 A2 | 1/2004 |
| WO | WO 2004/100894 A2 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093819 A1 | 11/2004 |
| WO | WO 2004/098567 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |

(56) References Cited

FOREIGN PATENT DOCUMENTS

| | | |
|---|---|---|
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/058249 A2 | 1/2006 |
| WO | WO 2006/002884 B1 | 3/2006 |
| WO | WO 2006/039692 A2 | 4/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/005716 A2 | 11/2007 |
| WO | WO 2007/131357 A1 | 11/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/005803 A1 | 11/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Eudragit NE40D web page from Evonik website; downloaded Feb. 24, 2015.
Eudragit RS PO web page from Evonik website; downloaded Feb. 24, 2015.
Glyceryl behenate monograph; European Pharmacopeia 5.0; dated Jan. 2005; downloaded Feb. 24, 2015.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
Bruce et al, Properties of hot-melt extuded tablet formulations for the colonic delivery of 5-aminosalicylic acid, European Journal of Pharmaceutics and Biopharmaceutics, 59 (2005) 85-97.
Bingwen et al, 2008, p. 367.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
Bingwen et al, 2008, p. 367. (full translation attached).
Extended European Search Report and Opinion for Application No. EP 15153679.4-1455, dated Jun. 30, 2015.
West, Anthony R., Solid state chemistry and its applications, Wiley, New York, 1988, pp. 358 and 365.
Monolithic: retrieved from internet: http:/merriam-webster.com/dictionary/monolithic. Retrieved on Sep. 2, 2015.
European Search Report and Written Opinion for EP Application No. 14169801.9-1455 Oct. 20, 2014.
European Search Report and Written Opinion for EP Application No. 14176277.3-1460, Dec. 15, 2014.
Dierickx et al., "Co-extrusion as manufacturing technique for fixed-dose combination mini-matrices," European Journal of Pharmaceutics and Biopharmaceutics 81 (2012), 683-689.
Oliveira et al., "Production and characterization of laminar coextrudates at room temperature in the absence of solvents," AAPS Annual Meeting and Exposition, Oct. 14-18, 2012, Chicago, USA.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013), pp. 1250-1258.
Salomies et al., "Determination of Oxycodone Hydrochloride in Oral Solutions by High-Performance Thin-Layer Chromatography/Densitometry," Journal of AOAC International, 83: 1497-1501 (2000).

(56) References Cited

OTHER PUBLICATIONS

Eggleston, The seat of the emetic action of various drugs: J. Pharmacol. Exp. Ther. 7, 225-253 (1915).
Evonik Rohm GmbH product brochure: EUDRAGIT acrylic polymers for solid oral dosage forms (2009).
Morissette et al. Adv. Drug. Del. Rev. 26 (2004), 275-300.
Vippagunta et al. Adv. Del. Rev. (2001), 3-26.
PCT International Search Report and Written Opinion for PCT Application No. PCT/EP2014/064830 dated Aug. 6, 2014.
Lenindzer, A., "The molecular basis of the structure and functions of cells" Moscow 1974, p. 68.
Kondrat, T., "Technology dosage forms" Moscow 1991, p. 96.
2.9 Methoden der pharmazeutischen Technologie, European Pharmacopeia, 143-144, 1997. (Full English translation attached).
Albertini, B. "New spray congealing atomizer for the microencapsulation of highly concentrated solid and liquid substances" European Journal of Pharmaceutics and Biopharmaceutics 69 (2008) 348-357.
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90, 1993.
Application of a modelling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., "Catalytic Hydrogenation of a, B-Unsaturated Ketones. III The Effect of Quantity and Type of Catalysts," J.Org Chem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al., "The impact of the addition of naloxone on the use and abuse of pentazocine", Public Health Reports, Jul.-Aug. 1987, vol. 102, No. 4, p. 426-429.
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-metl extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Disanto, Anthony. Bioavailability and Bioequivalency Testing, Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003. pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
El-Egakey, Adel et al, "Hot extruded dosage forms Part I Technology and dissolution kinetics of polymeric matrices" Pharmacerutica Acta Helvetiae vol. 46, pp. 31-53,Mar. 19, 1970.
El-Sherbiny I.M. et at "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents Only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.

(56) References Cited

OTHER PUBLICATIONS

Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83, pp. 1487-1491 in Remington's Pharmaceutical Sciences, 17th Ed, 1985.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1-1219, Sep. 24, 2012.
European Search Report and Opinion, Application No. 11006253.6-2112, Dec. 16, 2011.
European Search Report and Opinion, Application No. 11006254.4-2112, Dec. 16, 2011.
European Search Report and Opinion, Application No. 11008131.2-1219, Feb. 24, 2012.
European Search Report and Opinion, Application No. 11009129.5-2112, Apr. 10, 2012.
European Search Report and Opinion, Application No. 12001296.8-1219, Jun. 26, 2012.
European Search Report and Opinion, Application No. 12001301.6-1219, Jun. 26, 2012.
European Search Report and Opinion, Application No. 12003743.7-1219, Sep. 24, 2012.
European Search Report and Written Opinion for EP Application No. 13169658.5, Aug. 6, 2013.
European Search Report and Written Opinion for EP Application No. 13169659.3, Aug. 6, 2013.
European Search Report and Written Opinion for EP Application No. 13176309.9-1460, Oct. 9, 2013.
European Search Report and Written Opinion for EP Application No. 13197503.9-1460, Feb. 18, 2014.
European Search Report and Written Opinion for EP Application No. 13425151.1-1460, Mar. 11, 2014.
Evaluation of Verapamil HCl (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 in Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1) pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull, 1992, 40(10), 2800-2804.
King et al. Oral Solid Dosage Forms. Chapter 90. pp. 163-1632 in Remington's Pharmaceutical Sciences, 17th Ed, 1985.
King, R, "Tablets, Capsules, and Pills" Remington's Pharmaceutical Sciences, pp. 1553-1593. Ch. 89, 1980, 16$^{th}$ Edition.

(56) References Cited

OTHER PUBLICATIONS

King, Remington's Pharmaceutical Sciences 17th ed., Chapter 78, p. 1418 (1985).
Knevel, Adelbert. Separation. Chapter 78. pp. 1432-1442 in Remington's Pharmaceutical Sciences, 17th Ed, 1985.
Kolter, K., "Compression Behaviour of Kollidon SR," APV/ APGI 2002, Florence, Apr. 11, 2002.
Lee, Y.-S. et al., Principles of Terahertz Science and Technology (Lecture Notes in Physics), Springer; 1 edition 2008. (Table of Contents Only).
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990, vol. 2 (Cover and Table of Content only).
Lintner, Carl. Stability of Pharmaceutical Products. Chapter 82. pp. 1478-1486 in Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 in Remington's Pharmaceutical Sciences, 17th Ed, 1985.
Madorsky S.L., "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990, English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 750 mg Extended Release Tablets, Lubrizol Advanced Materials, Inc., Sep. 2010.
Metformin Hydrochloride1000 mg Extended Release Tablets, Lubrizol Advanced Materials, Inc., Nov. 20, 2009, Previous Edition Dec. 19, 2008.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp, 3511-3515, 1987.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinyipolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.

(56) References Cited

OTHER PUBLICATIONS

Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Oct. 1991, 8(10), S-192.
Pharm. Research, Official Journal of the American Association of Pharmaceutical Scientists, Sep. 1989, 6(9), S-98.
Phillips, G. Briggs. Sterilization. Chapter 79, pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
POLYOX water-soluble resins (DOW Mar. 2002); see http://msds-search.dow.com/PublishedLiteratureDOWCOM/dh_0031/0901b80380031a4a.pdf?file path=/326-00001.pdf &fromPage=GetDoc).
POLYOX WSR-303, retrieved Mar. 10, 2014 from URL http://www.dow.com/dowwolff/en/industrial_solutions/polymers/polyethylene.
POLYOX, COLORCON, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S, Coating of Pharmaceutical Dosage Forms, Chapter 91. pp. 1633-1643 in Remington's Pharmaceutical Sciences, 17th Ed, 1985.
Prapaitrakul W. et al. "Release of Chlorpheniramine Maleate from Fatty Acid Ester Matrix Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.
Radko S.etal., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10).1043, (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Sax et al., Hawley's Condensed Chemical Dictionary, 11th ed., 1987, p. 1233, definition of "wax".
Scheirs J., et al. "Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCl From Melt extruded Polyethylene Disks", Pharmaceutical Research, Oct. 1991, vol. 8, No. 10, p. S-192.
Siegel, P. Tonicity, Osmoticity, Osmolality, and Osmolarity. Chapter 80. pp. 1454-1472 In Remington's Pharmaceutical Sciences, 17th Ed, 1985.
Silver, J. Painkiller OxyContin "most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.

(56) References Cited

OTHER PUBLICATIONS

Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U. "Derivatives of Morphine. I 14-Dihydroxydihydromorphinone," J. Am. Chem. Soc. 77, pp. 5891-5892, Nov. 20, 1955.
Wikipedia—Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N. et al. Mathematical modeling and in vitro study of controlled drug release via a highly swellable and dissoluble polymer matrix: polyethylene oxide with high molecular weights, J Control Release, Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar- and -pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1):35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Extended European Search Report and Opinion for Application No. EP 15165064.5-1455, Oct. 16, 2015.
Extended European Search Report and Opinion for Application No. EP 15165065.2-1455, Nov. 2, 2015.
Extended European Search Report and Opinion for Application No. EP 15165067.8-1455, Nov. 2, 2015.
Extended European Search Report and Opinion for Application No. EP 15165069.4-1455, Nov. 2, 2015.
Extended European Search Report and Opinion for Application No. EP 15165070.2-1455, Nov. 2, 2015.
Chibuzor et al. "Formulation Development and Evaluation of Drug Release Kinetics from Colon-Targeted Ibuprofen Tablets Based on Eudragit RL 100-Chitosan interpolyelectrolyte Complexes," Hindawi Publ. Corporation ISRN Pharmaceutics, vol. 2013, Article ID 838403.
Cuesov, 1999, pp. 351-352.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sidhu et al., "Watch for nonpsychotropics causing psychiatric side effects," Current Psychiatry, vol. 7, No. 4, 2008, 61-74.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al, "Xanthan gum to tailor drug release of sustained-release ethylcellulose mini-matrices prepared via hotmelt extrusion: in vitro and in vivo evaluation," European Journal of Pharmaceutics and Biopharmaceutics. 63 (2006) 320-330.
Vynckier et al., "Hot-melt co-extrusion for the production of fixed-dose combination products with a controlled release ethylcellulose matrix core," International Journal of Pharmaceutics 464 (2014), 65-74.
The Merck Index, 14th Ed. (2006) No. 0006360 Nalefene.
The Merck Index, 14th Ed. (2006) No. 0006362 Naloxone.

(56) References Cited

OTHER PUBLICATIONS

The Merck Index, 14th Ed. (2006) No. 0006363 Naltrexone.
The Merck Index, 14th Ed. (2006) No. 0006959 Oxycodone.
Borquist et al., "Simulation of the release from a multiparticulate system validated by single pellet and dose release experiements," J. Controlled Release, 97: 453-465 (2004).
Saleem et al. "Formulation and Evaluation of Tramadol hydrochloride Rectal Suppositories," Indian J. Pharm Sci. Sep.-Oct. 2008; 70(5), 640-644.
Alekseeva et al, Chemical-Pharmaceutical Yournal, vol. 41, No. 9, 2007, 49-52.
Extended European Search Report and Opinion for Application No. EP 15184634.2-1455, Mar. 3, 2016.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Koziolek, M. et al., "Development of a bio-relevant dissolution test device simulating mechanical aspects present in the fed stomach," European Journal of Pharmaceutical Sciences 57 (2014) 250-256.
Remington, Chapter 45, pp. 996-1035. (Full Translation Attached).
Decision of the United States District Court for the Southern District of New York, in In re *Endo Pharmaceuticals Inc. and Grünenthal GmbH* v. *Anneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in in re *Oxycontin Antitrust Litigation, Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29*th* Annual Meeting of the Controlled Release Society, in collaboration with the Korea Society for Biomaterials, Minneapolis, 1*st* Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.

Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of The University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
CROWLEY0000001- CROWLEY0000127.
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts at Intranasal Abuse of Concerta," Letters to the Editor, J. Am. Acad. Child Adolesc. Psychiatry, 41:1 (Jan. 2002).
Jannsen Pharmaceuticals, Inc. CONCERTA Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2.13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).

(56) References Cited

OTHER PUBLICATIONS

Kidokoro, M. et al. , "Properties of Tablets Containing Granulations of Ibuprofen and Acrylic Copolymers Prepared by Thermal Processes," Pharm Dev. and Tech. , 6:263-275 (2001).
Kinjo, N, et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int 'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms"in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N. et al. "The effect of temperature on the tensile strength and disintegration of paracetamol and oxytetracylcine tablets," J Pharm Pharmac., 29:389-392 (1977).
POLYOX Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version 16—Sep. 2010; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties," Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Alekseeva et al, Chemical-Pharmaceutical Journal, vol. 41, No. 9, 2007, 49-52. (Full translation attached.).
Efentakis et al, Effects of Excipients on Swelling and Drug Release from Compressed Matrices, in Drug Development and Industrial Pharmacy 23(1):107-112, Jan. 1997, Abstract.
Extended European Search Report for Application No. EP 16183922.0-1460, Oct. 31, 2016.
Fathima, N. et al. "Drug-excipient interaction and its importance in dosage form development," Journal of Applied Pharmaceutical Science 01 (06); 2011, pp. 66-71.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035.
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.

* cited by examiner

TAMPER RESISTANT DOSAGE FORM WITH BIMODAL RELEASE PROFILE

This application claims priority of European Patent Application No. 13 169 658.5, filed on May 29, 2013, the entire contents of which are incorporated herein by reference.

FIELD OF THE INVENTION

The invention relates to a pharmaceutical dosage form comprising
(i) at least one formed segment ($S_1$), which contains a first pharmacologically active ingredient ($A_1$) and provides prolonged release thereof, and
(ii) at least one further segment ($S_2$), which contains a second pharmacologically active ingredient ($A_2$) and provides immediate release thereof,
wherein the at least one formed segment ($S_1$) exhibits a higher breaking strength than the at least one further segment ($S_2$) and the at least one formed segment ($S_1$) exhibits a breaking strength of more than 500 N.

BACKGROUND OF THE INVENTION

A large number of pharmacologically active substances have a potential for being abused or misused, i.e. they can be used to produce effects which are not consistent with their intended use. Thus, e.g. opioids which exhibit an excellent efficacy in controlling severe to extremely severe pain, are frequently abused to induce euphoric states similar to being intoxicated. In particular, active substances which have a psychotropic effect are abused accordingly.

To enable abuse, the corresponding pharmaceutical dosage forms, such as pharmaceutical dosage forms or capsules are crushed, for example ground by the abuser, the active substance is extracted from the thus obtained powder using a preferably aqueous liquid and after being optionally filtered through cotton wool or cellulose wadding, the resultant solution is administered parenterally, in particular intravenously. This type of dosage results in an even faster diffusion of the active substance compared to the oral abuse, with the result desired by the abuser, namely the kick. This kick or these intoxication-like, euphoric states are also reached if the powdered pharmaceutical dosage form is administered nasally, i.e. is sniffed.

Various concepts for the avoidance of drug abuse have been developed.

It has been proposed to incorporate in pharmaceutical dosage forms aversive agents and/or antagonists in a manner so that they only produce their aversive and/or antagonizing effects when the pharmaceutical dosage forms are tampered with. However, the presence of such aversive agents is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse, of the pharmaceutical dosage forms by the means usually available to a potential abuser is prevented or at least complicated. Such pharmaceutical dosage forms are useful for avoiding drug abuse of the pharmacologically active ingredient contained therein, as they may not be powdered by conventional means and thus, cannot be administered in powdered form, e.g. nasally. The mechanical properties, particularly the high breaking strength of these pharmaceutical dosage forms renders them tamper-resistant. In the context of such tamper-resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO2009/092601.

Besides tampering of pharmaceutical dosage forms in order to abuse the drugs contained therein, the potential impact of concomitant intake of ethanol on the in vivo release of drugs from modified release oral formulations (dose-dumping) has recently become an increasing concern. Controlled or modified release formulations typically contain a higher amount of the pharmacologically active ingredient relative to its immediate release counterpart. If the controlled release portion of the formulation is easily defeated, the end result is a potential increase in exposure to the active drug and possible safety concerns. In order to improve safety and circumvent intentional tampering (e.g. dissolving a controlled release pharmaceutical dosage form in ethanol to extract the drug), a reduction in the dissolution of the modified release fractions of such formulations, in ethanol, may be of benefit. Accordingly, the need exists to develop new formulations having reduced potential for dose dumping in alcohol.

Furthermore, the release kinetics of the pharmacologically active ingredients is an important factor. It is well known that depending on how a pharmaceutically pharmacologically active ingredient is formulated into a tablet its release pattern can be modified.

On the one hand, formulations providing immediate release upon oral administration have the advantage that they lead to a fast release of the pharmacologically active ingredient in the gastrointestinal tract. As a result, a comparatively high dose of the pharmacologically active ingredient is quickly absorbed leading to high plasma levels within a short period of time and resulting in a rapid onset of medicinal action, i.e. medicinal action begins shortly after administration. At the same time, however, a rapid reduction in the medicinal action is observed, because metabolization and/or excretion of the pharmacologically active ingredient cause a decrease of plasma levels. For that reason, formulations providing immediate release of pharmacologically active ingredients typically need to be administered frequently, e.g. six times per day. This may cause comparatively high peak plasma pharmacologically active ingredient concentrations and high fluctuations between peak and trough plasma pharmacologically active ingredient concentrations which in turn may deteriorate tolerability.

Controlled release (e.g. delayed release, prolonged release, sustained release, and the like) may be based upon various concepts such as coating the pharmaceutical dosage form with a controlled release membrane, embedding the pharmacologically active ingredient in a matrix, binding the pharmacologically active ingredient to an ion-exchange resin, forming a complex of the pharmacologically active ingredient, and the like. In this context it can be referred to, e.g., W. A. Ritschel, Die Tablette, 2. Auflage, Editio Cantor Verlag Aulendorf, 2002.

In comparison to formulations providing immediate release, formulations providing prolonged release upon oral administration have the advantage that they need to be administered less frequently, typically once daily or twice daily. This can reduce peak plasma pharmacologically active ingredient concentrations and fluctuations between peak and trough plasma pharmacologically active ingredient concentrations which in turn may improve tolerability.

However, especially patients starting their treatment with controlled release formulations often desire a rapid onset of medicinal action. Therefore, a need exists to develop tamper resistant formulations which provide a quick medicinal action while at the same time having the benefits of controlled or modified release formulations.

US 2009/0005408 relates to a process for the production of solid pharmaceutical dosage forms with at least reduced potential for abuse, by a) shaping a formulation mixture containing at least one active ingredient with potential for abuse and at least one synthetic or natural polymer (C), which exhibits a breaking strength of at least 500 N, into formed articles by application of force, b) optionally singulating the formed articles and optionally in each case grading them by size and, c) after or during heating at least to the softening point of the polymer (C), exposing the formed articles to force until they have a breaking hardness of at least 500 N, optionally providing them with a cover and optionally mixing all the formed articles back together again.

US 2009/0022798 and WO 2009/014534, respectively, discloses formulations and methods for the delivery of drugs, particularly drugs of abuse, having an abuse-relevant drug substantially confined in the core and a non-abuse relevant drug in a non-core region. These formulations have reduced potential for abuse. In the formulation, preferably the abuse relevant drug is an opioid and the non-abuse relevant drug is acetaminophen or ibuprofen. More preferably, the opioid is hydrocodone, and the non-abuse relevant analgesic is acetaminophen. In certain preferred embodiments, the dosage forms are characterized by resistance to solvent extraction; tampering, crushing or grinding. In a preferred embodiment, the dosage forms have a breaking strength of at least 500 N. Certain embodiments relate to dosage forms providing an initial burst of release of drug followed by a prolonged period of controllable drug release. When providing these dosage forms with tamper resistant properties, however, the initial burst of release of drug is difficult to achieve, as tamper-resistance and in particular the breaking strength typically relies on the presence of polymers that act as release matrix material slowing down the release of the drug from the dosage form. Therefore, it is only meaningful to provide a combination of tamper resistance, in particular a high breaking strength, and an initial burst of release of the drug when this drug has a potential for being abused. Further, the non-core layer of the drug product is explicitly applied using a film-coating process. A film-coating process is disadvantageous due to the high cost it produces during manufacturing. The film-forming layer material is first dissolved, then sprayed on the core and finally the solvent is removed, all leading to long process times with high energy consumption. Due to the high amount of active that needs to be present in the film-layer, this is a significant disadvantage for a cost-competitive manufacturing of the drug product.

EP 1 980 245 A1 relates to a bilayer dosage form comprising: (i) an upper layer (a) comprising a lyophilized dosage form of active pharmaceutical ingredient(s) (API(s)); and (ii) a base line layer (b) formulated to adhere to the oral mucosa and intended for delayed, sustained or extended release of API(s) and/or excipient(s).

WO 2009/005803 A1 relates to a pharmaceutical composition in the form of a combination tablet. The tablet has a rapidly absorbed component that enters the circulation by traversing the buccal mucosa, and a more slowly absorbed component that is swallowed. The therapeutic agent in the swallowed portion is absorbed across the gastric mucosa. The rapid and slow components may have identical or different therapeutic agents depending on the application to a specific medical condition One embodiment of the combination tablet includes a prostaglandin inhibitor in the rapidly absorbed component in order to mitigate the side effects of immediate release niacin that is in the slow absorbing component.

The properties of the pharmaceutical dosage forms of the prior art are not satisfactory in every respect.

It is an object of the invention to provide pharmaceutical dosage forms which have advantages over the pharmaceutical dosage forms of the prior art. The pharmaceutical dosage forms should provide prolonged release of a first pharmacologically active ingredient and immediate release of a second pharmacologically active ingredient, wherein particularly the first pharmacologically active ingredient is safeguarded from abuse.

This object has been achieved by the subject-matter described herein below.

A first aspect of the invention relates to a pharmaceutical dosage form comprising
(i) at least one formed segment ($S_1$), which contains a first pharmacologically active ingredient ($A_1$) and provides prolonged release thereof, and
(ii) at least one further segment ($S_2$), which contains a second pharmacologically active ingredient ($A_2$) and provides immediate release thereof,
wherein the at least one formed segment ($S_1$) exhibits a higher breaking strength than the at least one further segment ($S_2$) and the at least one formed segment ($S_1$) exhibits a breaking strength of more than 500 N.

Another aspect of the invention relates to a process for the production of said pharmaceutical dosage form comprising the steps of
(i) thermoforming at least one formed segment ($S_1$) comprising a first pharmacologically active ingredient ($A_1$) and a natural or synthetic polymer (C), preferably such that said formed segment ($S_1$) provides prolonged release of said first pharmacologically active ingredient ($A_1$);
(ii) providing at least one further segment ($S_2$) comprising a second pharmacologically active ingredient ($A_2$) and preferably providing immediate release thereof; and
(iii) combining the at least one formed segment ($S_1$), the at least one further segment ($S_2$) and optionally further excipients.

A further aspect of the invention relates to said pharmaceutical dosage form for use in the treatment of pain, wherein the dosage form is swallowed as a whole.

It has been surprisingly found that tamper-resistant pharmaceutical dosage forms can be provided that contain a first pharmacologically active ingredient in a prolonged release form and a second pharmacologically active ingredient in an immediate release form. Patient compliance can be improved by providing a rapid but also prolonged medicinal effect.

Unless expressly stated otherwise, all percentages are by weight (wt.-%).

For the purpose of specification, the term "pharmaceutical dosage form" refers to a pharmaceutical entity which contains the first pharmacologically active ingredient ($A_1$) and the second pharmacologically active ingredient ($A_2$) and which is to be administered to a patient (dose unit). It may be compressed or molded during manufacture, and it may be of almost any size, shape, weight, and color. The pharmaceutical dosage form is preferably solid or semisolid.

The pharmaceutical dosage form is preferably intended for oral administration. It is preferably provided in form of a single body that can be easily swallowed by a patient. Typical examples of pharmaceutical dosage forms according to the invention include, but are not limited to tablets (e.g. coated tablets, multilayer tablets, and the like) and capsules.

For the purpose of specification, the term "segment" as used herein refers to any physically distinct entity of the pharmaceutical dosage form that contains the first pharmacologically active ingredient ($A_1$) or the second pharmacologically active ingredient ($A_2$) and that can be distinguished from another physically distinct entity of the pharmaceutical dosage form. Preferably, every segment is solid or semisolid.

The formed segment ($S_1$) and the further segment ($S_2$) of the pharmaceutical dosage form preferably do not consist of the first pharmacologically active ingredient ($A_1$) and the second pharmacologically active ingredient ($A_2$), respectively, but contain further ingredients such as pharmaceutical excipients. Thus, the formed segment ($S_1$) and the further segment ($S_2$) can be regarded as greater units of compacted, granulated, congealed or otherwise agglomerated material, comprising inter alia but preferably not consisting of the first pharmacologically active ingredient ($A_1$) and the second pharmacologically active ingredient ($A_2$), respectively.

In a preferred embodiment, besides the first pharmacologically active ingredient ($A_1$) the formed segment(s) ($S_1$) comprise(s) at least a portion of the total amount of the second pharmacologically active ingredient ($A_2$) that is contained in the pharmaceutical dosage form.

In another preferred embodiment, besides the first pharmacologically active ingredient ($A_2$) the further segment(s) ($S_2$) comprise(s) at least a portion of the total amount of the first pharmacologically active ingredient ($A_1$) that is contained in the pharmaceutical dosage form.

Besides the content of the first pharmacologically active ingredient ($A_1$) and the second pharmacologically active ingredient ($A_2$), the formed segment ($S_1$) and the further segment ($S_2$) of the pharmaceutical dosage form preferably differ in at least one of the following properties and can be distinguished by said property: composition of ingredients (e.g. nature and/or amount), total weight, density, hardness, breaking strength, size, shape, color, morphology, coherence (e.g. monolithic mass vs. multitude of particulates) and/or porosity.

Typically, any segment of the pharmaceutical dosage form covers at least 1 vol.-%, or at least 2 vol.-%, or at least 5 vol.-%, more preferably at least 10 vol.-% or at least 15 vol.-%, still more preferably at least 17.5 vol.-% or at least 20 vol.-%, yet more preferably at least 22.5 vol.-% or at least 25 vol.-%, even more preferably at least 30 vol.-% or at least 35 vol.-%, most preferably at least 40 vol.-%, and in particular at least 45 vol.-%, of the total volume of the pharmaceutical dosage form. Thus, physically distinct entities that are so small that they do not cover such portion of the total volume of the pharmaceutical dosage form are typically not to be regarded as "segment" in the meaning of the invention.

The formed segment ($S_1$) and the further segment ($S_2$) of the pharmaceutical dosage form are separate of one another, i.e. are at different locations of the pharmaceutical dosage form. However, it is possible that one segment partially or completely surrounds the other segment. Nevertheless, it is not possible that a given location of the pharmaceutical dosage form contains both, matter of the formed segment ($S_1$) and simultaneously matter of the further segment ($S_2$).

For example, a segment may be a powdery material, a coherent matrix material in which e.g. another segment may be embedded, or a spatially confined area within the pharmaceutical dosage form such as a layer of the pharmaceutical dosage form or a coating of the pharmaceutical dosage form.

In particular, when the pharmaceutical dosage form is provided in form of a multilayered tablet, every layer of the multilayered tablet constitutes a segment of the dosage form. When the pharmaceutical dosage form is provided in form of a coated tablet, the tablet core constitutes one segment whereas the coating constitutes another segment of the dosage form.

When the pharmaceutical dosage form is particulate, e.g. provided in form of a capsule filled with a multitude of pellets and a powder, respectively, the situation can be different. Under these circumstances, every pellet that contains the first pharmacologically active ingredient ($A_1$) or the second pharmacologically active ingredient ($A_2$) can be regarded as an individual formed segment ($S_1$) within a plurality of formed segments ($S_1$) and as an individual further segment ($S_2$) within a plurality of further segments ($S_2$), respectively.

When the first pharmacologically active ingredient ($A_1$) or the second pharmacologically active ingredient ($A_2$) is contained as a constituent of a powdery material, however, the mesoscopic or microscopic particles of the first pharmacologically active ingredient ($A_1$) or the second pharmacologically active ingredient ($A_2$) are typically not to be regarded as formed segment ($S_1$) and further segment ($S_2$), respectively; under these circumstances, the entire powdery material is to be regarded as formed segment ($S_1$) and further segment ($S_2$), respectively. Accordingly, when the pharmaceutical dosage form is a capsule filled with a multitude of pellets containing the first pharmacologically active ingredient ($A_1$) and with a powdery material containing the second pharmacologically active ingredient ($A_2$) in powderous form, said multitude of pellets constitutes a multitude of formed segments ($S_1$), whereas said powdery material constitutes a (single) further segment ($S_2$), although the pellets and the powdery material may be homogeneously admixed with one another.

The formed segment ($S_1$) and the further segment ($S_2$) of the pharmaceutical dosage form can be distinguished from one another.

The pharmaceutical dosage form according to the invention comprises at least one formed segment ($S_1$) (monolith) but may also contain a plurality of formed segments ($S_1$) (e.g. multitude of particles). When the pharmaceutical dosage form according to the invention comprises a plurality of formed segments ($S_1$), the individual formed segments ($S_1$) are preferably of essentially the same type and nature, e.g. composition, total weight, density, hardness, breaking strength, size, shape, color, morphology, coherence and/or porosity. Preferably, the pharmaceutical dosage form contains not more than 10 formed segments ($S_1$), more preferably not more than 9, still more preferably not more than 8, yet more preferably not more than 7, even more preferably not more than 6, most preferably not more than 5, and in particular not more than 4 formed segments ($S_1$). Preferably, the pharmaceutical dosage form contains 1, 2 or 3 formed segments ($S_1$).

The pharmaceutical dosage form according to the invention comprises at least one further segment ($S_2$) (monolith) but may also contain a plurality of further segments ($S_2$) (multitude of particles). When the pharmaceutical dosage form according to the invention comprises a plurality of further segments (S$_2$), the individual further segments (S$_2$) are preferably of essentially the same type and nature, e.g. composition, total weight, density, hardness, breaking strength, size, shape, color, morphology, coherence and/or porosity. Preferably, the pharmaceutical dosage form contains not more than 10 further segments (S$_2$), more preferably not more than 9, still more preferably not more than 8, yet more preferably not more than 7, even more preferably not more than 6, most preferably not more than 5, and in particular not more than 4 further segments (S$_2$). Preferably, the pharmaceutical dosage form contains 1, 2 or 3 further segments (S$_2$). When the pharmaceutical dosage form contains 1 further segment (S$_2$), said further segment (S$_2$) can preferably be a coherent mass or in form of a powdery material.

When the pharmaceutical dosage form contains more than one formed segment (S$_1$) and/or more than one further segment (S$_2$), the pharmaceutical dosage form is particulate.

In a preferred embodiment, the pharmaceutical dosage form contains additional segments (S$_3$), e.g. segments which contain pharmacologically active ingredient but are essentially not of the same type and nature as formed segments (S$_1$) and further segments (S$_2$), respectively. For example, the additional segments (S$_3$) may contain the first pharmacologically active ingredient (A$_1$) and/or the second pharmacologically active ingredient (A$_2$) and/or a third pharmacologically active ingredient (A$_3$) and provide e.g. prolonged release thereof. Prolonged release may be achieved e.g. by embedding the pharmacologically active ingredient in a polymer matrix differing from the polymer matrix that is preferably contained in formed segment(s) (S$_1$). Thus, under these circumstances, the polymer matrices of formed segment(s) (S$_1$) and additional segments (S$_3$) differ from one another and accordingly, the in vitro release profile may differ as well.

While the pharmaceutical dosage form may contain additional segments (S$_3$), e.g. segments which contain pharmacologically active ingredient but are essentially not of the same type and nature as formed segments (S$_1$) and further segments (S$_2$), respectively, the pharmaceutical dosage form preferably consists of the at least one formed segment (S$_1$) and the at least one further segment (S$_2$), but does not contain additional segments (S$_3$). In a preferred embodiment, the at least one formed segment (S$_1$) and the at least one further segment (S$_2$) are present in a container, e.g. a hard gelatine capsule.

Preferably, when the pharmaceutical dosage form is particulate, (i) the formed segments (S$_1$) as well as the further segments (S$_2$), or (ii) the formed segments (S$_1$) but not the further segment (S$_2$), or (iii) the further segments (S$_2$) but not the formed segment (S$_1$)

are particulate.

When (i) the formed segment (S$_1$) as well as the further segment (S$_2$) are each particulate (but not powdery), the formed segments (S$_1$) can be admixed with the further segments (S$_2$). Nevertheless, even under these specific circumstances, the formed segments (S$_1$) each constitute a physically distinct entity of the pharmaceutical dosage form that can be distinguished from the further segments (S$_2$) each constituting another physically distinct entity of the pharmaceutical dosage form.

In a preferred embodiment, the formed segment(s) (S$_1$) and the further segment(s) (S$_2$) each constitute a spatially confined area within the pharmaceutical dosage form. According to this embodiment, the formed segment (S$_1$) and/or further segment (S$_2$) preferably forms a layer, a coating, a core or a mantle of the pharmaceutical dosage form which is preferably in the form of a tablet.

BRIEF DESCRIPTION OF THE DRAWINGS

Preferred embodiments of tablets comprising the formed segment (S$_1$) and the further segment (S$_2$) are illustrated in FIG. 1.

In another preferred embodiment, the formed segment(s) (S$_1$) and the further segment(s) (S$_2$) are both contained in a container, e.g. a hard gelatine capsule.

Figure 2:
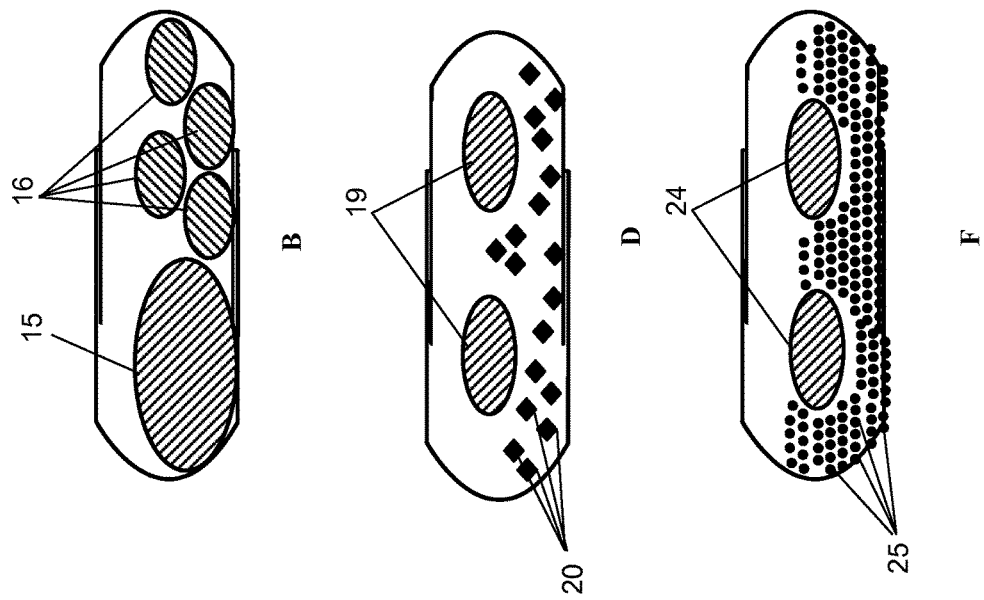

Preferred embodiments of capsules comprising formed segment(s) (S$_1$) and further segment(s) (S$_2$) are illustrated in FIG. 2.

FIG. 2A schematically illustrates a capsule formed of capsule body (11) and capsule lid (12). The capsule contains a formed segment (S$_1$) (13) as well as a further segment (S$_2$) (14).

FIG. 2B schematically illustrates a capsule containing a formed segment (S$_1$) (15) as well as a plurality of further segments (S$_2$) (16).

FIG. 2C schematically illustrates a capsule containing a plurality of formed segments (S$_1$) (17) as well as a plurality of further segments (S$_2$) (18).

FIG. 2D schematically illustrates a capsule containing a plurality of formed segments (S$_1$) (19) as well as a plurality of particles (20) that are smaller than further segments (S$_2$) (18) of FIG. 2C. Nevertheless, every particle (20) contains the second pharmacologically active ingredient (A$_2$) and thus, every particle (20) constitutes an individual further segment (S$_2$) so that this capsule also contains a plurality of further segments (S$_2$) (20).

FIG. 2E schematically illustrates a capsule containing a plurality of formed segments (S$_1$) (21), a plurality of particles (22), and a plurality of particles (23). Particles (22) contain the second pharmacologically active ingredient (A$_2$), whereas particles (23) contain neither the first pharmacologically active ingredient (A$_1$) nor the second pharmacologically active ingredient (A$_2$). Every particle (22) constitutes an individual further segment (S$_2$) so that this capsule also contains a plurality of further segments (S$_2$) (20). However, particles (23) do not constitute a segment within the meaning of the invention.

FIG. 2F schematically illustrates a capsule containing a plurality of formed segments (S$_1$) (24) as well as a powdery material (25). The powdery material (25) contains the second pharmacologically active ingredient (A$_2$), but not as a constituent of a greater physical entity, but if appropriate, simply in admixture with other excipients that are contained in the powdery material. Under these circumstances, the entirety of the powdery material (25) constitutes one further segment (S$_2$).

Figure 3:
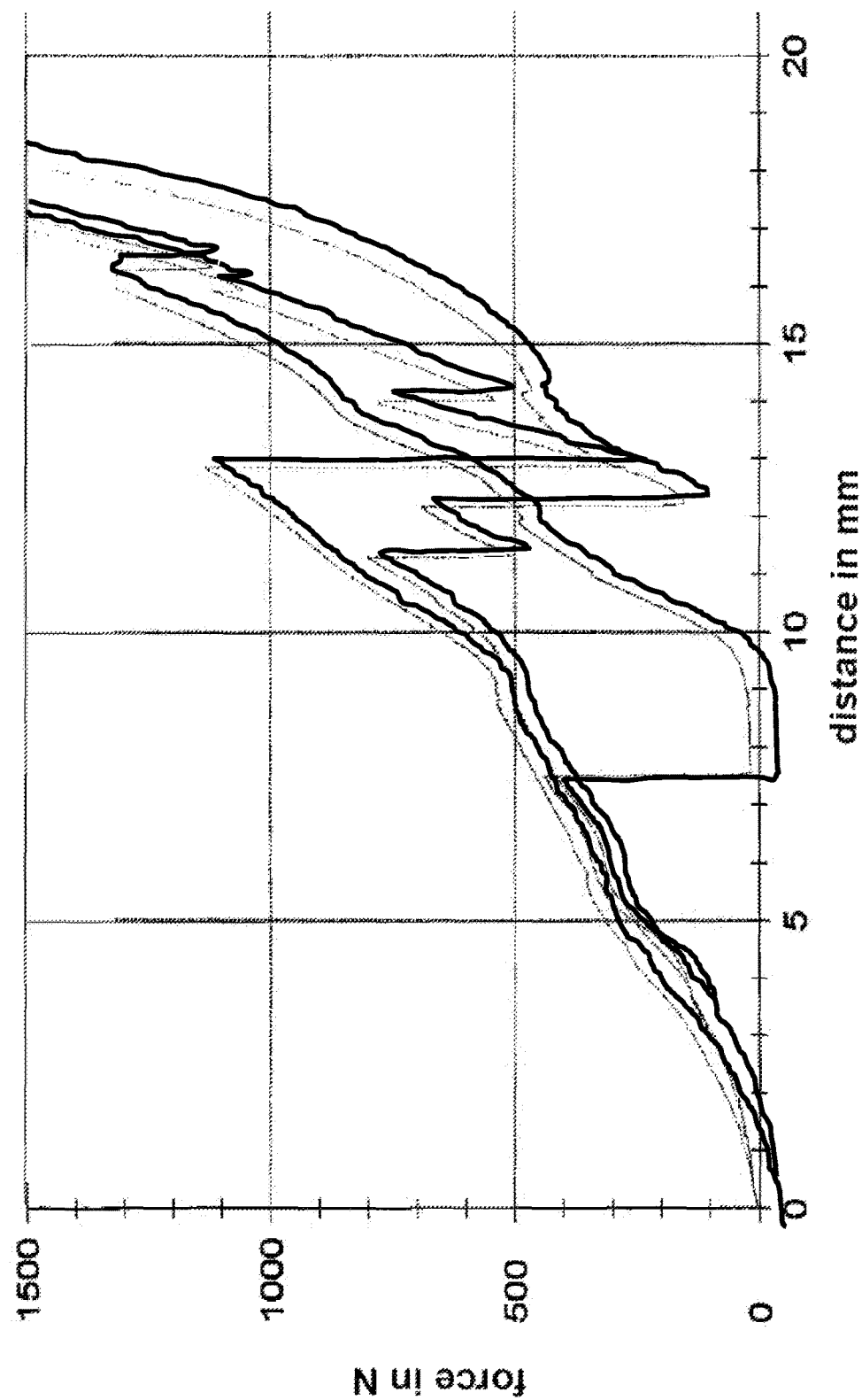

FIG. 3 shows the force distance diagram of cut rods having a breaking strength of more than 500 N.

Figure 4:
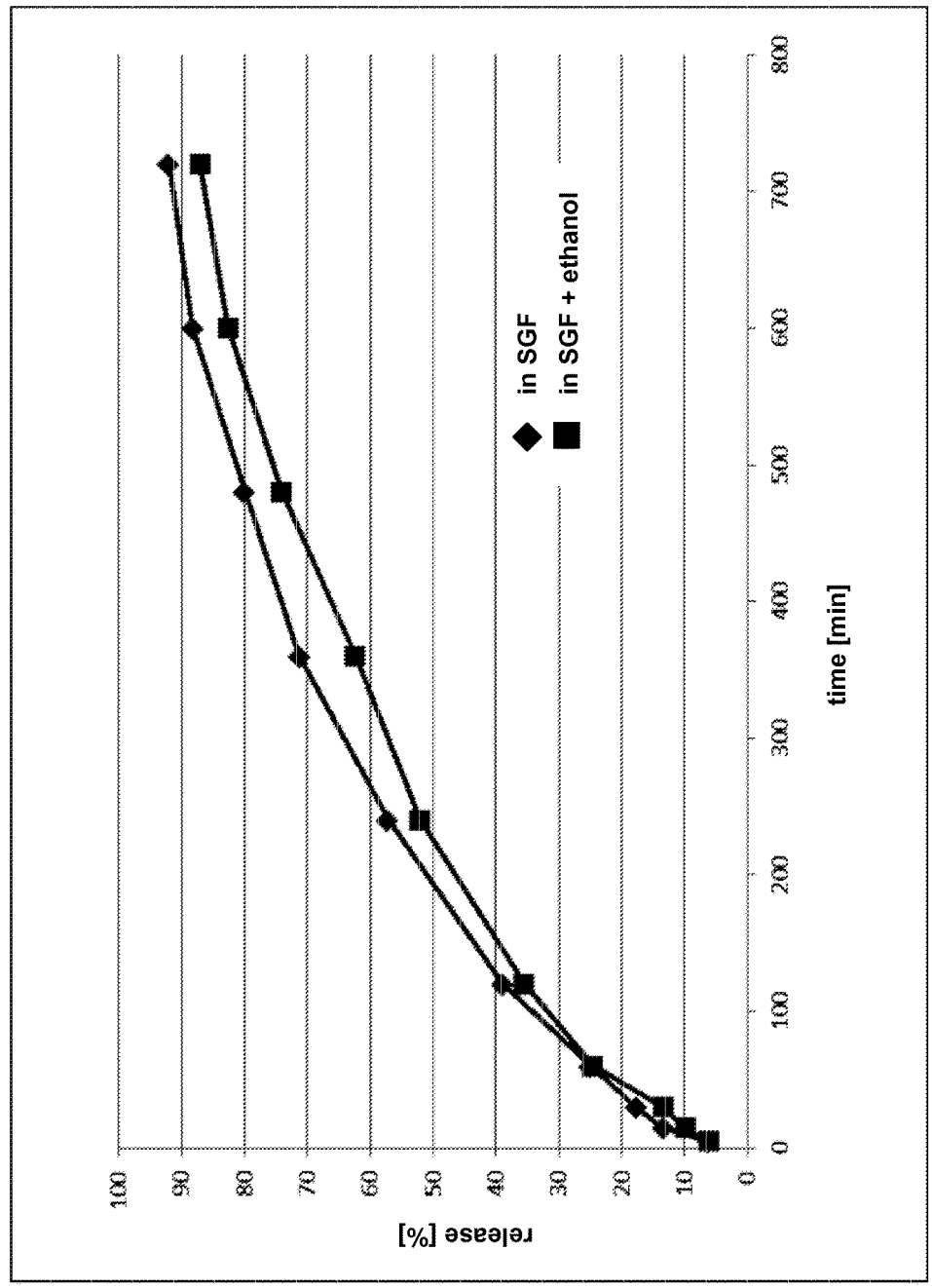

FIG. 4 shows the release profiles of one cut rod determined under in vitro conditions (n=3) using the basket method with sinker according to Ph. Eur. at 75 rpm in 600 mL of SGF (pH 1.2) and SGF (pH 1.2)+40% ethanol, respectively.

Figure 5:
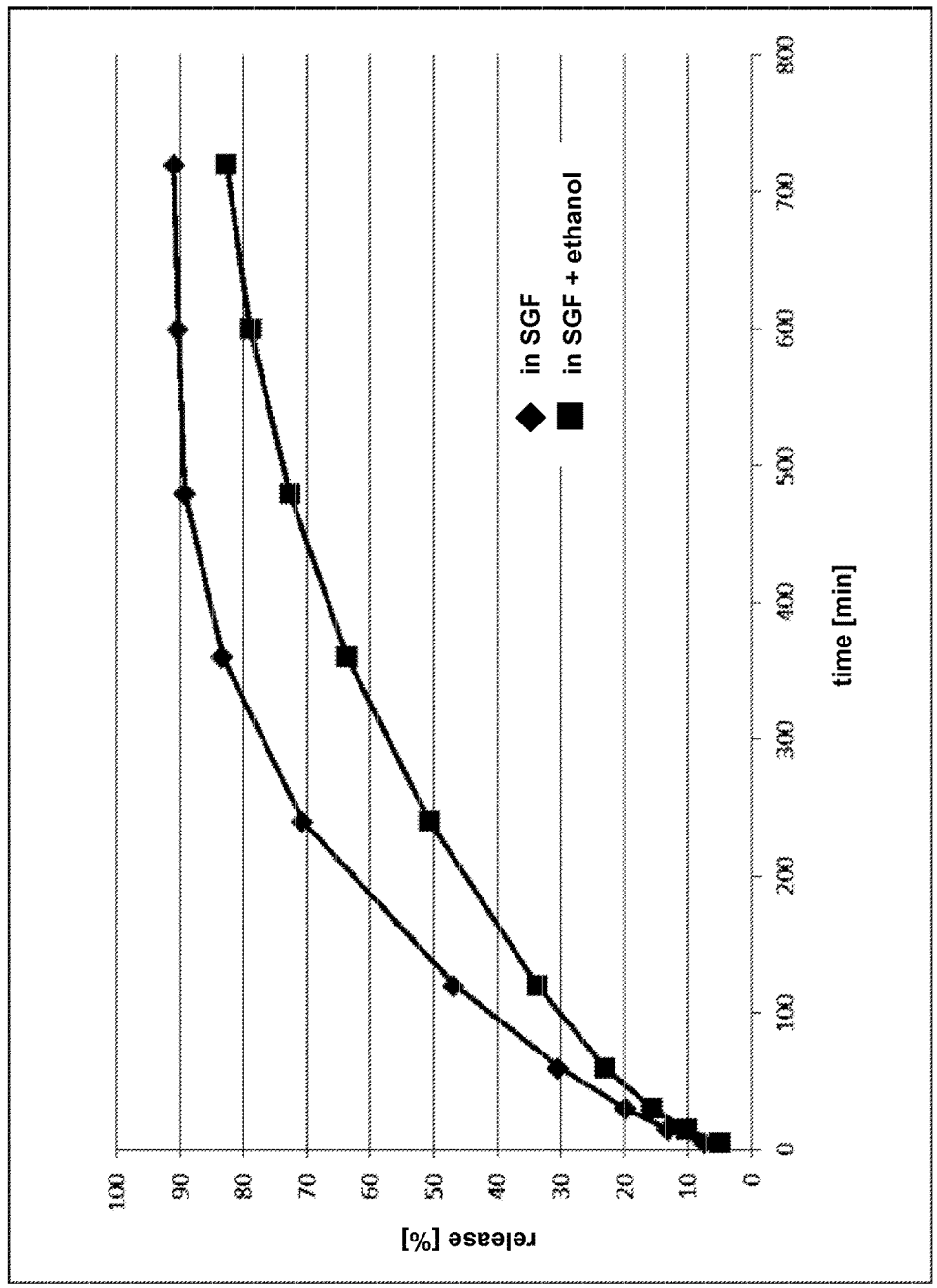

FIG. 5 shows the release profiles of two cut rods determined under in vitro conditions (n=3) using the basket method with sinker according to Ph. Eur. (one sinker per cut rod) at 75 rpm in 600 mL of SGF (pH 1.2) and SGF (pH 1.2)+40% ethanol, respectively.

Figure 6:
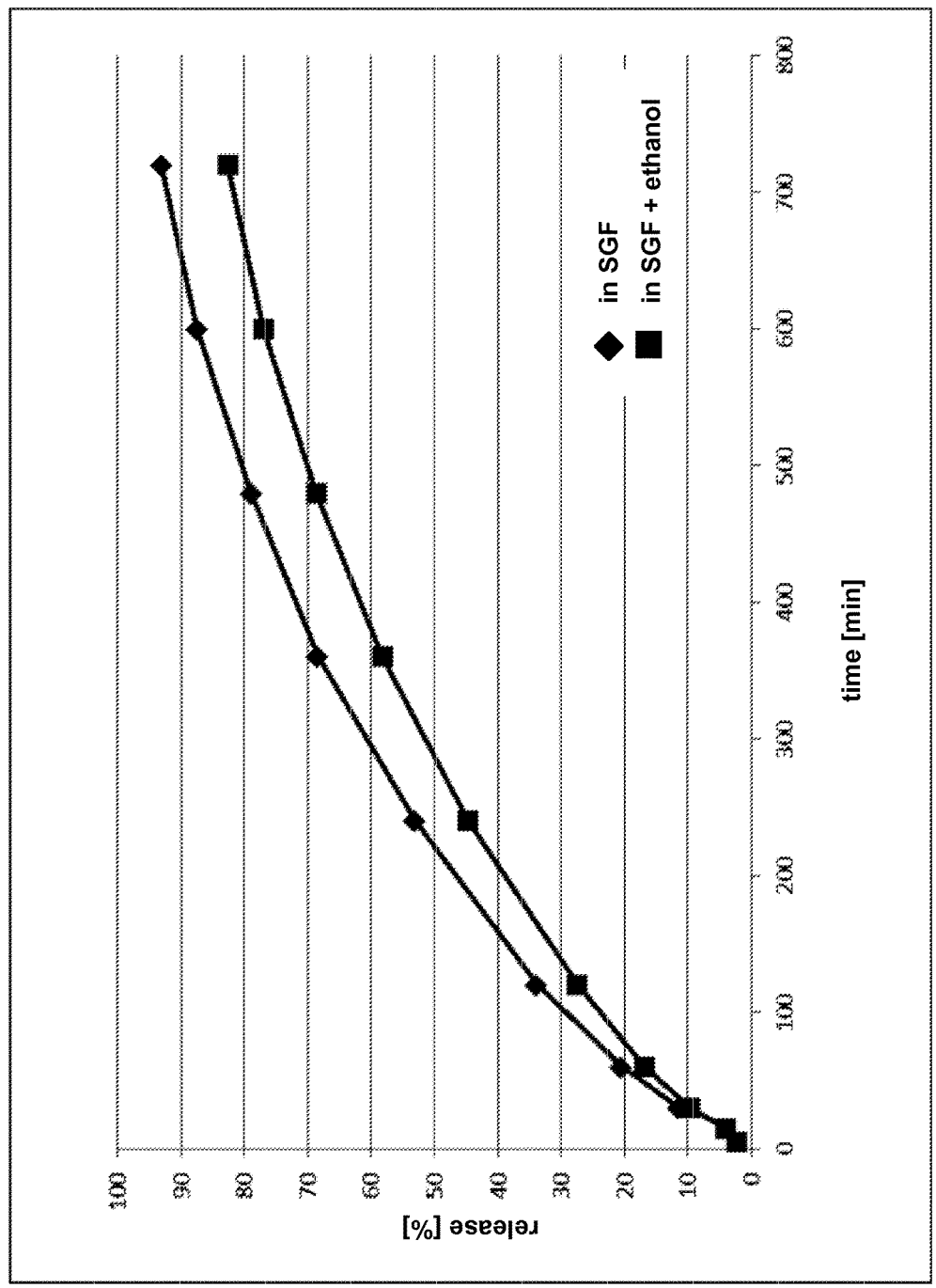

FIG. 6 shows the release profiles of one cut rod in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Figure 7:
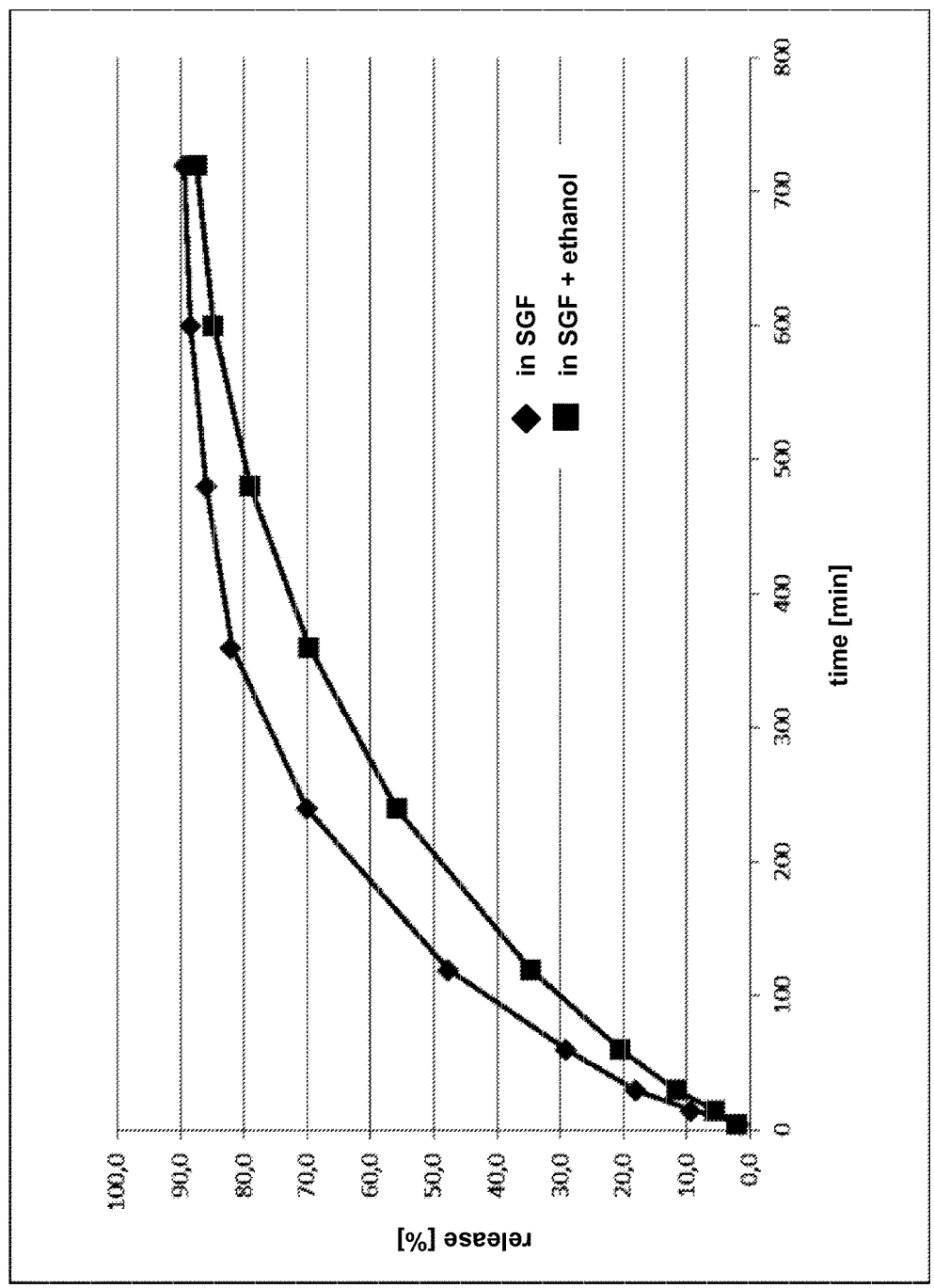

FIG. 7 shows the release profiles of two cut rods and a lactose tablet in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Figure 8:
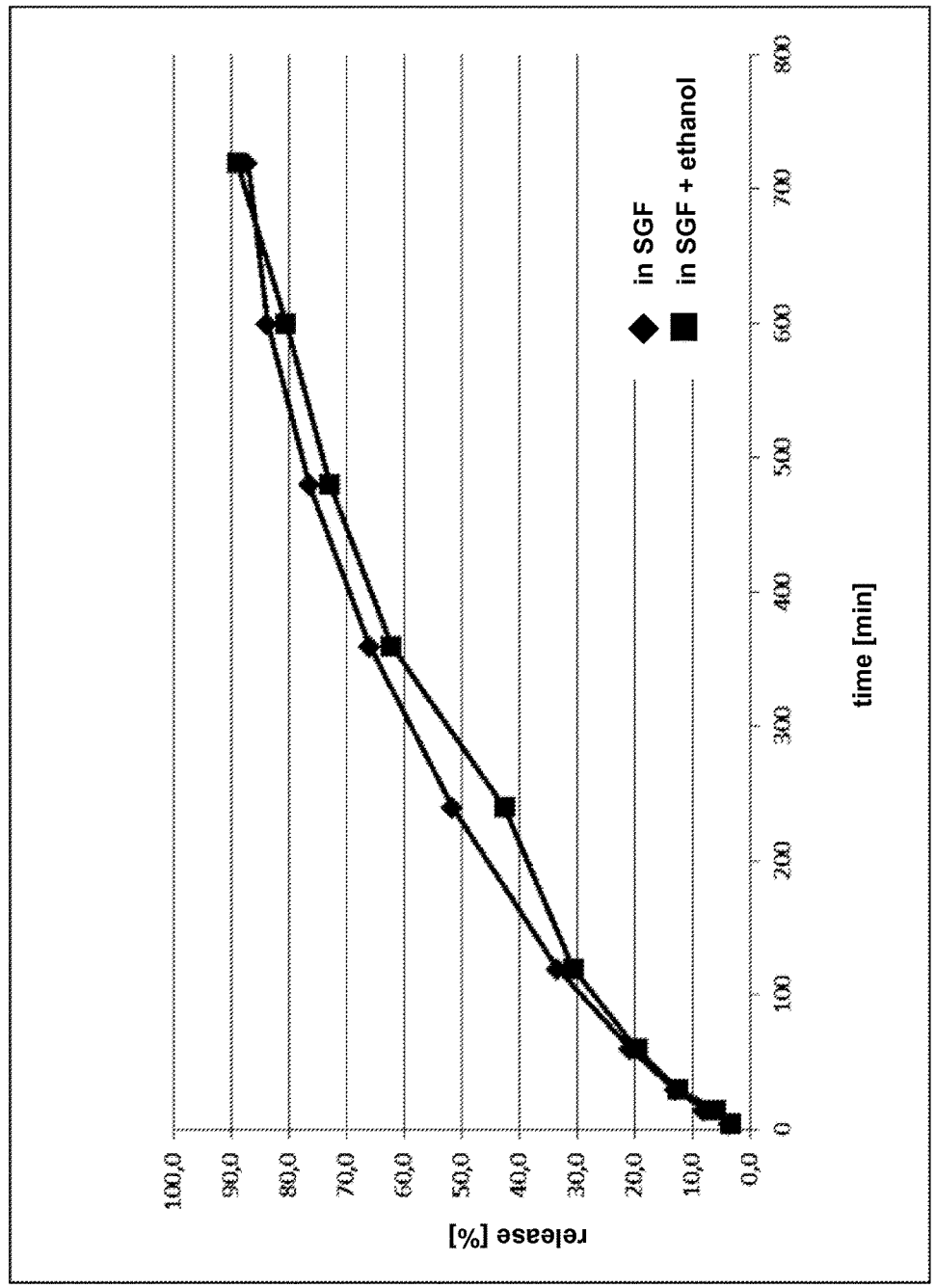

FIG. 8 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

Figure 9:
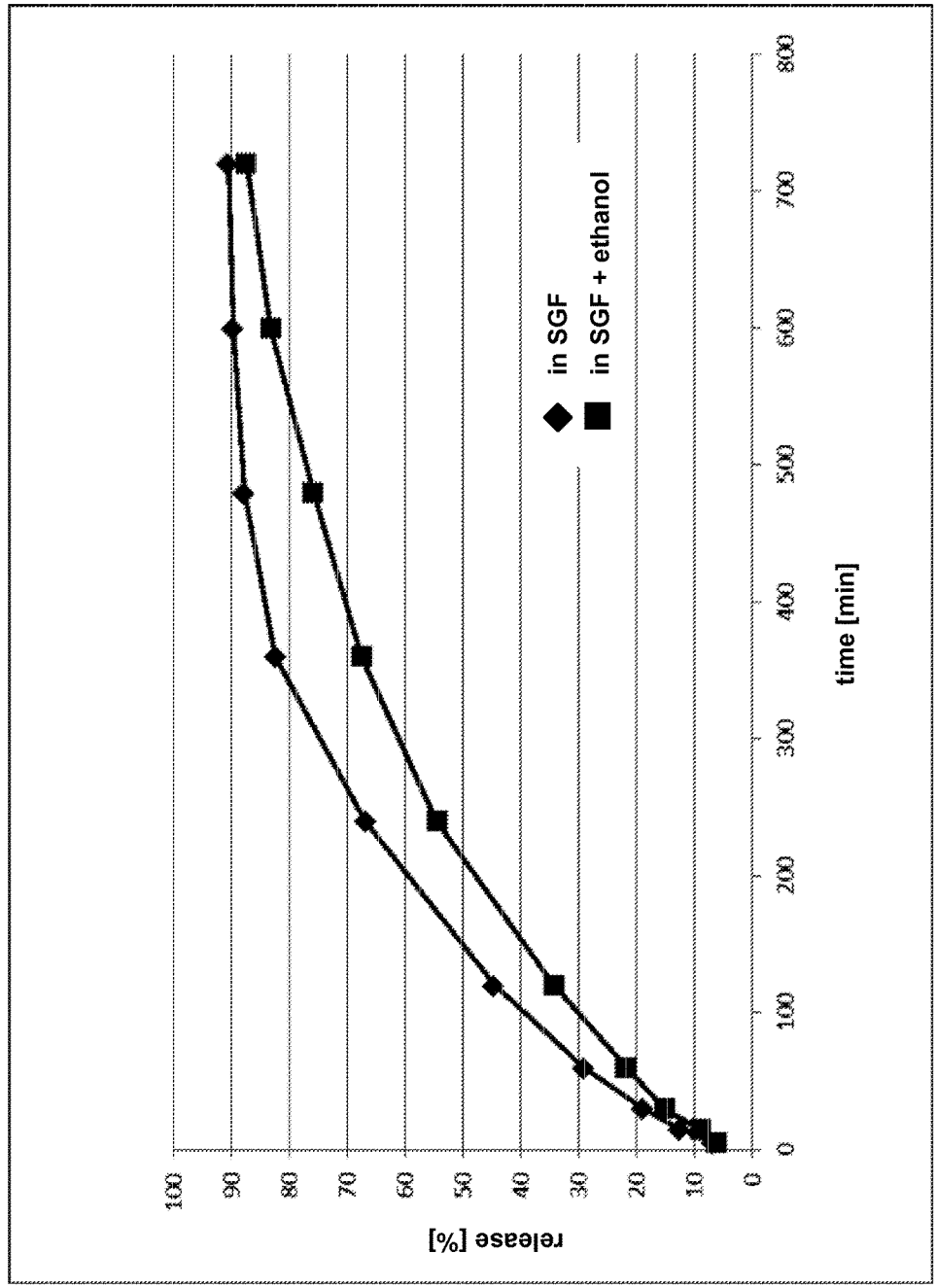

FIG. 9 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

FIGS. 10 to 14 show combinations of the release profiles obtained in Reference Examples 2 to 7 (FIGS. 4 to 9).

Preferably, the total content of the formed segment(s) ($S_1$) in the pharmaceutical dosage form according to the invention is at most 95 wt.-%, more preferably at most 85 wt.-%, still more preferably at most 75 wt.-%, yet more preferably at most 65 wt.-%, most preferably at most 55 wt.-% and in particular at most 50 wt.-%, based on the total weight of the pharmaceutical dosage form.

Preferably, the total content of the formed segment(s) ($S_1$) in the pharmaceutical dosage form according to the invention is at least 5 wt.-% or at least 10 wt.-%, more preferably at least 15 wt.-% or at least 20 wt.-%, still more preferably at least 25 wt.-% or at least 30 wt.-%, even more preferably at least 35 wt.-% or at least 40 wt.-%, yet more preferably at least 45 wt.-% or at least 50 wt.-%, most preferably at least 55 wt.-% or at least 60 wt.-%, and in particular at least 65 wt.-% or at least 70 wt.-%; based on the total weight of the pharmaceutical dosage form.

In a preferred embodiment, the formed segment ($S_1$) and/or the further segment ($S_2$) is monolithic, i.e. the dosage form contains a single formed segment ($S_1$) and/or a single further segment ($S_2$), respectively.

In this regard, monolithic preferably refers to a single coherent entity (monolith) preferably having a weight of 100 mg or more. According to this embodiment, the monolith preferably has a weight of at least 120 mg, more preferably at least 140 mg, still more preferably at least 160 mg, most preferably at least 180 mg and in particular at least 200 mg. Preferably, the monolith has a weight of from 100 to 1000 mg, more preferably 120 to 900 mg, still more preferably 140 to 800 mg, yet more preferably 150 to 700 mg, even more preferably 160 to 600 mg, most preferably 170 to 500 mg and in particular 200 to 400 mg. For the purpose of definition, a monolithic segment that is film-coated is also to be regarded as a monolithic segment according to the invention.

In another preferred embodiment, the formed segments ($S_1$) and/or the further segments ($S_2$) are particulate, preferably oligoparticulate or multiparticulate, i.e. the dosage form contains a multitude of formed segments ($S_1$) and/or a multitude of further segment ($S_2$), respectively. For the purpose of the specification, the term "particulate", "oligoparticulate" or "multiparticulate" refers to a discrete mass of material, i.e. multitude of particles, which are solid, e.g. at 20° C. or at room temperature or ambient temperature. Preferably a particle is solid at 20° C.

In a preferred embodiment, the formed segments ($S_1$) and/or the further segments ($S_2$) are oligoparticulate. In this regard, oligoparticulate preferably means that all individual oligoparticles, i.e. formed segments ($S_1$) and/or further segments ($S_2$), each have a weight of 20 mg or more. According to this embodiment, all individual oligoparticles, i.e. formed segments ($S_1$) and/or further segments ($S_2$), each preferably have a weight of at least 30 mg, more preferably at least 40 mg, still more preferably at least 50 mg, most preferably at least 60 mg and in particular at least 100 mg. Preferably, all individual oligoparticles, i.e. formed segments ($S_1$) and/or further segments ($S_2$), each have a weight of from 20 to 1000 mg, more preferably 30 to 800 mg, still more preferably 40 to 600 mg, yet more preferably 50 to 400 mg, even more preferably 60 to 200 mg, most preferably 70 to 150 mg and in particular 80 to 120 mg.

Further, according to this embodiment, the pharmaceutical dosage form preferably comprises at most 10, more preferably at most 9, still more preferably at most 8, yet more preferably at most 7, even more preferably at most 6, most preferably at most 5, and in particular at most 4 or 3 or 2 formed segments ($S_1$) and/or further segments ($S_2$). When the formed segments ($S_1$) and/or the further segments ($S_2$) are oligoparticulate, the pharmaceutical dosage form may further comprise drug-free particles, which may each have an individual weight of less than 20 mg.

In another preferred embodiment, the formed segments ($S_1$) and/or the further segments ($S_2$) are multiparticulate. In this regard, multiparticulate preferably means that all individual multiparticles, i.e. formed segments ($S_1$) and/or further segments ($S_2$), each have a weight of less than 20 mg. According to this embodiment, all multiparticles, i.e. formed segments ($S_1$) and/or further segments ($S_2$), each preferably have a weight of less than 18 mg, more preferably less than 16 mg, still more preferably less than 14 mg, yet more preferably less than 12 mg, even more preferably less than 10 mg, most preferably less than 8 mg, and in particular less than 6 or 4 mg. Further, according to this embodiment, the pharmaceutical dosage form preferably comprises at least 2, more preferably at least 4, still more preferably at least 6, yet more preferably at least 8, even more preferably at least 10, most preferably at least 15 and in particular at least 20 or at least 100 or at least 1000 particles, i.e. formed segments ($S_1$) and/or further segments ($S_2$).

However, multiparticulate segments are less preferred than monolithic segments and oligoparticulate segments.

In a preferred embodiment, the pharmaceutical dosage form contains a single, monolithic formed segment ($S_1$), or a multitude of particulate formed segments ($S_1$).

In a particularly preferred embodiment, monolithic or particulate formed segment(s) ($S_1$) and/or further segment(s) ($S_2$) of the pharmaceutical dosage form each has/have an extension in any given direction of at least 2.0 mm, more preferably at least 2.2 mm, still more preferably at least 2.5 mm, yet more preferably at least 2.8 mm, even more preferably at least 3.0 mm, most preferably at least 3.2 mm, and in particular at least 3.5 mm or 4.0 mm. According to this embodiment, the monolithic or particulate formed segment(s) ($S_1$) and/or further segment(s) ($S_2$) particularly preferably each have an extension in any given direction of at least 2.0 mm or 3.0 mm and have a weight of at least 20 mg.

Particularly preferably, the pharmaceutical dosage form contains a single, monolithic formed segment ($S_1$) having an extension in any direction of at least 2.0 mm; or a multitude of particulate formed segments ($S_1$) each having an extension in any direction of at least 2.0 mm.

For the purpose of specification, "in any direction" preferably means in every direction in the three-dimensional space.

The size of the particles or the monolith may be determined by any conventional procedure known in the art, e.g. laser light scattering, sieve analysis, light microscopy or image analysis.

The shape of the particles and/or monoliths, i.e. the shape of the formed segment(s) ($S_1$) and/or the further segment(s) ($S_2$), is not particularly limited. Preferably, the particles and/or the monolith are essentially cylindrical in shape, e.g. cut extruded rods. The diameter of such particles and/or monolith is therefore the diameter of their circular cross section. The cylindrical shape can be caused by hot-melt extrusion according to which the diameter of the circular cross section is a function of the extrusion die and the length of the cylinders is a function of the cutting length according to which the extruded strand of material is cut into pieces of preferably more or less predetermined length.

The segment ($S_1$) is "formed". In this regard, the term "formed" refers to any measure providing the material of segment ($S_1$) with a predetermined or arbitrary outer shape. Forming may but does not need to be achieved by means of a die. Preferably, formed segment ($S_1$) is thermoformed. For example, extruding a heated material, e.g. by means of hot-melt extrusion, and subsequently cutting the extruded strand into segments of predetermined length provides formed segments ($S_1$) according to the invention.

In a preferred embodiment, the formed segment(s) ($S_1$) and/or the further segment(s) ($S_2$) is/are not film coated.

In another preferred embodiment, the formed segment(s) ($S_1$) and/or the further segment(s) ($S_2$) is/are film coated. The formed segment(s) ($S_1$) and/or the further segment(s) ($S_2$) according to the invention can optionally be provided, partially or completely, with a conventional coating. The formed segment(s) ($S_1$) and/or the further segment(s) ($S_2$) are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinyl alcohol-polyethylene glycol graft copolymers, polyvinylacetate; and natural film formers.

The coating material may contain excipients such as stabilizers (e.g. surfactants such as macrogol cetostearylether, sodium dodecylsulfate, and the like). Suitable excipients of film coating materials are known to the skilled person.

In a particularly preferred embodiment, the coating is water-soluble.

Though less preferred, the coating can principally be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

A particularly preferred coating contains polyvinyl alcohol and optionally, further excipients such as xanthan gum and/or talcum.

For the purpose of specification, the term "pharmacologically active ingredient" as used herein may refer to either one or more pharmacologically active ingredients, i.e. the terms "first pharmacologically ingredient ($A_1$)" and "second pharmacologically ingredient ($A_2$)" may each refer to a single pharmacologically active ingredient or a combination of one or more pharmacologically active ingredients.

There are generally no limitations as to the pharmacologically active ingredient (pharmacologically active compound) which can be incorporated in the segments of the pharmaceutical dosage form according to the invention. Furthermore, the term "pharmacologically active ingredient" preferably includes any physiologically acceptable salt, e.g. physiologically acceptable acid addition salt, of the base form of the pharmacologically active ingredient. Physiologically acceptable acid addition salts comprise any acid addition salts which can conveniently be obtained by treating the base form of a pharmacologically active ingredient with appropriate organic and inorganic acids. Pharmacologically active ingredients containing an acidic proton may be converted into their non-toxic metal or amine addition salt forms by treatment with appropriate organic and inorganic bases. The term addition salt also comprises the hydrates and solvent addition forms which a pharmacologically active ingredient is able to form. Examples of such forms are e.g. hydrates, alcoholates and the like.

Unless explicitly stated otherwise, all amounts of the first pharmacologically active ingredient ($A_1$) and the second pharmacologically active ingredient ($A_2$) specified in the following are given according to the corresponding amount of the free compound.

Preferably, the first pharmacologically active ingredient ($A_1$) is an opioid and the second pharmacologically active ingredient ($A_2$) is another analgesic, but preferably no opioid, e.g. paracetamol (acetaminophen), an NSAID or COX-2-inhibitor.

In a particularly preferred embodiment, the first pharmacologically active ingredient ($A_1$) is hydrocodone or a physiologically acceptable salt thereof and the second pharmacologically active ingredient ($A_2$) is paracetamol.

In a preferred embodiment, the first pharmacologically active ingredient ($A_1$) and the second pharmacologically active ingredient ($A_2$) are spatially separated from one another. According to this embodiment, the formed segment ($S_1$) preferably contains less than 0.1 ppm, more preferably less than 0.01 ppm, most preferably less than 0.001 ppm and in particular less than 0.0001 ppm of the second pharmacologically active ingredient ($A_2$). Further, according to this embodiment, the further segment ($S_2$) preferably contains less than 0.1 ppm, more preferably less than 0.01 ppm, most preferably less than 0.001 ppm and in particular less than 0.0001 ppm of the first pharmacologically active ingredient ($A_1$). In a particularly preferred embodiment, the formed segment ($S_1$) contains no second pharmacologically active ingredient ($A_2$) and the further segment ($S_2$) contains no first pharmacologically active ingredient ($A_1$).

Preferably, at least 99 wt.-%, more preferably at least 99.9 wt.-%, most preferably at least 99.99 wt.-% and in particular at least 99.999 wt.-% of the total amount of the first pharmacologically active ingredient ($A_1$) contained in the pharmaceutical dosage form are contained in the formed segment ($S_1$).

Preferably, at least 99 wt.-%, more preferably at least 99.9 wt.-%, most preferably at least 99.99 wt.-% and in particular at least 99.999 wt.-% of the total amount of the second pharmacologically active ingredient ($A_2$) contained in the pharmaceutical dosage form are contained in the further segment ($S_2$).

The term "prolonged release" is known to the skilled artisan. For the purpose of specification, the term "prolonged release" preferably refers to a release rate of the pharmacologically active ingredient from the formulation that has been reduced over time in order to maintain therapeutic activity, to reduce toxic effects, or for some other therapeutic purpose such as reducing the dosing frequency.

The term "immediate release" is known to the skilled artisan. For the purpose of specification, the term "immediate release" preferably refers to a release rate of the pharmacologically active ingredient from the formulation that is comparatively fast and not retarded.

Figure 1:
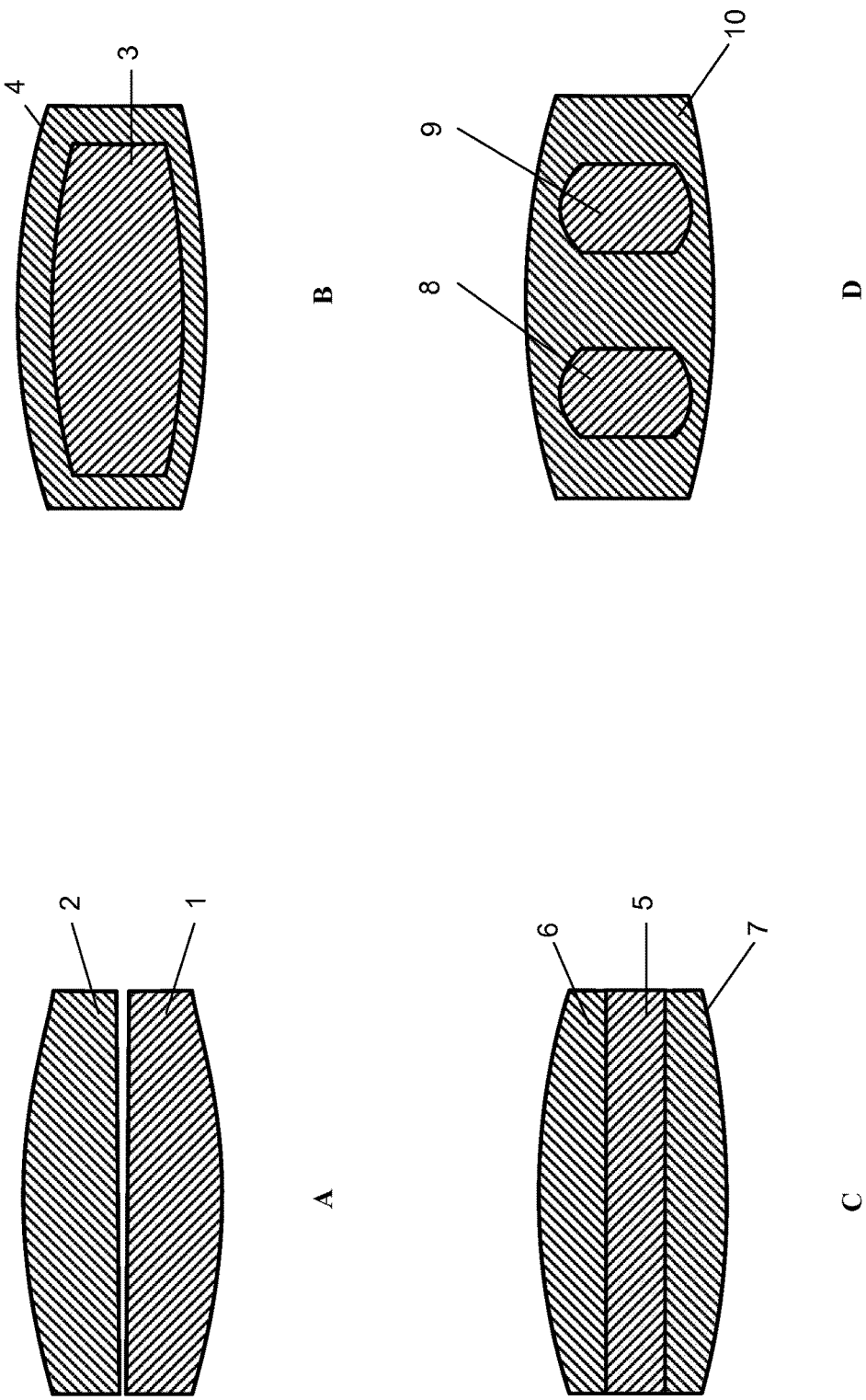
FIG. 1A schematically illustrates a two-layer tablet comprising a formed segment (S$_1$) as first layer (1) and a further segment (S$_2$) as second layer (2).
FIG. 1B schematically illustrates a mantle tablet comprising a formed segment (S$_1$) as a core (3) and a further segment (S$_2$) (4) surrounding said core (3).
FIG. 1C schematically illustrates a three-layer tablet comprising a formed segment (S$_1$) as first layer (5) and two further segments (S$_2$) as layer (6) and layer (7).
FIG. 1D schematically illustrates a multicomponent tablet comprising two formed segments (S$_1$) (8) and (9) that are embedded and form a discontinuous phase in a further segment (S$_2$) forming a matrix (10).

Preferably, when the formed segment(s) ($S_1$) and/or the further segment(s) ($S_2$) are particulate, the pharmaceutical dosage form according to the invention comprises the particles as a discontinuous phase, i.e. the particles form a discontinuous phase in an outer matrix material which in turn preferably forms a continuous phase (cf. FIG. 1D). In this regard, discontinuous means that not each and every particle is in intimate contact with another particle but that the particles are at least partially separated from one another by the outer matrix material in which the particles are embedded. In other words, the particles preferably do not form a single coherent mass within the pharmaceutical dosage forms according to the invention (multicomponent tablet).

In a preferred embodiment, the further segment(s) ($S_2$) form(s) an outer matrix material in which the formed segment(s) ($S_1$) is/are embedded. According to this embodiment, the pharmaceutical dosage form according to the invention can preferably be a MUPS formulation (multiple unit pellet system) or a capsule.

Preferably, the formed segment(s) ($S_1$) and the further segment(s) ($S_2$) have different morphology and properties, more preferably the formed segment ($S_1$) is monolithic or particulate and the further segment ($S_2$) forms the outer matrix material. When the formed segments ($S_1$) are particulate, the particles preferably form a discontinuous phase within the outer matrix material formed by the further segment ($S_2$) (cf. FIG. 1D) (multicomponent tablet). When the formed segment ($S_1$) contains a prolonged release matrix material, the outer matrix material is to be distinguished from said prolonged release matrix material, since the outer matrix material preferably does not provide for a prolonged release.

When the formed segment ($S_1$) is monolithic or particulate and the further segment ($S_2$) forms the outer matrix material, the pharmaceutical dosage form according to the invention preferably is in form of a capsule, i.e. a soft capsule or a hard capsule.

The formed segment(s) ($S_1$) typically has/have mechanical properties that differ from the mechanical properties of the outer matrix material. Preferably, the formed segment(s) ($S_1$) has/have a higher mechanical strength than the outer matrix material. The formed segment(s) ($S_1$) can preferably be visualized by conventional means such as solid state nuclear magnetic resonance spectroscopy, scanning electron microscopy, terahertz spectroscopy and the like.

In a further preferred embodiment, the formed segment ($S_1$) and/or the further segment ($S_2$) constitute a spatially confined area within the pharmaceutical dosage form. According to this embodiment, the formed segment ($S_1$) and/or further segment ($S_2$) preferably form a layer, a coating, a core or a mantle of the pharmaceutical dosage form.

When the formed segment ($S_1$) and/or further segment ($S_2$) forms a layer, the pharmaceutical dosage form preferably is in form of a layered tablet (cf. FIG. 1A and FIG. 1C).

The formed segment ($S_1$) or the further segment ($S_2$) may also form the coating of the pharmaceutical dosage form. Preferably, the formed segment ($S_1$) forms the core of the pharmaceutical dosage form that is coated by the further segment ($S_2$). Preferably, however, neither the formed segment ($S_1$) nor the further segment ($S_2$) forms a coating of the pharmaceutical dosage form, particularly no spray coating. Rather, the first segment ($S_1$) and the further segment ($S_2$) are preferably both coated by another material such as a sugar coating.

In a preferred embodiment, the pharmaceutical dosage form is in form of a mantle tablet (cf. FIG. 1B). According to this embodiment, the formed segment ($S_1$) preferably forms the core and the further segment ($S_2$) preferably forms the mantle.

In a preferred embodiment, the pharmaceutical dosage form according to the invention is a tablet, which comprises (i) a single formed segment ($S_1$) and a single further segment ($S_2$) that are arranged to form a bilayer tablet (cf. FIG. 1A);

(ii) a single formed segment ($S_1$) forming a core that is surrounded by a single further segment ($S_2$) such that formed segment ($S_1$) and further segment ($S_2$) are arranged to form a mantle tablet (cf. FIG. 1B);

(iii) a single formed segment ($S_1$) and two further segments ($S_2$) that are arranged to form a trilayer tablet, wherein formed segment ($S_1$) forms the middle layer and the two further segments ($S_2$) form the outer layers (cf. FIG. 1C);

(iv) a plurality of formed segments ($S_1$) and a plurality of further segments ($S_2$) that are arranged to form a multilayer tablet, wherein preferably each of the formed segments ($S_1$) is arranged in between two adjacent further segments ($S_2$);

(v) a plurality of formed segments ($S_1$) which form a discontinuous phase embedded in further segment ($S_2$) which forms a matrix (cf. FIG. 1D) (multicomponent tablet); or (vi) a single formed segment ($S_1$) and one or more further segments ($S_2$) that are together coated by a sugar coating thus forming a sugar-coated tablet (dragée).

In another preferred embodiment, the pharmaceutical dosage form according to the invention is a capsule, which is filled with (i) a single formed segment ($S_1$) and a single further segment ($S_2$), which can optionally be present in form of a monolith or in form of a powdery material (cf. FIG. 2A);

(ii) a single formed segment ($S_1$) and a plurality of further segments ($S_2$) (cf. FIG. 2B);

(iii) a plurality of formed segments ($S_1$) and a single further segment ($S_2$), which can optionally be present in form of a monolith or in form of a powdery material (cf. FIG. 2F); or (iv) a plurality of formed segments ($S_1$) and a plurality of further segment ($S_2$) (cf. FIGS. 2C, D and E).

The pharmaceutical dosage form comprises a formed segment ($S_1$), which contains a first pharmacologically active ingredient ($A_1$) and provides prolonged release thereof.

In a preferred embodiment, the first pharmacologically active ingredient ($A_1$) is only a single pharmacologically active ingredient. In another preferred embodiment, the first pharmacologically active ingredient ($A_1$) is a combination of two or more pharmacologically active ingredients.

Preferably, the first pharmacologically active ingredient ($A_1$) has potential for being abused. Pharmacologically active ingredients with potential for being abused are known to the person skilled in the art and comprise e.g. tranquillizers, stimulants, barbiturates, narcotics, opioids or opioid derivatives.

Preferably, the first pharmacologically active ingredient ($A_1$) has a psychotropic effect, i.e. crosses the blood-brain barrier and acts primarily upon the central nervous system where it affects brain function, resulting in alterations in perception, mood, consciousness, cognition, and behavior.

Preferably, the first pharmacologically active ingredient ($A_1$) is selected from the group consisting of opioids, stimulants, tranquilizers, and other narcotics.

Particularly preferably, the first pharmacologically active ingredient ($A_1$) is an opioid or a physiologically acceptable salt thereof. According to the Anatomical Therapeutic Chemical (ATC) classification system by WHO (ATC index), opioids are divided into natural opium alkaloids, phenylpiperidine derivatives, diphenylpropylamine derivatives, benzomorphan derivatives, oripavine derivatives, morphinan derivatives and others. Preferably, the second pharmacologically active ingredient ($A_2$) is selected from ATC classes [M01A], [M01C], [N02B] and [N02C] according to the WHO.

The following opioids, tranquillizers or other narcotics are substances with a psychotropic action, i.e. have a potential of abuse, and hence are preferably contained in the formed segment ($S_1$) of the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethyl-thiambutene, dioxaphetylbutyrate, dipipanone, dronabinol, eptazocine, estazolam, etho-heptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, Papaver somniferum, papavereturn, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl) propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl) cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3 (3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl) propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the formed segment ($S_1$) contains an opioid selected from the group consisting of DPI-125, M6G (CE-04-410), ADL-5859, CR-665, NRP290 and sebacoyl dinalbuphine ester.

In a preferred embodiment, the formed segment ($S_1$) contains the first pharmacologically active ingredient ($A_1$) which is one pharmacologically active ingredient or more pharmacologically active ingredients selected from the group consisting of oxycodone, oxymorphone, hydromorphone, hydrocodone, morphine, tapentadol, tramadol, buprenorphine, and the physiologically acceptable salts thereof.

In another preferred embodiment, the first pharmacologically active ingredient ($A_1$) is selected from the group consisting of tapentadol, faxeladol, axomadol and the physiologically acceptable salts thereof.

In still another preferred embodiment, the first pharmacologically active ingredient ($A_1$) is selected from the group consisting of 1,1-(3-dimethylamino-3-phenylpentamethylene)-6-fluoro-1,3,4,9-tetrahydropyrano[3,4-b]indole (cebranopadol), particularly its hemicitrate; 1,1-[3-dimethylamino-3-(2-thienyl)pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

The first pharmacologically active ingredient ($A_1$) is present in the pharmaceutical dosage form in a therapeutically effective amount. In general, the amount that constitutes a therapeutically effective amount varies according to the pharmacologically active ingredients being used, the condition being treated, the severity of said condition, the patient being treated, and whether the pharmaceutical dosage form or the segment in which the pharmacologically active ingredient is contained is designed for an immediate or retarded release.

The content of the first pharmacologically active ingredient ($A_1$) preferably ranges from about 0.01 wt.-% to about 95 wt.-%, more preferably from about 0.1 wt.-% to about 80 wt.-%, even more preferably from about 1.0 wt.-% to about 50 wt.-%, yet more preferably from about 1.5 wt.-% to about 30 wt.-%, and most preferably from about 2.0 wt.-% to 20 wt.-%, based on the total weight of the formed segment(s) ($S_1$) or based on the total weight of the pharmaceutical dosage form.

Preferably, the content of the first pharmacologically active ingredient ($A_1$) is within the range of from 0.01 to 80 wt.-%, more preferably 0.1 to 50 wt.-%, still more preferably 1 to 25 wt.-%, based on the total weight of the pharmaceutical dosage form. In a preferred embodiment, the content of the first pharmacologically active ingredient ($A_1$) is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In another preferred embodiment, the content of the first pharmacologically active ingredient ($A_1$) is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of the first pharmacologically active ingredient ($A_1$) is within the range of from 20±6 wt.-%, more preferably 20±5 wt.-%, still more preferably 20±4 wt.-%, more preferably 20±3 wt.-%, most preferably 20±3 wt.-%, and in particular 20±2 wt.-%, based on the total weight of the pharmaceutical dosage form.

Preferably, the content of the first pharmacologically active ingredient ($A_1$) is within the range of from 0.01 to 80 wt.-%, more preferably 0.1 to 60 wt.-%, still more preferably 5 to 50 wt.-%, based on the total weight of the formed segment(s) ($S_1$). In a preferred embodiment, the content of the first pharmacologically active ingredient ($A_1$) is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the formed segment(s) ($S_1$). In another preferred embodiment, the content of the first pharmacologically active ingredient ($A_1$) is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the formed segment(s) ($S_1$). In a further preferred embodiment, the content of the first pharmacologically active ingredient ($A_1$) is within the range of from 20±6 wt.-%, 25±6 wt.-% or 30±6 wt.-%, more preferably 20±5 wt.-%, 25±5 wt.-% or 30±5 wt.-%, still more preferably 20±4 wt.-%, 25±4 wt.-% or 30±4 wt.-%, most preferably 20±3 wt.-%, 25±3 wt.-% or 30±3 wt.-% and in particular 20±2 wt.-%, 25±2 wt.-% or 30±2 wt.-%, based on the total weight of the formed segment(s) ($S_1$).

The total dose of the first pharmacologically active ingredient ($A_1$) in the formed segment ($S_1$) and the pharmaceutical dosage form, respectively, is not limited. The dose of the first pharmacologically active ingredient ($A_1$) which is adapted for administration preferably is in the range of 0.01 mg to 2,000 mg or 0.01 mg to 1,000 mg or 0.1 mg to 500 mg, more preferably in the range of 1.0 mg to 400 mg, even more preferably in the range of 1.0 mg to 10.0 mg or 5.0 mg to 300 mg, and most preferably in the range of 1.5 mg to 8 mg or 10 mg to 250 mg. In a preferred embodiment, the total amount of the first pharmacologically active ingredient ($A_1$) which is contained in the formed segment ($S_1$) and the pharmaceutical dosage form, respectively, is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg. In another preferred embodiment, the total amount of the first pharmacologically active ingredient ($A_1$) which is contained in the formed segment ($S_1$) and the pharmaceutical dosage form, respectively, is within the range of from 10 to 500 mg, more preferably 12 to 450 mg, still more preferably 14 to 400 mg, yet more preferably 16 to 350 mg, most preferably 18 to 325 mg and in particular 20 to 300 mg.

In a preferred embodiment, the first pharmacologically active ingredient ($A_1$) is contained in the formed segment(s) ($S_1$) and the pharmaceutical dosage form, respectively, in a total amount of 10±5 µg, 20±5 µg, 30±5 µg, 40±5 µg, 50±5 µg, 60±5 µg, 70±5 µg, 80±5 µg, 90±5 µg, 100±5 µg, 125±25 µg, 150±25 µg, 175±25 µg, 200±25 µg, 250±50 µg, 300±50 µg, 350±50 µg, 400±50 µg, 450±50 µg, 500±50 µg, 550±50 µg, 600±50 µg, 650±50 µg, 700±50 µg, 750±50 µg, 800±50 µg, 850±50 µg, 900±50 µg, 950±50 µg, or 1000±50 µg. In another preferred embodiment, the first pharmacologically active ingredient ($A_1$) is contained in the formed segment(s)

($S_1$) and the pharmaceutical dosage form, respectively, in a total amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, or 250±5 mg. In another preferred embodiment, the first pharmacologically active ingredient ($A_1$) is contained in the formed segment ($S_1$) and the pharmaceutical dosage form, respectively, in a total amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, or 250±2.5 mg. In still another preferred embodiment, the first pharmacologically active ingredient ($A_1$) is contained in the formed segment(s) ($S_1$) and the pharmaceutical dosage form, respectively, in a total amount of 250±10 mg, 275±10 mg, 300±10 mg, 325±10 mg, 350±10 mg, 375±10 mg, 400±10 mg, 425±10 mg, 450±10 mg, 475±10 mg, 500±10 mg, 525±10 mg, 550±10 mg, 575±10 mg or 600±10 mg.

In a particularly preferred embodiment, the first pharmacologically active ingredient ($A_1$) is oxycodone, preferably its HCl salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 1 to 80 mg. In another particularly preferred embodiment, the first pharmacologically active ingredient ($A_1$) is oxycodone, preferably its HCl salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 2 to 320 mg.

In another particularly preferred embodiment, the first pharmacologically active ingredient ($A_1$) is oxymorphone, preferably its HCl salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 5 to 40 mg. In another particularly preferred embodiment, the first pharmacologically active ingredient ($A_1$) is oxymorphone, preferably its HCl salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 10 to 80 mg.

In another particularly preferred embodiment, the first pharmacologically active ingredient ($A_1$) is tapentadol, preferably its HCl salt, and the pharmaceutical dosage form is adapted for administration once daily or twice daily. In this embodiment, the first pharmacologically active ingredient ($A_1$) is preferably contained in the formed segment(s) ($S_1$) and the pharmaceutical dosage form, respectively, in a total amount of from 25 to 250 mg.

In still another particularly preferred embodiment, the first pharmacologically active ingredient ($A_1$) is hydromorphone, preferably its HCl salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 2 to 52 mg. In another particularly preferred embodiment, the first pharmacologically active ingredient ($A_1$) is hydromorphone, preferably its HCl salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 4 to 104 mg.

In yet another particularly preferred embodiment, the first pharmacologically active ingredient ($A_1$) is tramadol, preferably its HCl salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 5 to 300 mg. In another particularly preferred embodiment, the first pharmacologically active ingredient ($A_1$) is tramadol, preferably its HCl salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 10 to 500 mg.

In another particularly preferred embodiment, the first pharmacologically active ingredient ($A_1$) is hydrocodone, preferably its HCl salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 5 to 250 mg. In another particularly preferred embodiment, the first pharmacologically active ingredient ($A_1$) is hydrocodone, preferably its HCl salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 5 to 250 mg.

In still another particularly preferred embodiment, the first pharmacologically active ingredient ($A_1$) is morphine, preferably its HCl or $H_2SO_4$ salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 5 to 250 mg.

In another particularly preferred embodiment, the first pharmacologically active ingredient ($A_1$) is morphine, preferably its HCl or $H_2SO_4$ salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 5 to 250 mg.

In another particularly preferred embodiment, the first pharmacologically active ingredient ($A_1$) is buprenorphine, preferably its HCl salt, and the pharmaceutical dosage form is adapted for administration twice daily. In this embodiment, the first pharmacologically active ingredient ($A_1$) is preferably contained in the formed segment(s) ($S_1$) and the pharmaceutical dosage form, respectively, in a total amount of from 1 to 12 mg. In another particularly preferred embodiment, the first pharmacologically active ingredient ($A_1$) is buprenorphine, preferably its HCl salt, and the pharmaceutical dosage form is adapted for administration once daily. In this embodiment, the first pharmacologically active ingredient ($A_1$) is preferably contained in the formed segment(s) ($S_1$) and the pharmaceutical dosage form, respectively, in a total amount of from 2 to 12 mg.

The first pharmacologically active ingredient ($A_1$) that is employed in the preparation of the formed segment(s) ($S_1$) preferably has an average particle size of less than 500 microns, still more preferably less than 300 microns, yet more preferably less than 200 or 100 microns. There is no lower limit on the average particle size and it may be, for example, 50 microns. The particle size of pharmacologically active ingredients may be determined by any technique conventional in the art, e.g. laser light scattering, sieve analysis, light microscopy or image analysis.

The formed segment(s) ($S_1$) provide prolonged release of the first pharmacologically active ingredient ($A_1$). While such prolonged release may principally be achieved by providing the formed segment(s) ($S_1$) with a prolonged release coating containing pore formers, prolonged release is preferably achieved by a prolonged release matrix.

Thus, the formed segment(s) ($S_1$) preferably comprise(s) a prolonged release matrix. The prolonged release matrix in turn preferably comprises a prolonged release matrix material that serves the function of providing prolonged release of the first pharmacologically active ingredient ($A_1$), optionally further pharmaceutical excipients that do not substantially influence the release profile, and the first pharmacologically active ingredient ($A_1$).

The first pharmacologically active ingredient ($A_1$) is preferably embedded, particularly preferably dispersed in the prolonged release matrix material.

The total content of the prolonged release matrix (first pharmacologically active ingredient ($A_1$)+prolonged release matrix material+optionally present excipients that do not substantially influence the release profile) that is contained in the formed segment(s) ($S_1$) is preferably at least 30 wt.-%, more preferably at least 40 wt.-%, still more preferably at least 50 wt.-%, yet more preferably at least 60 wt.-%, even more preferably at least 70 wt.-%, most preferably at least 80 wt.-%, and in particular at least 90 wt.-%, relative to the total weight of the formed segment(s) ($S_1$).

The total content of the prolonged release matrix (first pharmacologically active ingredient ($A_1$)+prolonged release matrix material+optionally present excipients that do not substantially influence the release profile) that is contained in the formed segment(s) ($S_1$) is preferably within the range of from 5 to 95 wt.-%, more preferably 7 to 90 wt.-%, still more preferably 9 to 80 wt.-%, yet more preferably 11 to 70 wt.-%, even more preferably 13 to 60 wt.-%, most preferably 14 to 50 wt.-%, and in particular 15 to 40 wt.-%, relative to the total weight of the pharmaceutical dosage form.

Preferably, the first pharmacologically active ingredient ($A_1$) and the prolonged release matrix material are intimately homogeneously distributed within the formed segment(s) ($S_1$) so that the formed segment(s) ($S_1$) do(es) not contain any portions where either the first pharmacologically active ingredient ($A_1$) is present in the absence of prolonged release matrix material or where prolonged release matrix material is present in the absence of the first pharmacologically active ingredient ($A_1$).

When the formed segment ($S_1$) is film coated, the prolonged release matrix material is preferably homogeneously distributed in the body of the formed segment ($S_1$), i.e. the film coating preferably does not contain prolonged release matrix material.

Apart from the prolonged release matrix material, the formed segment(s) ($S_1$) preferably contain(s) conventional pharmaceutical excipients that do not substantially influence the release profile.

Preferably, the total content of the prolonged release matrix material, i.e. material that serves the function of providing prolonged release of the first pharmacologically active ingredient ($A_1$), is within the range of from 20 to 99 wt.-%, relative to the total weight of the formed segment(s) ($S_1$). When the formed segments ($S_1$) are particulate, these percent values preferably are related to the total weight of all particles of the formed segment(s) ($S_1$).

In a preferred embodiment, the content of the prolonged release matrix material is at least 5 wt.-%, or at least 10 wt.-%, or at least 15 wt.-%, more preferably at least 20 wt.-%, or at least 25 wt.-%, or at least 30 wt.-%, still more preferably at least 35 wt.-%, or at least 40 wt.-%, or at least 45 wt.-%, yet more preferably at least 50 wt.-%, or at least 55 wt.-%, or at least 60 wt.-%, most preferably at least 65 wt.-%, or at least 70 wt.-%, or at least 75 wt.-%, and in particular at least 80 wt.-%, or at least 85 wt.-%, or at least 90 wt.-%, based on the total weight of the formed segment(s) ($S_1$).

In a preferred embodiment, the total content of prolonged release matrix material is within the range of 25±20 wt.-%, more preferably 25±15 wt.-%, most preferably 25±10 wt.-%, and in particular 25±5 wt.-%, based on the total weight of the formed segment(s) ($S_1$).

In another preferred embodiment, the total content of prolonged release matrix material is within the range of 30±20 wt.-%, more preferably 30±15 wt.-%, most preferably 30±10 wt.-%, and in particular 30±5 wt.-%, based on the total weight of the formed segment(s) ($S_1$).

In still another preferred embodiment, the total content of prolonged release matrix material is within the range of 35±20 wt.-%, more preferably 35±15 wt.-%, most preferably 35±10 wt.-%, and in particular 35±5 wt.-%, based on the total weight of the formed segment(s) ($S_1$).

In a yet another preferred embodiment, the total content of prolonged release matrix material is within the range of 40±20 wt.-%, more preferably 40±15 wt.-%, and most preferably 40±10 wt.-%, and in particular 40±5 wt.-%, based on the total weight of the formed segment(s) ($S_1$).

In a further preferred embodiment, the total content of prolonged release matrix material is within the range of 45±20 wt.-%, more preferably 45±15 wt.-%, and most preferably 45±10 wt.-%, and in particular 45±5 wt.-%, based on the total weight of the formed segment(s) ($S_1$).

In still a further preferred embodiment, the total content of prolonged release matrix material is within the range of 50±20 wt.-%, more preferably 50±15 wt.-%, and most preferably 50±10 wt.-%, and in particular 50±5 wt.-%, based on the total weight of the formed segment(s) ($S_1$).

In yet a further preferred embodiment, the total content of prolonged release matrix material is within the range of 55±20 wt.-%, more preferably 55±15 wt.-%, and most preferably 55±10 wt.-%, and in particular 55±5 wt.-%, based on the total weight of the formed segment(s) ($S_1$).

In another preferred embodiment, the total content of prolonged release matrix material is within the range of 60±20 wt.-%, more preferably 60±15 wt.-%, and most preferably 60±10 wt.-%, and in particular 60±5 wt.-%, based on the total weight of the formed segment(s) ($S_1$).

In still another preferred embodiment, the total content of prolonged release matrix is within the range of 65±20 wt.-%, more preferably 65±15 wt.-%, and most preferably 65±10 wt.-%, and in particular 65±5 wt.-%, based on the total weight of the formed segment(s) ($S_1$).

In yet another preferred embodiment, the total content of prolonged release matrix material is within the range of 70±20 wt.-%, more preferably 70±15 wt.-%, and most preferably 70±10 wt.-%, and in particular 70±5 wt.-%, based on the total weight of the formed segment(s) ($S_1$).

In a further preferred embodiment, the total content of prolonged release matrix material is within the range of 75±20 wt.-%, more preferably 75±15 wt.-%, and most preferably 75±10 wt.-%, and in particular 75±5 wt.-%, based on the total weight of the formed segment(s) ($S_1$).

In still a further preferred embodiment, the total content of prolonged release matrix material is within the range of 80±15 wt.-%, more preferably 80±12 wt.-%, and most preferably 80±10 wt.-%, and in particular 80±5 wt.-%, based on the total weight of the formed segment(s) ($S_1$).

In yet a further preferred embodiment, the total content of prolonged release matrix material is within the range of 85±10 wt.-%, more preferably 85±8 wt.-%, and most preferably 85±6 wt.-%, and in particular 85±4 wt.-%, based on the total weight of the formed segment(s) ($S_1$).

In another preferred embodiment, the total content of prolonged release matrix material is within the range of 90±8 wt.-%, more preferably 90±7 wt.-%, and most preferably 90±6 wt.-%, and in particular 90±4 wt.-%, based on the total weight of the formed segment(s) ($S_1$).

In still another preferred embodiment, the total content of prolonged release matrix material is within the range of 95±3 wt.-%, more preferably 95±2 wt.-%, and most preferably 95±1 wt.-%, and in particular 95±0.5 wt.-%, based on the total weight of the formed segment(s) ($S_1$).

Preferably, the total content of the prolonged release matrix material, i.e. material that serves the function of providing prolonged release of the first pharmacologically active ingredient ($A_1$), contained in the formed segment(s) ($S_1$) is within the range of from 5 to 95 wt.-%, more preferably 15 to 80 wt.-% or 20 to 80 wt.-% relative to the total weight of the pharmaceutical dosage form.

In a preferred embodiment, the content of the prolonged release matrix material is at least 5 wt.-% or at least 10 wt.-%, more preferably at least 15 wt.-%, still more preferably at least 20 wt.-%, yet more preferably at least 25 wt.-% and in particular at least 30 wt.-%, or at least 35 wt.-%, or at least 40 wt.-%, or at least 45 wt.-%, or at least 50 wt.-%, or at least 55 wt.-%, or at least 60 wt.-%, based on the total weight of the pharmaceutical dosage form.

In still another preferred embodiment, the total content of prolonged release matrix material is within the range of 20±16 wt.-%, more preferably 20±12 wt.-%, most preferably 20±8 wt.-%, and in particular 20±4 wt.-%, based on the total weight of the pharmaceutical dosage form.

In yet another preferred embodiment, the total content of prolonged release matrix material is within the range of 25±20 wt.-%, more preferably 25±15 wt.-%, most preferably 25±10 wt.-%, and in particular 25±5 wt.-%, based on the total weight of the pharmaceutical dosage form.

In a further preferred embodiment, the total content of prolonged release matrix material is within the range of 30±20 wt.-%, more preferably 30±15 wt.-%, most preferably 30±10 wt.-%, and in particular 30±5 wt.-%, based on the total weight of the pharmaceutical dosage form.

In still a further preferred embodiment, the total content of prolonged release matrix material is within the range of 35±20 wt.-%, more preferably 35±15 wt.-%, most preferably 35±10 wt.-%, and in particular 35±5 wt.-%, based on the total weight of the pharmaceutical dosage form.

In a still further preferred embodiment, the total content of prolonged release matrix material is within the range of 40±20 wt.-%, more preferably 40±15 wt.-%, and most preferably 40±10 wt.-%, and in particular 40±5 wt.-%, based on the total weight of the pharmaceutical dosage form.

In a yet further preferred embodiment, the total content of prolonged release matrix material is within the range of 45±20 wt.-%, more preferably 45±15 wt.-%, and most preferably 45±10 wt.-%, and in particular 45±5 wt.-%, based on the total weight of the pharmaceutical dosage form.

In another preferred embodiment, the total content of prolonged release matrix material is within the range of 50±20 wt.-%, more preferably 50±15 wt.-%, and most preferably 50±10 wt.-%, and in particular 50±5 wt.-%, based on the total weight of the pharmaceutical dosage form.

In a yet further preferred embodiment, the total content of prolonged release matrix material is within the range of 55±20 wt.-%, more preferably 55±15 wt.-%, and most preferably 55±10 wt.-%, and in particular 55±5 wt.-%, based on the total weight of the pharmaceutical dosage form.

In another preferred embodiment, the total content of prolonged release matrix material is within the range of 60±20 wt.-%, more preferably 60±15 wt.-%, and most preferably 60±10 wt.-%, and in particular 60±5 wt.-%, based on the total weight of the pharmaceutical dosage form.

In still another preferred embodiment, the total content of prolonged release matrix material is within the range of 65±20 wt.-%, more preferably 65±15 wt.-%, and most preferably 65±10 wt.-%, and in particular 65±5 wt.-%, based on the total weight of the pharmaceutical dosage form.

Preferably, the relative weight ratio of the prolonged release matrix material, i.e. material that serves the function of providing prolonged release of the first pharmacologically active ingredient ($A_1$), to the first pharmacologically active ingredient ($A_1$) is within the range of from 40:1 to 1:40 or 35:1 to 1:35 or 30:1 to 1:30 or 20:1 to 1:20, more preferably 15:1 to 1:15, still more preferably 10:1 to 1:10, yet more preferably 7:1 to 1:7, most preferably 5:1 to 1:5, and in particular 2:1 to 1:2.

The prolonged release matrix material, i.e. material that serves the function of providing prolonged release of the first pharmacologically active ingredient ($A_1$), preferably comprises at least one synthetic or natural polymer (C) and/or optionally a waxy material. Preferably, the prolonged release matrix material comprises only one synthetic or natural polymer (C). In a preferred embodiment, the prolonged release matrix material consists of synthetic or natural polymer (C).

In a preferred embodiment, the first pharmacologically active ingredient ($A_1$) is embedded in a prolonged release matrix comprising a synthetic or natural polymer (C).

The total content of the synthetic or natural polymer (C) is preferably at least 65 wt.-%, more preferably at least 70 wt.-%, still more preferably at least 75 wt.-%, yet more preferably at least 80 wt.-%, even more preferably at least 85 wt.-%, most preferably at least 90 wt.-%, and in particular at least 95 wt.-%, relative to the total weight of the prolonged release matrix material, i.e. material that serves the function of providing prolonged release of the first pharmacologically active ingredient ($A_1$).

The total content of the synthetic or natural polymer (C) is preferably at least 20 wt.-%, more preferably at least 30 wt.-%, still more preferably at least 40 wt.-%, yet more preferably at least 50 wt.-%, even more preferably at least 60 wt.-%, most preferably at least 70 wt.-%, and in particular at least 80 wt.-%, relative to the total weight of the prolonged release matrix (first pharmacologically active ingredient ($A_1$)+prolonged release matrix material+optionally present excipients that do not substantially influence the release profile).

Preferably, the total content of the synthetic or natural polymer (C) is at least 20 wt.-%, more preferably at least 30 wt.-%, still more preferably at least 40 wt.-%, yet more preferably at least 50 wt.-%, even more preferably at least 60 wt.-%, most preferably at least 70 wt.-%, and in particular at least 80 wt.-%, relative to the total weight of the formed segment(s) ($S_1$).

In a preferred embodiment, the total content of the synthetic or natural polymer (C) is at least 5 wt.-%, more preferably at least 10 wt.-%, still more preferably at least 15 wt.-%, yet more preferably at least 20 wt.-% and in particular at least 25 wt.-%, relative to the total weight of the formed segment(s) ($S_1$). In a particularly preferred embodiment, the content of the synthetic or natural polymer (C) is at least 30 wt.-% relative to the total weight of the formed segment(s) ($S_1$).

In a preferred embodiment, the total content of the synthetic or natural polymer (C) is within the range of 10±8 wt.-%, more preferably 10±6 wt.-%, most preferably 10±4 wt.-%, and in particular 10±2 wt.-%, based on the total weight of the formed segment(s) ($S_1$).

In another preferred embodiment, the total content of the synthetic or natural polymer (C) is within the range of 15±12 wt.-%, more preferably 15±10 wt.-%, most preferably 15±7 wt.-%, and in particular 15±3 wt.-%, based on the total weight of the formed segment(s) ($S_1$).

In still another preferred embodiment, the total content of the synthetic or natural polymer (C) is within the range of 20±16 wt.-%, more preferably 20±12 wt.-%, most preferably 20±8 wt.-%, and in particular 20±4 wt.-%, based on the total weight of the formed segment(s) ($S_1$).

In yet another preferred embodiment, the total content of the synthetic or natural polymer (C) is within the range of 25±20 wt.-%, more preferably 25±15 wt.-%, most preferably 25±10 wt.-%, and in particular 25±5 wt.-%, based on the total weight of the formed segment(s) ($S_1$).

In a further preferred embodiment, the total content of the synthetic or natural polymer (C) is within the range of 30±20 wt.-%, more preferably 30±15 wt.-%, most preferably 30±10 wt.-%, and in particular 30±5 wt.-%, based on the total weight of the formed segment(s) ($S_1$).

In still a further preferred embodiment, the total content of the synthetic or natural polymer (C) is within the range of 35±20 wt.-%, more preferably 35±15 wt.-%, most preferably 35±10 wt.-%, and in particular 35±5 wt.-%, based on the total weight of the formed segment(s) ($S_1$).

In a still further preferred embodiment, the total content of the synthetic or natural polymer (C) is within the range of 40±20 wt.-%, more preferably 40±15 wt.-%, and most preferably 40±10 wt.-%, and in particular 40±5 wt.-%, based on the total weight of the formed segment(s) ($S_1$).

In a yet further preferred embodiment, the total content of the synthetic or natural polymer (C) is within the range of 45±20 wt.-%, more preferably 45±15 wt.-%, and most preferably 45±10 wt.-%, and in particular 45±5 wt.-%, based on the total weight of the formed segment(s) ($S_1$).

In another preferred embodiment, the total content of the synthetic or natural polymer (C) is within the range of 50±20 wt.-%, more preferably 50±15 wt.-%, and most preferably 50±10 wt.-%, and in particular 50±5 wt.-%, based on the total weight of the formed segment(s) ($S_1$).

In a yet further preferred embodiment, the total content of the synthetic or natural polymer (C) is within the range of 55±20 wt.-%, more preferably 55±15 wt.-%, and most preferably 55±10 wt.-%, and in particular 55±5 wt.-%, based on the total weight of the formed segment(s) ($S_1$).

In another preferred embodiment, the total content of the synthetic or natural polymer (C) is within the range of 60±20 wt.-%, more preferably 60±15 wt.-%, and most preferably 60±10 wt.-%, and in particular 60±5 wt.-%, based on the total weight of the formed segment(s) ($S_1$).

In a yet further preferred embodiment, the total content of the synthetic or natural polymer (C) is within the range of 65±20 wt.-%, more preferably 65±15 wt.-%, and most preferably 65±10 wt.-%, and in particular 65±5 wt.-%, based on the total weight of the formed segment(s) ($S_1$).

In another preferred embodiment, the total content of the synthetic or natural polymer (C) is within the range of 70±20 wt.-%, more preferably 70±15 wt.-%, and most preferably 70±10 wt.-%, and in particular 70±5 wt.-%, based on the total weight of the formed segment(s) ($S_1$).

In a yet further preferred embodiment, the total content of the synthetic or natural polymer (C) is within the range of 75±20 wt.-%, more preferably 75±15 wt.-%, and most preferably 75±10 wt.-%, and in particular 75±5 wt.-%, based on the total weight of the formed segment(s) ($S_1$).

In another preferred embodiment, the total content of the synthetic or natural polymer (C) is within the range of 80±20 wt.-%, more preferably 80±15 wt.-%, and most preferably 80±10 wt.-%, and in particular 80±5 wt.-%, based on the total weight of the formed segment(s) ($S_1$).

Preferably, the total content of the polymer (C) is within the range of from 1 to 99 wt.-%, more preferably 3 to 90 wt.-%, still more preferably 5 to 75 wt.-%, yet more preferably 7 to 70 wt.-%, most preferably 10 to 65 wt.-% and in particular 10 to 60 wt.-%, based on the total weight of the pharmaceutical dosage form.

In a preferred embodiment, the total content of the polymer (C) is at least 2 wt.-%, more preferably at least 5 wt.-%, still more preferably at least 10 wt.-%, yet more preferably at least 15 wt.-% and in particular at least 20 wt.-%, based on the total weight of the pharmaceutical dosage form.

In a preferred embodiment, the total content of the synthetic or natural polymer (C) is within the range of 10±8 wt.-%, more preferably 10±6 wt.-%, most preferably 10±4 wt.-%, and in particular 10±2 wt.-%, based on the total weight of the pharmaceutical dosage form.

In another preferred embodiment, the total content of the synthetic or natural polymer (C) is within the range of 15±12 wt.-%, more preferably 15±10 wt.-%, most preferably 15±7 wt.-%, and in particular 15±3 wt.-%, based on the total weight of the pharmaceutical dosage form.

In still another preferred embodiment, the total content of the synthetic or natural polymer (C) is within the range of 20±16 wt.-%, more preferably 20±12 wt.-%, most preferably 20±8 wt.-%, and in particular 20±4 wt.-%, based on the total weight of the pharmaceutical dosage form.

In yet another preferred embodiment, the total content of the synthetic or natural polymer (C) is within the range of 25±20 wt.-%, more preferably 25±15 wt.-%, most preferably 25±10 wt.-%, and in particular 25±5 wt.-%, based on the total weight of the pharmaceutical dosage form.

In a further preferred embodiment, the total content of the synthetic or natural polymer (C) is within the range of 30±20 wt.-%, more preferably 30±15 wt.-%, most preferably 30±10 wt.-%, and in particular 30±5 wt.-%, based on the total weight of the pharmaceutical dosage form.

In still a further preferred embodiment, the total content of the synthetic or natural polymer (C) is within the range of 35±20 wt.-%, more preferably 35±15 wt.-%, most preferably 35±10 wt.-%, and in particular 35±5 wt.-%, based on the total weight of the pharmaceutical dosage form.

In a still further preferred embodiment, the total content of the synthetic or natural polymer (C) is within the range of 40±20 wt.-%, more preferably 40±15 wt.-%, and most preferably 40±10 wt.-%, and in particular 40±5 wt.-%, based on the total weight of the pharmaceutical dosage form.

In a yet further preferred embodiment, the total content of the synthetic or natural polymer (C) is within the range of 45±20 wt.-%, more preferably 45±15 wt.-%, and most preferably 45±10 wt.-%, and in particular 45±5 wt.-%, based on the total weight of the pharmaceutical dosage form.

In another preferred embodiment, the total content of the synthetic or natural polymer (C) is within the range of 50±20 wt.-%, more preferably 50±15 wt.-%, and most preferably 50±10 wt.-%, and in particular 50±5 wt.-%, based on the total weight of the pharmaceutical dosage form.

In still another preferred embodiment, the total content of the synthetic or natural polymer (C) is within the range of 60±20 wt.-%, more preferably 60±15 wt.-%, and most preferably 60±10 wt.-%, and in particular 60±5 wt.-%, based on the total weight of the pharmaceutical dosage form.

In yet another preferred embodiment, the total content of the synthetic or natural polymer (C) is within the range of 70±20 wt.-%, more preferably 70±15 wt.-%, and most preferably 70±10 wt.-%, and in particular 70±5 wt.-%, based on the total weight of the pharmaceutical dosage form.

Preferably, the relative weight ratio of the polymer (C) to the first pharmacologically active ingredient ($A_1$) is within the range of 40:1 to 1:40 or 35:1 to 1:35 or 30:1 to 1:30 or 20:1 to 1:20, more preferably 15:1 to 1:15, still more preferably 10:1 to 1:10, yet more preferably 7:1 to 1:7, most preferably 5:1 to 1:5, and in particular 2:1 to 1:2.

The synthetic or natural polymer (C) is preferably selected from the group consisting of polyalkylene oxides (preferably polymethylene oxide, polyethylene oxide, polypropylene oxide), polyethylenes, polypropylenes, polyvinyl chlorides, polycarbonates, polystyrenes, polyacrylates, poly (hydroxy fatty acids), poly(hydroxyvaleric acids); polycaprolactones, polyvinyl alcohols, polyesteramides, polyethylene succinates, polylactones, polyglycolides, cellulose ethers (preferably methylcellulose, ethylcellulose, hydroxyethylcellulose, hydroxypropylcellulose, hydroxypropylmethylcellulose), polyurethanes, polyvinylpyrrolidones, polyamides, polylactides, polyacetals, polylactide/glycolides, polylactones, polyglycolides, poly-orthoesters, polyanhydrides, copolymers thereof, block-copolymers thereof, and mixtures of at least two of the stated polymers.

In a preferred embodiment, polymer (C) is non-ionic. In another preferred embodiment, polymer (C) is anionic. In still another preferred embodiment, polymer (C) is cationic.

Preferably, the synthetic or natural polymer (C) is selected from acrylic polymers or polyalkylene oxides.

In a particularly preferred embodiment,
(i) the content of the synthetic or natural polymer (C) is at least 30 wt.-% relative to the total weight of the formed segment(s) ($S_1$); and/or
(ii) polymer (C) is selected from acrylic polymers or polyalkylene oxides.

In a preferred embodiment, polymer (C) is an acrylic polymer which is preferably derived from a monomer mixture comprising a first $C_{1-4}$-alkyl (meth)acrylate and a second $C_{1-4}$-alkyl (meth)acrylate differing from said first $C_{1-4}$-alkyl (meth)acrylate.

When the prolonged release matrix material of the prolonged release matrix comprises an acrylic polymer, it preferably does not additionally comprise an polyalkylene oxide or a waxy material, and vice versa. However, it is principally possible that the prolonged release matrix material of the prolonged release matrix comprises a combination of an acrylic polymer, a polyalkylene oxide and/or a waxy material.

Preferred $C_{1-4}$-alkyl (meth)acrylates include methyl methacrylate, methyl acrylate, ethyl methacrylate, ethyl acrylate, propyl methacrylate, propyl acrylate, butyl methacrylate, and butyl acrylate.

For the purpose of the specification, "(meth)acryl" refers to acryl as well as methacryl.

Preferably, the acrylic polymer has a weight average molecular weight within the range of from 100,000 g/mol to 2,000,000 g/mol. In a preferred embodiment, the acrylic polymer has a weight average molecular weight ($M_W$) or viscosity average molecular weight ($M_1$) of at least 150,000 or at least 200,000 g/mol, preferably at least 250,000 g/mol or at least 300,000 g/mol, more preferably in the range of about 300,000 g/mol to about 2,000,000 g/mol, and most preferably in the range of about 300,000 g/mol to about 1,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

The acrylic polymer can be a nonionic acrylic polymer or an ionic acrylic polymer. For the purpose of specification, "nonionic polymer" refers to a polymer not containing more than 1 mole.-% ionic, i.e. anionic or cationic, monomer units, preferably containing no ionic monomer units at all.

In a preferred embodiment, the synthetic or natural polymer (C) is a nonionic acrylic polymer which is preferably derived from a monomer mixture comprising a first $C_{1-4}$-alkyl (meth)acrylate and a second $C_{1-4}$-alkyl (meth)acrylate differing from said first $C_{1-4}$-alkyl (meth)acrylate.

Preferably, the first $C_{1-4}$-alkyl (meth)acrylate is ethyl acrylate and the second $C_{1-4}$-alkyl (meth)acrylate is methyl methacrylate.

Preferably, the relative molar content of the ethyl acrylate within the nonionic acrylic polymer is greater than the relative molar content of the methyl methacrylate within the nonionic acrylic polymer.

Preferably, the molar ratio of the first $C_{1-4}$-alkyl (meth) acrylate, which is preferably ethyl acrylate, to the second $C_{1-4}$-alkyl (meth)acrylate, which is preferably methyl methacrylate, is within the range of from 5:1 to 1:3, more preferably from 4.5:1 to 1:2.5, still more preferably from 4:1 to 1:2, yet more preferably from 3.5:1 to 1:1.5, even more preferably from 3:1 to 1:1, most preferably from 2.5:1 to 1.5:1, and in particular about 2:1.

Preferably, the nonionic acrylic polymer has a weight average molecular weight within the range of from 100,000 g/mol to 2,000,000 g/mol. In a preferred embodiment, the nonionic acrylic polymer has a weight average molecular weight ($M_W$) or viscosity average molecular weight ($M_1$) of at least 150,000 or at least 200,000 g/mol, preferably at least 250,000 g/mol or at least 300,000 g/mol, more preferably in the range of about 300,000 g/mol to about 2,000,000 g/mol, and most preferably in the range of about 300,000 g/mol to about 1,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

In a preferred embodiment, the weight average molecular weight of the nonionic acrylic polymer is within the range of 675,000±500,000 g/mol, more preferably 675,000±450,000 g/mol, still more preferably 675,000±400,000 g/mol, yet more preferably 675,000±350,000 g/mol, even more preferably 675,000±300,000 g/mol, most preferably 675,000±250,000 g/mol, and in particular 675,000±200,000 g/mol.

The nonionic acrylic polymer may comprise a single nonionic acrylic polymer having a particular average molecular weight, or a mixture (blend) of different nonionic acrylic polymers, such as two, three, four or five nonionic acrylic polymers, e.g., nonionic acrylic polymers of the same chemical nature but different average molecular weight, nonionic acrylic polymers of different chemical nature but same average molecular weight, or nonionic acrylic polymers of different chemical nature as well as different molecular weight.

In a preferred embodiment, the nonionic acrylic polymer is homogeneously distributed in the formed segment(s) ($S_1$). According to this embodiment, the first pharmacologically active ingredient ($A_1$) and the nonionic acrylic polymer are intimately homogeneously distributed in the formed segment(s) ($S_1$), so that the formed segment(s) ($S_1$) do(es) not contain any portions where either the first pharmacologically active ingredient ($A_1$) is present in the absence of nonionic acrylic polymer or where nonionic acrylic polymer is present in the absence of the first pharmacologically active ingredient ($A_1$).

When the formed segment(s) ($S_1$) is/are film coated, the nonionic acrylic polymer is preferably homogeneously distributed in the body of the formed segment(s) ($S_1$), i.e. the film coating preferably does not contain nonionic acrylic polymer. Nonetheless, the film coating as such may of course contain one or more polymers, which however, preferably differ from the nonionic acrylic polymer contained in the body.

The nonionic acrylic polymer preferably has a glass transition temperature ($T_g$) within the range of 1±15° C., more preferably 1±11° C.

The nonionic acrylic polymer preferably has a minimum film forming temperature (MFT) within the range of 5±5° C., more preferably 5±2° C.

Nonionic acrylic polymers that are suitable for use in the formed segment ($S_1$) according to the invention are commercially available, e.g. from Evonik. For example, Eudragit® NE30D, Eudragit® NE40D and Eudragit® NM30D, which are provided as aqueous dispersions of poly(ethyl acrylate-co-methyl methacrylate) 2:1, may be used in the formed segment ($S_1$) according to the invention. For details concerning the properties of these products, it can be referred to e.g. the product specification.

In a preferred embodiment, the synthetic or natural polymer (C) is an ionic acrylic polymer.

In a preferred embodiment, the ionic acrylic polymer is homogeneously distributed in the formed segment(s) ($S_1$). According to this embodiment, the first pharmacologically active ingredient ($A_1$) and the ionic acrylic polymer are intimately homogeneously distributed in the formed segment(s) ($S_1$), so that the formed segment(s) ($S_1$) do(es) not contain any portions where either the first pharmacologically active ingredient ($A_1$) is present in the absence of ionic acrylic polymer or where ionic acrylic polymer is present in the absence of the first pharmacologically active ingredient ($A_1$).

When the formed segment(s) ($S_1$) is/are film coated, the ionic acrylic polymer is preferably homogeneously distributed in the body of the formed segment(s) ($S_1$), i.e. the film coating preferably does not contain ionic acrylic polymer. Nonetheless, the film coating as such may of course contain one or more polymers, which however, preferably differ from the ionic acrylic polymer contained in the body.

Preferred ionic acrylic polymers are anionic acrylic polymers. Preferred anionic acrylic polymers include but are not limited to copolymers of one or two different $C_{1-4}$-alkyl (meth)acrylate monomers and copolymerizable anionic monomers such as acrylic acid. Preferred representatives are ternary copolymers of methyl acrylate, methyl methacrylate and methacrylic acid, wherein the relative molar content of the monomers is preferably methyl acrylate>methyl methacrylate>methacrylic acid. Preferably, the anionic acrylic polymer has a weight average molecular weight within the range of 280,000±250,000 g/mol, more preferably 280,000±200,000 g/mol, still more preferably 280,000±180,000 g/mol, yet more preferably 280,000±160,000 g/mol, even more preferably 280,000±140,000 g/mol, most preferably 280,000±120,000 g/mol, and in particular 280,000±100,000 g/mol. Poly(methyl acrylate-co-methyl methacrylate-co-methacrylic acid) 7:3:1 having an average molecular weight of about 280,000 g/mol is commercially available as Eudragit® FS.

Other preferred ionic acrylic polymers are cationic acrylic polymers. Preferred cationic acrylic polymers include but are not limited to copolymers of one or two different $C_{1-4}$-alkyl (meth)acrylate monomers and copolymerizable cationic monomers such as trimethylammonioethyl methacrylate chloride. Preferred representatives are ternary copolymers of ethyl acrylate, methyl methacrylate and a low content of methacrylic acid ester with quaternary ammonium groups, preferably trimethylammonioethyl methacrylate chloride, wherein the relative molar content of the monomers is preferably methyl methacrylate>ethyl acrylate>copolymerizable cationic monomers. Preferably, the cationic acrylic polymer has a weight average molecular weight within the range of 32,000±30,000 g/mol, more preferably 32,000±27,000 g/mol, still more preferably 32,000±23,000 g/mol, yet more preferably 32,000±20,000 g/mol, even more preferably 32,000±17,000 g/mol, most preferably 32,000±13,000 g/mol, and in particular 32,000±10,000 g/mol. Poly(ethyl acrylate-co-methyl methacrylate-co-trimethylammonioethyl methacrylate chloride) 1:2:0.1 and 1:2:0.2, respectively, having an average molecular weight of about 32,000 g/mol is commercially available as Eudragit® RS-PO and Eudragit® RL-PO, respectively. Because of its lower content of trimethylammonioethyl methacrylate chloride, Eudragit® RS-PO is particularly preferred. Another preferred cationic acrylic polymer is Eudragit® RL 100 which is a copolymer of ethyl acrylate, methyl methacrylate and a low content of methacrylic acid ester with quaternary ammonium groups.

In a preferred embodiment, the synthetic or natural polymer (C) is a polyalkylene oxide, preferably a polyethylene oxide, particularly preferably having an weight average molecular weight of at least 500,000 g/mol.

When the prolonged release matrix material of the prolonged release matrix comprises a polyalkylene oxide, it preferably does not additionally comprise an acrylic polymer or a waxy material, and vice versa.

In a preferred embodiment, the polyalkylene oxide is homogeneously distributed in the formed segment(s) ($S_1$). According to this embodiment, the first pharmacologically active ingredient ($A_1$) and the polyalkylene oxide are intimately homogeneously distributed in the formed segment(s) ($S_1$), so that the formed segment(s) ($S_1$) do(es) not contain any portions where either the first pharmacologically active ingredient ($A_1$) is present in the absence of polyalkylene oxide or where polyalkylene oxide is present in the absence of the first pharmacologically active ingredient ($A_1$).

When the formed segment(s) ($S_1$) is/are film coated, the polyalkylene oxide is preferably homogeneously distributed in the body of the formed segment(s) ($S_1$), i.e. the film coating preferably does not contain polyalkylene oxide. Nonetheless, the film coating as such may of course contain one or more polymers, which however, preferably differ from the polyalkylene oxide contained in the body.

Preferably, the polyalkylene oxide is selected from polymethylene oxide, polyethylene oxide and polypropylene oxide, or copolymers or mixtures thereof.

Preferably, the polyalkylene oxide has a weight average molecular weight ($M_W$), preferably also a viscosity average molecular weight ($M_\eta$) of more than 200,000 g/mol or at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Preferably, the molecular weight dispersity $M_W/M_n$ of the polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide preferably has a viscosity at 25° C. of 30 to 17,600 mPa·s, more preferably 55 to 17,600 mPa·s, still more preferably 600 to 17,600 mPa·s, yet more preferably 4,500 to 17,600 mPa·s, even more preferably 4,500 to 12,000 mPa·s, most preferably 5,000 to 10,500 mPa·s and in particular 5,500 to 7,500 mPa·s or 7,500 to 10,000 mPa·s, measured in a 1 wt.-% aqueous solution.

The polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of specification, a polyalkylene glycol has a molecular weight of up to 20,000 g/mol whereas a polyalkylene oxide has a molecular weight of more than 20,000 g/mol. The weight average over all molecular weights of all polyalkylene oxides that are contained in the pharmaceutical dosage form is more than 200,000 g/mol. Thus, polyalkylene glycols, if any, are preferably not taken into consideration when determining the weight average molecular weight of polyalkylene oxide.

In a particularly preferred embodiment, the synthetic or natural polymer (C) is a polyalkylene oxide the content of which is at least 30 wt.-% relative to the total weight of the formed segment(s) ($S_1$).

Preferably, the polyalkylene oxide is combined with another polymer, preferably a cellulose ether, particularly preferably a cellulose ether selected from the group consisting of methylcellulose, ethylcellulose, hydroxyethylcellulose, hydroxypropylcellulose, and hydroxypropylmethylcellulose. Hydroxypropylmethylcellulose is particularly preferred.

Preferably, the relative weight ratio of the polyalkylene oxide and the cellulose ether is within the range of from 14:1 to 1:2, more preferably 13:1 to 1:1, still more preferably 12:1 to 2:1, yet more preferably 11:1 to 3:1, even more preferably 10:1 to 4:1, most preferably 9:1 to 5:1, and in particular 8:1 to 6:1.

In another preferred embodiment, the prolonged release matrix material comprises a waxy material, preferably selected from the group consisting of
- glycerides, especially monoglycerides, diglycerides, triglycerides,
- esters of fatty acids with fatty alcohols, and
- paraffins.

When the prolonged release matrix material of the prolonged release matrix comprises a waxy material, it preferably does not additionally comprise an acrylic polymer or a polyalkylene oxide, and vice versa.

As used herein a "waxy material" refers to a material which melts into liquid form having low viscosity upon heating and sets again to a solid state upon cooling. Preferably, the waxy material has a melting point of at least 30° C., more preferably at least 35° C., still more preferably at least 40° C., yet more preferably at least 45° C., even more preferably at least 50° C., most preferably at least 55° C., and in particular at least 60° C.

When the waxy material is or comprises a monoglyceride, diglyceride, triglyceride or a mixture thereof, it is preferably a mono-, di- or triester of glycerol and carboxylic acids, whereas the carboxylic acid is preferably selected from the group consisting of fatty acids, hydroxy fatty acids and aromatic acids.

In another preferred embodiment, the glyceride is a fatty acid macrogolglyceride, e.g. lauroyl macrogolglyceride, such as Gelucire 44/14 that can be regarded as a non-ionic water dispersible surfactant composed of well-characterized PEG-esters, a small glyceride fraction and free PEG.

Preferred glycerides of fatty acids include monoglycerides, diglycerides, triglycerides, and mixtures thereof; preferably of $C_6$ to $C_{22}$ fatty acids. Especially preferred are partial glycerides of the $C_{16}$ to $C_{22}$ fatty acids such as glycerol behenat, glycerol monostearate, glycerol palmitostearate and glyceryl distearate as well as triglycerides of the $C_{16}$ to $C_{22}$ fatty acids such as glycerol tristearate.

The term "fatty acid" is well acknowledged in the art and includes for example unsaturated representatives such as myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid; as well as saturated representatives such as caprylic acid, capric acid, lauric acid, myristic acid, palmitic acid, stearic acid, arachidic acid, behenic acid, lignoceric acid, and cerotic acid.

The term "hydroxy fatty acid" is also well acknowledged in the art and includes for example 2-hydroxyhexanoic acid, 2-hydroxyoctanoic acid, 2-hydroxydecanoic acid, 2-hydroxy-dodecanoic acid, β-hydroxylauric acid, 2-hydroxytetradecanoic acid, β-hydroxymyristic acid, 15-hydroxypentadecanoic acid, 16-hydroxyhexadecanoic acid, β-hydroxypalmitic acid, 12-hydroxyoctadecanoic acid, α-hydroxystearic acid, and α-hydroxyarachidic acid.

The fatty acids and the hydroxy fatty acids are preferably saturated.

When the waxy material is or comprises a diglyceride or a triglyceride, the fatty acids, hydroxy fatty acids and aromatic acids, respectively, may be identical or different.

According to this embodiment of the invention, the waxy material is preferably a hard fat (adeps solidus) in accordance with Ph. Eur.

Preferably, the waxy material is a monoglyceride, diglyceride, triglyceride or a mixture thereof, selected from the group consisting of hydrogenated soybean oil, hydrogenated palm oil, hydrogenated castor oil, hydrogenated cottonseed oil, and mixtures thereof.

When the waxy material is or comprises an ester of a fatty acid with a fatty alcohol, the fatty acid is preferably a saturated fatty acid. Preferred examples of fatty acids are already mentioned above in connection with the glycerides. The fatty alcohol is preferably derived from a fatty acid and preferably also saturated.

Preferred representatives of esters of fatty acids with fatty alcohols include but are not limited to natural waxes such as beeswax, carnaubawax, candelilla wax, ouricury wax, sugarcane wax, cetyl palmitate, oleyl oleate, cetaceum and retamo wax.

When the waxy material is or comprises paraffin, the paraffin is preferably a hard paraffin (paraffinum solidum, ceresin, zeresin) in accordance with Ph. Eur.

The waxy material may comprise a single waxy material, or a mixture (blend) of different waxy materials, such as two, three, four or five waxy materials, each of which preferably being selected from the group consisting of glycerides, especially monoglycerides, diglycerides, triglycerides; esters of fatty acids with fatty alcohols; and paraffins.

In a preferred embodiment, the waxy material is homogeneously distributed in the formed segment(s) ($S_1$). According to this embodiment, the first pharmacologically active ingredient ($A_1$) and the waxy material are intimately homogeneously distributed in the formed segment(s) ($S_1$), so that the formed segment(s) ($S_1$) do(es) not contain any portions where either the first pharmacologically active ingredient ($A_1$) is present in the absence of waxy material or where waxy material is present in the absence of the first pharmacologically active ingredient ($A_1$).

When the formed segment(s) ($S_1$) is/are film coated, the waxy material is preferably homogeneously distributed in the formed segment(s) ($S_1$), i.e. the film coating preferably does not contain waxy material. Nonetheless, the film coating as such may of course contain one or more waxy materials, which however, preferably differ from the waxy materials contained in the body.

Waxy materials that are suitable for use in the pharmaceutical dosage forms according to the invention are commercially available, e.g. Cera alba, Cera flava, Kolliwax™ HCO, Dynasan® 118, Compritol® 888 ATO, Precirol® ATO 5, Gelucire® 44/14, and the like. For details concerning the properties of these products, it can be referred to e.g. the product specification.

The total content of the waxy material is preferably within the range of from 5.0 to 95 wt.-%, more preferably 10 to 90 wt.-%, still more preferably 15 to 85 wt.-%, yet more preferably 20 to 80 wt.-%, even more preferably 25 to 75 wt.-%, most preferably 30 to 70 wt.-%, and in particular 35 to 75 wt.-%, relative to the total weight of the prolonged release matrix.

Preferably, the total content of the waxy material is within the range of from 1 to 90 wt.-%, more preferably 3 to 85 wt.-%, still more preferably 5 to 80 wt.-%, yet more preferably 7 to 75 wt.-%, most preferably 10 to 70 wt.-% and in particular 15 to 65 wt.-%, based on the total weight of the formed segment(s) ($S_1$).

In a preferred embodiment, the total content of the waxy material is at least 2 wt.-%, more preferably at least 5 wt.-%, still more preferably at least 10 wt.-%, yet more preferably at least 15 wt.-% and in particular at least 20 wt.-%, based on the total weight of the formed segment(s) ($S_1$).

In a preferred embodiment, the total content of waxy material is within the range of 10±8 wt.-%, more preferably 10±6 wt.-%, most preferably 10±4 wt.-%, and in particular 10±2 wt.-%, based on the total weight of the formed segment(s) ($S_1$).

In another preferred embodiment, the total content of waxy material is within the range of 15±12 wt.-%, more preferably 15±10 wt.-%, most preferably 15±7 wt.-%, and in particular 15±3 wt.-%, based on the total weight of the formed segment(s) ($S_1$).

In still another preferred embodiment, the total content of waxy material is within the range of 20±16 wt.-%, more preferably 20±12 wt.-%, most preferably 20±8 wt.-%, and in particular 20±4 wt.-%, based on the total weight of the formed segment(s) ($S_1$).

In yet another preferred embodiment, the total content of waxy material is within the range of 25±20 wt.-%, more preferably 25±15 wt.-%, most preferably 25±10 wt.-%, and in particular 25±5 wt.-%, based on the total weight of the formed segment(s) ($S_1$).

In a further preferred embodiment, the total content of waxy material is within the range of 30±20 wt.-%, more preferably 30±15 wt.-%, most preferably 30±10 wt.-%, and in particular 30±5 wt.-%, based on the total weight of the formed segment(s) ($S_1$).

In still a further preferred embodiment, the total content of waxy material is within the range of 35±20 wt.-%, more preferably 35±15 wt.-%, most preferably 35±10 wt.-%, and in particular 35±5 wt.-%, based on the total weight of the formed segment(s) ($S_1$).

In a still further preferred embodiment, the total content of waxy material is within the range of 40±20 wt.-%, more preferably 40±15 wt.-%, and most preferably 40±10 wt.-%, and in particular 40±5 wt.-%, based on the total weight of the formed segment(s) ($S_1$).

In a yet further preferred embodiment, the total content of waxy material is within the range of 45±20 wt.-%, more preferably 45±15 wt.-%, and most preferably 45±10 wt.-%, and in particular 45±5 wt.-%, based on the total weight of the formed segment(s) ($S_1$).

In another preferred embodiment, the total content of waxy material is within the range of 50±20 wt.-%, more preferably 50±15 wt.-%, and most preferably 50±10 wt.-%, and in particular 50±5 wt.-%, based on the total weight of the formed segment(s) ($S_1$).

In a yet further preferred embodiment, the total content of waxy material is within the range of 55±20 wt.-%, more preferably 55±15 wt.-%, and most preferably 55±10 wt.-%, and in particular 55±5 wt.-%, based on the total weight of the formed segment(s) ($S_1$).

In another preferred embodiment, the total content of waxy material is within the range of 60±20 wt.-%, more preferably 60±15 wt.-%, and most preferably 60±10 wt.-%, and in particular 60±5 wt.-%, based on the total weight of the formed segment(s) ($S_1$).

In a yet further preferred embodiment, the total content of waxy material is within the range of 65±20 wt.-%, more preferably 65±15 wt.-%, and most preferably 65±10 wt.-%, and in particular 65±5 wt.-%, based on the total weight of the formed segment(s) ($S_1$).

In another preferred embodiment, the total content of waxy material is within the range of 70±20 wt.-%, more preferably 70±15 wt.-%, and most preferably 70±10 wt.-%, and in particular 70±5 wt.-%, based on the total weight of the formed segment(s) ($S_1$).

In a yet further preferred embodiment, the total content of waxy material is within the range of 75±20 wt.-%, more preferably 75±15 wt.-%, and most preferably 75±10 wt.-%, and in particular 75±5 wt.-%, based on the total weight of the formed segment(s) ($S_1$).

In another preferred embodiment, the total content of waxy material is within the range of 80±20 wt.-%, more preferably 80±15 wt.-%, and most preferably 80±10 wt.-%, and in particular 80±5 wt.-%, based on the total weight of the formed segment(s) ($S_1$).

Preferably, the relative weight ratio of the waxy material to the first pharmacologically active ingredient ($A_1$) is within the range of 20:1 to 1:20, more preferably 15:1 to 1:15, still more preferably 10:1 to 1:10, yet more preferably 7:1 to 1:7, most preferably 5:1 to 1:5, and in particular 2:1 to 1:2.

Besides the first pharmacologically active ingredient ($A_1$) and the optionally present prolonged release matrix material the formed segment(s) ($S_1$) may optionally further comprise additional pharmaceutical excipients conventionally contained in pharmaceutical dosage forms in conventional amounts, such as antioxidants, preservatives, lubricants, plasticizer, fillers/binders, and the like.

The skilled person will readily be able to determine appropriate further excipients as well as the quantities of each of these excipients. Specific examples of pharmaceutically acceptable carriers and excipients are described in the Handbook of Pharmaceutical Excipients, American Pharmaceutical Association (1986).

In a preferred embodiment, the formed segment ($S_1$) does not contain a disintegrant.

Preferably, the formed segment(s) ($S_1$) further comprise(s) an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the formed segment(s) ($S_1$).

In a preferred embodiment, the formed segment(s) ($S_1$) further comprise(s) an acid, preferably a carboxylic acid, more preferably a multicarboxylic acid, particularly citric acid. The content of acid is preferably in the range of 0.01 wt.-% to about 20 wt.-%, more preferably in the range of 0.02 wt.-% to about 10 wt.-%, and still more preferably in the range of 0.05 wt.-% to about 5 wt.-%, and most preferably in the range of 0.1 wt.-% to about 1.0 wt.-%, based on the total weight of the formed segment(s) ($S_1$).

In a preferred embodiment, the formed segment(s) ($S_1$) contain(s) at least one lubricant. In another preferred embodiment, the formed segment(s) ($S_1$) contain(s) no lubricant.

Especially preferred lubricants are selected from magnesium stearate, calcium stearate and stearic acid;

polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogolglycerolmonostearate, macrogol-6-glycerolcaprylocaprate, macrogolglycerololeate; macrogolglycerolstearate, macrogolglycerolhydroxystearate, and macrogolglycerolrizinoleate;

polyglycolyzed glycerides, such as the one known and commercially available under the trade name "Labrasol";

fatty alcohols that may be linear or branched, such as cetylalcohol, stearylalcohol, cetylstearyl alcohol, 2-octyldodecane-1-ol and 2-hexyldecane-1-ol; and polyethylene glycols having a molecular weight between 10.000 and 60.000 g/mol.

Particularly preferred lubricants comprise stearic acid, calcium stearate and stearyl alcohol or a mixture thereof.

Preferably, the content of the lubricant ranges from 0.01 wt.-% to about 10 or 15 wt.-%, more preferably in the range of 0.05 wt.-% to about 7.5 wt.-%, most preferably in the range of 0.1 wt.-% to about 5 wt.-% or 1.5 wt.-% to about 4 wt, and in particular in the range of 0.1 wt.-% to about 1 wt.-% or 3.5 to about 5.5 wt.-%, based on the total weight of the formed segment(s) ($S_1$).

When the formed segment(s) ($S_1$) contain(s) more than one lubricant, preferably, the overall content of the lubricant ranges from 3 wt.-% to about 20 wt.-%, more preferably in the range of 5 wt.-% to about 15 wt.-%, most preferably in the range of 7 wt.-% to about 12 wt.-%, and in particular in the range of 8 wt.-% to about 10 wt.-%, based on the total weight of the formed segment(s) ($S_1$).

Preferably, the formed segment(s) ($S_1$) further comprise(s) a plasticizer. The plasticizer improves the processability of the prolonged release matrix material. A preferred plasticizer is polyalkylene glycol, like polyethylene glycol, triethyl citrate (TEC), triacetin, fatty acids, fatty acid esters, waxes and/or microcrystalline waxes. Particularly preferred plasticizers are polyethylene glycols, such as PEG 6000. Further particularly preferred plasticizers comprise triethyl citrate (TEC), stearic acid, calcium stearate and stearyl alcohol or a mixture thereof.

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the formed segment(s) ($S_1$).

When the formed segment ($S_1$) contains more than one plasticizer, preferably, the overall amount of the plasticizer ranges from 3 wt.-% to about 20 wt.-%, more preferably in the range of 5 wt.-% to about 20 wt.-% or to about 15 wt.-%, most preferably in the range of 7 wt.-% to about 20 wt.-% or to about 12 wt.-%, and in particular in the range of 8 wt.-% to about 20 wt.-% or to about 10 wt.-%, based on the total weight of the formed segment(s) ($S_1$).

Plasticizers can sometimes act as a lubricant, and lubricants can sometimes act as a plasticizer.

Preferably, the formed segment(s) ($S_1$) further comprise(s) a filler/binder. A preferred filler/binder is selected from celluloses, cellulose derivatives such as cellulose ethers and cellulose esters, and tricalcium phosphate.

A particularly preferred filler/binder is selected from cellulose esters and cellulose ethers, in particular hydroxypropyl methylcellulose (HPMC).

The content of the filler/binder, preferably HPMC, preferably ranges from 0.1 wt.-% to about 30 wt.-%, more preferably in the range of 1.0 wt.-% to about 20 wt.-%, and most preferably in the range of 2.0 wt.-% to about 15 wt.-% relative to the total weight of the formed segment(s) ($S_1$).

In a preferred embodiment, besides the first pharmacologically active ingredient ($A_1$) that may have any solubility in aqueous ethanol, relative to the total weight of the formed segment(s) ($S_1$), the formed segment(s) ($S_1$) according to the invention preferably contain(s) at most 25 wt.-%, more preferably at most 20 wt.-%, still more preferably at most 15 wt.-%, yet more preferably at most 10 wt.-%, even more preferably at most 5.0 wt.-%, most preferably at most 2.5 wt.-%, and in particular at most 1.0 wt.-% of ingredients (prolonged release matrix material, excipients, and the like) having at room temperature in aqueous ethanol (40 vol.-%) a solubility of at least 100 mg/ml, more preferably a solubility of at least 75 mg/ml, still more preferably a solubility of at least 50 mg/ml, yet more preferably a solubility of at least 25 mg/ml, even more preferably a solubility of at least 10 mg/ml, most preferably a solubility of at least 5.0 mg/ml, and in particular a solubility of at least 1.0 mg/ml.

Preferred contents of the first pharmacologically active ingredient ($A_1$), prolonged release matrix material, and excipients, relative to the total weight of the formed segment(s) ($S_1$), are summarized as embodiments $B^1$ to $B^{28}$ in the tables here below:

| wt.-% | $B^1$ | $B^2$ | $B^3$ | $B^4$ |
|---|---|---|---|---|
| first pharmacologically active ingredient ($A_1$) | 40 ± 30 | 40 ± 20 | 40 ± 10 | 40 ± 5 |
| synthetic or natural polymer (C) | 50 ± 30 | 50 ± 20 | 50 ± 10 | 50 ± 5 |
| pharmaceutical excipients | 20 ± 20 | 20 ± 20 | 20 ± 20 | 20 ± 20 |

| wt.-% | $B^5$ | $B^6$ | $B^7$ | $B^8$ |
|---|---|---|---|---|
| first pharmacologically active ingredient ($A_1$) | 30 ± 25 | 30 ± 20 | 30 ± 10 | 30 ± 5 |
| synthetic or natural polymer (C) | 50 ± 30 | 50 ± 20 | 50 ± 10 | 50 ± 5 |
| pharmaceutical excipients | 20 ± 20 | 20 ± 20 | 20 ± 20 | 20 ± 20 |

| wt.-% | $B^9$ | $B^{10}$ | $B^{11}$ | $B^{12}$ |
|---|---|---|---|---|
| first pharmacologically active ingredient ($A_1$) | 20 ± 15 | 20 ± 12.5 | 20 ± 10 | 20 ± 5 |
| synthetic or natural polymer (C) | 50 ± 30 | 50 ± 20 | 50 ± 10 | 50 ± 5 |
| pharmaceutical excipients | 20 ± 20 | 20 ± 20 | 20 ± 20 | 20 ± 20 |

| wt.-% | $B^{13}$ | $B^{14}$ | $B^{15}$ | $B^{16}$ |
|---|---|---|---|---|
| first pharmacologically active ingredient ($A_1$) | 10 ± 7.5 | 10 ± 7.5 | 10 ± 5 | 10 ± 5 |
| synthetic or natural polymer (C) | 50 ± 30 | 50 ± 20 | 50 ± 10 | 50 ± 10 |
| pharmaceutical excipients | 20 ± 20 | 20 ± 20 | 20 ± 20 | 20 ± 20 |

| wt.-% | $B^{17}$ | $B^{18}$ | $B^{19}$ | $B^{20}$ |
|---|---|---|---|---|
| first pharmacologically active ingredient ($A_1$) | 20 ± 15 | 20 ± 12.5 | 20 ± 10 | 20 ± 5 |
| synthetic or natural polymer (C) | 40 ± 30 | 40 ± 20 | 40 ± 10 | 40 ± 5 |
| pharmaceutical excipients | 20 ± 20 | 20 ± 20 | 20 ± 20 | 20 ± 20 |

| wt.-% | $B^{21}$ | $B^{22}$ | $B^{23}$ | $B^{24}$ |
|---|---|---|---|---|
| first pharmacologically active ingredient ($A_1$) | 20 ± 15 | 20 ± 12.5 | 20 ± 10 | 20 ± 5 |
| synthetic or natural polymer (C) | 60 ± 40 | 60 ± 30 | 60 ± 20 | 60 ± 10 |
| pharmaceutical excipients | 20 ± 20 | 20 ± 20 | 20 ± 20 | 20 ± 20 |

| wt.-% | $B^{25}$ | $B^{26}$ | $B^{27}$ | $B^{28}$ |
|---|---|---|---|---|
| first pharmacologically active ingredient ($A_1$) | 10 ± 9 | 10 ± 7 | 10 ± 5 | 10 ± 3 |
| synthetic or natural polymer (C) | 70 ± 40 | 60 ± 30 | 60 ± 20 | 60 ± 10 |
| pharmaceutical excipients | 20 ± 20 | 20 ± 20 | 20 ± 20 | 20 ± 20 |

The formed segment(s) ($S_1$) provide(s) prolonged release of the first pharmacologically active ingredient ($A_1$). Preferably, the prolonged release matrix provides for a prolonged release of the first pharmacologically active ingredient ($A_1$) from the formed segment ($S_1$).

Preferably, under in vitro conditions the pharmaceutical dosage form has released after 30 minutes 0.1 to 75%, after 240 minutes 0.5 to 95%, after 480 minutes 1.0 to 100% and after 720 minutes 2.5 to 100% of the first pharmacologically active ingredient ($A_1$).

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 600 mL simulated intestinal fluid pH 6.8 (phosphate buffer) or pH 4.5. In a preferred embodiment, the rotational speed of the paddle is increased to 75 rpm. In another preferred embodiment, the release profile is determined under the following conditions: basket method, 75 rpm, 37±5° C., 600 mL 0.1 N HCl or 600 mL of SIF sp (pH 6.8) or 600 mL of 0.1 N HCl+40% ethanol.

Preferred release profiles $R^1$ to $R^6$ are summarized in the table here below [all data in wt.-% of released first pharmacologically active ingredient ($A_1$)]:

| time | $R^1$ | $R^2$ | $R^3$ | $R^4$ | $R^5$ | $R^6$ |
|---|---|---|---|---|---|---|
| 60 min | 0-30 | 0-50 | 0-50 | 15-25 | 20-30 | 20-50 |
| 120 min | 0-40 | 0-75 | 0-75 | 25-40 | 35-50 | 40-75 |
| 240 min | 3-55 | 3-95 | 10-95 | 40-70 | 55-75 | 60-95 |
| 480 min | 10-65 | 10-100 | 35-100 | 60-90 | 80-95 | 80-100 |
| 720 min | 20-75 | 20-100 | 55-100 | 70-100 | 90-100 | 90-100 |
| 960 min | 30-88 | 30-100 | 70-100 | >80 | 95-100 | |
| 1440 min | 50-100 | 50-100 | >90 | | | |
| 2160 min | >80 | >80 | | | | |

Further preferred release profiles $R^7$ to $R^{13}$ are summarized in the table here below [all data in wt.-% of released first pharmacologically active ingredient ($A_1$)]:

| time | $R^7$ | $R^8$ | $R^9$ | $R^{10}$ | $R^{11}$ | $R^{12}$ | $R^{13}$ |
|---|---|---|---|---|---|---|---|
| 30 min | 17.5 ± 7.5 | 17.5 ± 6.5 | 17.5 ± 5.5 | 17.5 ± 4.5 | 17.5 ± 3.5 | 17.5 ± 2.5 | 15 ± 6.5 |
| 60 min | 27.0 ± 8.0 | 27.0 ± 7.0 | 27.0 ± 6.0 | 27.0 ± 5.0 | 27.0 ± 4.0 | 27.0 ± 3.0 | 20 ± 7.0 |
| 120 min | 41.5 ± 9.5 | 41.5 ± 8.5 | 41.5 ± 7.5 | 41.5 ± 6.5 | 41.5 ± 5.5 | 41.5 ± 4.5 | 25 ± 8.5 |
| 240 min | 64.5 ± 12.5 | 64.5 ± 11.5 | 64.5 ± 10.5 | 64.5 ± 9.5 | 64.5 ± 8.5 | 64.5 ± 7.5 | 37 ± 11.5 |
| 480 min | 88.0 ± 12.0 | 88.0 ± 11.0 | 88.0 ± 10.0 | 88.0 ± 9.0 | 88.0 ± 8.0 | 88.0 ± 7.0 | 50 ± 11.0 |
| 720 min | 96.0 ± 9.0 | 96.0 ± 8.0 | 96.0 ± 7.0 | 96.0 ± 6.0 | 96.0 ± 5.0 | 96.0 ± 4.0 | 58 ± 8.0 |
| 840 min | 97.5 ± 7.5 | 97.5 ± 6.5 | 97.5 ± 5.5 | 97.5 ± 4.5 | 97.5 ± 3.5 | 97.5 ± 2.5 | 67 ± 15 |

In a particularly preferred embodiment; under in vitro conditions in 600 mL 0.1 N HCl, using the basket method according to Ph. Eur. at 75 rpm, after 1 h under physiological conditions, the pharmaceutical dosage form has released at most 50%, more preferably at most 45%, still more preferably at most 40%, yet more preferably at most 30%, even more preferably at most 28%, most preferably at most 25% and in particular at most 23% of the first pharmacologically active ingredient ($A_1$) relative to the total amount of the first pharmacologically active ingredient ($A_1$) originally contained in the pharmaceutical dosage form.

Preferably, the release profile, the first pharmacologically active ingredient ($A_1$) and optionally present pharmaceutical excipients of the formed segment ($S_1$) are stable upon storage, preferably upon storage at elevated temperature, e.g. 40° C., for 3 months in sealed containers.

In connection with the release profile "stable" preferably means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

In connection with a pharmacologically active ingredient and pharmaceutical excipients "stable" preferably means that the segments and the pharmaceutical dosage form satisfy the requirements of EMA concerning shelf-life of pharmaceutical products.

Preferably, after storage for 4 weeks, more preferably 6 months, at 40° C. and 75% rel. humidity, the content of the first pharmacologically active ingredient ($A_1$) in the formed segment(s) ($S_1$) and the pharmaceutical dosage form, respectively, amounts to at least 98.0%, more preferably at least 98.5%, still more preferably at least 99.0%, yet more preferably at least 99.2%, most preferably at least 99.4% and in particular at least 99.6%, of its original content before storage.

The formed segment(s) ($S_1$) exhibit(s) a higher breaking strength than the further segment ($S_2$). Further, the formed segment(s) ($S_1$) exhibit(s) a breaking strength of more than 500 N. When the formed segments ($S_1$) are particulate, preferably at least a fraction of the individual particles, i.e. at least one formed segment ($S_1$) has a breaking strength of more than 500 N.

Preferably, the mechanical properties, particularly the breaking strength, substantially relies on the presence and spatial distribution of the prolonged release matrix material, although its mere presence does typically not suffice in order to achieve said properties. The advantageous mechanical properties may not automatically be achieved by simply processing first pharmacologically active ingredient ($A_1$), prolonged release matrix material, and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the desired properties may be obtained only if, during preparation of the formed segment(s) ($S_1$), suitable components in suitable amounts are exposed to a sufficient pressure at a sufficient temperature for a sufficient period of time.

Thus, regardless of the apparatus used, the process protocols must be adapted in order to meet the required criteria. Therefore, the breaking strength is separable from the composition.

The formed segment(s) ($S_1$) has/have a breaking strength of more than 500 N. Preferably, the formed segment(s) ($S_1$) has/have a breaking strength of at least 600 N, more preferably at least 700 N, still more preferably at least 800 N, yet more preferably at least 1000 N, most preferably at least 1250 N and in particular at least 1500 N.

The "breaking strength" (resistance to crushing) of a pharmaceutical dosage form or a segment is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Pharmaceutical dosage forms, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture a pharmaceutical dosage form and a segment, respectively (=breaking force). Therefore, for the purpose of the specification a pharmaceutical dosage form and segment, respectively, does preferably not exhibit the desired breaking strength when it breaks, i.e., is fractured into at least two independent parts that are separated from one another. In another preferred embodiment, however, the pharmaceutical dosage form and segment, respectively, is regarded as being broken if the force decreases by 25% (threshold value) of the highest force measured during the measurement (see below).

When the pharmaceutical dosage form is a capsule, e.g. a hard gelatine capsule, the true quantitative breaking strength of the capsule is difficult to measure; it may occur that the capsule does not fracture in the course of the measurement because of its flexibility. As conventional capsules apparently to not exhibit any increased breaking strength, for the purpose of specification the quantitative breaking strength of a capsule can preferably be regarded as being 0 N.

The formed segment ($S_1$) according to the invention is distinguished from conventional pharmaceutical dosage forms and particulate or monolithic segments, respectively, in that due to its breaking strength, it cannot be pulverized by the application of force with conventional means, such as for example a pestle and mortar, a hammer, a mallet or other usual means for pulverization, in particular devices developed for this purpose (pharmaceutical dosage form crushers). In this regard "pulverization" means crumbling into small particles. Avoidance of pulverization virtually rules out oral or parenteral, in particular intravenous or nasal abuse.

Preferably, the formed segment ($S_1$) is tamper resistant and provides resistance against grinding.

Conventional pharmaceutical dosage forms and particulate or monolithic segments, respectively, typically have a breaking strength well below 200 N.

The breaking strength of conventional round pharmaceutical dosage forms/particulate or monolithic segments may be estimated according to the following empirical formula:

Breaking Strength [in N]=10×Diameter of pharmaceutical dosage form/particulate [in mm].

Thus, according to said empirical formula, a round pharmaceutical dosage form/particulate or monolithic segment having a breaking strength of at least 300 N would require a diameter of at least 30 mm. Such a particle however, could not be swallowed, let alone a pharmaceutical dosage form containing a plurality of such particles. The above empirical formula preferably does not apply to the formed segment ($S_1$) according to the invention, which is not conventional but rather special.

Further, the actual mean chewing force is about 220 N (cf., e.g., P. A. Proeschel et al., J Dent Res, 2002, 81(7), 464-468). This means that conventional pharmaceutical dosage forms and particles, respectively, having a breaking strength well below 200 N may be crushed upon spontaneous chewing, whereas the formed segment ($S_1$) according to the invention may preferably not.

Still further, when applying a gravitational acceleration of about 9.81 m/s$^2$, 300 N correspond to a gravitational force of more than 30 kg, i.e. the formed segment ($S_1$) according to the invention can preferably withstand a weight of more than 30 kg without being pulverized.

Methods for measuring the breaking strength are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Pharmaceutical dosage forms". The segments may be subjected to the same or similar breaking strength test as the pharmaceutical dosage form. The test is intended to determine, under defined conditions, the resistance to crushing of pharmaceutical dosage forms, segments and individual particles, respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the pharmaceutical dosage form, segments and individual particle, respectively. The apparatus is calibrated using a system with a precision of 1 Newton. The pharmaceutical dosage form, segment and particle, respectively, is placed between the jaws, taking into account, where applicable, the shape, the break-mark and the inscription; for each measurement the pharmaceutical dosage form, segment and particle, respectively, is oriented in the same way with respect to the direction of application of the force (and the direction of extension in which the breaking strength is to be measured). The measurement is carried out on 10 pharmaceutical dosage forms, segments and particles, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a pharmaceutical dosage form, segments and individual particles, respectively, to fail (i.e., break) in a specific plane. The pharmaceutical dosage form, segment and individual particle, respectively, is generally placed between two platens, one of which moves to apply sufficient force to the pharmaceutical dosage form, segment and individual particle, respectively, to cause fracture. For conventional, round (circular cross-section) pharmaceutical dosage form, segments and individual particles, respectively, loading occurs across their diameter (sometimes referred to as diametral loading), and fracture occurs in the plane. The breaking force of pharmaceutical dosage form, segment and individual particle, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of pharmaceutical dosage form, segments and individual particles, respectively, to the application of a compressive load. Although this term describes the true nature of the test more accurately than does hardness, it implies that pharmaceutical dosage form, segments and individual particles, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

In a preferred embodiment, the pharmaceutical dosage form, segment and individual particle, respectively, is regarded as being broken if it is fractured into at least two separate pieces.

The formed segment(s) ($S_1$) according to the invention preferably exhibit(s) mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or possibly even in liquid nitrogen), for it to be virtually impossible to pulverize by spontaneous chewing, grinding in a mortar, pounding, etc. Thus, preferably, the comparatively high breaking strength of the formed segment(s) ($S_1$) according to the invention is maintained even at low or very low temperatures, e.g., when the pharmaceutical dosage form is initially chilled to increase its brittleness, for example to temperatures below −25° C., below −40° C. or even in liquid nitrogen.

The formed segment(s) ($S_1$) according to the invention is/are characterized by a certain degree of breaking strength. This does not mean that it must also exhibit a certain degree of hardness. Hardness and breaking strength are different physical properties. Therefore, the preferred tamper-resistance of the formed segment(s) ($S_1$) does not necessarily depend on the hardness of the formed segment(s) ($S_1$). For instance, due to its breaking strength, impact strength, elasticity modulus and tensile strength, respectively, the formed segment(s) ($S_1$) can preferably be deformed, e.g. plastically, when exerting an external force, for example using a hammer, but cannot be pulverized, i.e., crumbled into a high number of fragments. In other words, the formed segment(s) ($S_1$) according to the invention is/are characterized by a certain degree of breaking strength, but not necessarily also by a certain degree of form stability.

Therefore, in the meaning of the specification, a pharmaceutical dosage form, segment and individual particle, respectively, that is deformed when being exposed to a force in a particular direction of extension but that does not break (plastic deformation or plastic flow) is preferably to be regarded as having the desired breaking strength in said direction of extension.

Preferred pharmaceutical dosage forms, segments and individual particles, respectively, are those having a suitable tensile strength as determined by a test method currently accepted in the art. Further pharmaceutical dosage form, segments and individual particles, respectively, are those having a Youngs Modulus as determined by a test method of the art. Still further pharmaceutical dosage form, segments and individual particles, respectively, are those having an acceptable elongation at break.

In a preferred embodiment, the formed segment(s) ($S_1$) is/are tamper resistant and provide(s) resistance against grinding and/or resistance against solvent extraction and/or resistance against dose-dumping in aqueous ethanol.

Tamper-resistant preferably means that the formed segment(s) ($S_1$)

(i) preferably provide(s) resistance against solvent extraction, and/or (ii) preferably provide(s) resistance against grinding, and/or (iii) preferably provide(s) resistance against dose-dumping in aqueous ethanol.

Thus, the formed segment(s) ($S_1$) according to the invention do(es) not necessarily need to exhibit any of resistances (i) to (iii); but may preferably exhibit any of resistances (i) to (iii) as well as any combination thereof; namely only (i); only (ii); only (iii); a combination of only (i) and (ii); a combination of only (i) and (iii); a combination of only (ii) and (iii); or a combination of (i) and (ii) and (iii).

Preferably, prolonged release of the first pharmacologically active ingredient ($A_1$) is achieved by a prolonged release matrix contained in the formed segment(s) ($S_1$) which prolonged release matrix additionally provides tamper resistance in terms of resistance against solvent extraction, resistance against grinding, and resistance against dose-dumping in aqueous ethanol.

As used herein, the term "tamper-resistant" refers to pharmaceutical dosage forms or segments that are resistant to conversion into a form suitable for misuse or abuse, particular for nasal and/or intravenous administration, by conventional means.

In this regard, the pharmaceutical dosage form as such it may be crushable by conventional means such as grinding in a mortar or crushing by means of a hammer. However, the formed segment(s) ($S_1$) contained in the pharmaceutical dosage form preferably exhibit(s) mechanical properties such that they cannot be pulverized by conventional means any further. As the formed segment(s) ($S_1$) is/are of macroscopic size and contain(s) the pharmacologically active ingredient, it/they cannot be administered nasally thereby rendering the pharmaceutical dosage form tamper-resistant.

Further, when trying to disrupt the pharmaceutical dosage forms by means of a hammer or mortar, the formed segments ($S_1$) tend to adhere to one another thereby forming aggregates and agglomerates, respectively, which are larger in size than the untreated particles.

Preferably, the prolonged release matrix of the formed segment(s) ($S_1$) provides resistance against solvent extraction.

Preferably, when trying to tamper the pharmaceutical dosage form in order to prepare a formulation suitable for abuse by intravenous administration, the liquid part of the formulation that can be separated from the remainder by means of a syringe at room temperature is as less as possible, preferably it contains not more than 45 or 40 wt.-%, more preferably not more than 35 wt.-%, still more preferably not more than 30 wt.-%, yet more preferably not more than 25 wt.-%, even more preferably not more than 20 wt.-%, most preferably not more than 15 wt.-% and in particular not more than 10 wt.-% of the originally contained first pharmacologically active ingredient ($A_1$).

Preferably, this property is tested by (i) dispensing a pharmaceutical dosage form that is either intact or has been manually comminuted by means of two spoons in 5 ml of solvent, either purified water or aqueous ethanol (40 vol. %), (ii) allowing the dispersion to stand for 10 min at room temperature, (iii) drawing up the hot liquid into a syringe (needle 21 G equipped with a cigarette filter), and (iv) determining the amount of the pharmacologically active ingredient contained in the liquid within the syringe.

Preferably, the prolonged release matrix of the formed segment(s) ($S_1$) contained in the pharmaceutical dosage form according to the invention provides resistance against grinding.

Preferably, when the formed segment(s) ($S_1$) is/are treated with a commercial coffee mill, preferably type Bosch MKM6000, 180 W, Typ KM13 for 2 minutes, 42±17.5 wt.-%, more preferably 42±15 wt.-%, still more preferably 42±12.5 wt.-%, yet more preferably 42±10 wt.-%, even more preferably 42±7.5 wt.-%, most preferably 42±5 wt.-%, and in particular 42±2.5 wt.-%, of the total weight of the thus obtained material does not pass a sieve having a mesh size of 1.000 mm.

Preferably, when the formed segment(s) ($S_1$) is/are treated with a commercial coffee mill, preferably type Bosch MKM6000, 180 W, Typ KM13, for 2 minutes, 57±17.5 wt.-%, more preferably 57±15 wt.-%, still more preferably 57±12.5 wt.-%, yet more preferably 57±10 wt.-%, even more preferably 57±7.5 wt.-%, most preferably 57±5 wt.-%, and in particular 57±2.5 wt.-%, of the total weight of the thus obtained material does not pass a sieve having a mesh size of 1.000 mm.

Preferably, when the formed segment(s) ($S_1$) is/are treated with a commercial coffee mill, preferably type Bosch MKM6000, 180 W, Typ KM13, for 2 minutes, at least 50 wt.-%, more preferably at least 55 wt.-%, still more preferably at least 60 wt.-%, yet more preferably at least 65 wt.-%, even more preferably at least 70 wt.-%, most preferably at least 75 wt.-%, and in particular at least 80 wt.-%, of the total weight of the thus obtained material does not pass a sieve having a mesh size of 1.000 mm.

Preferably, when the pharmaceutical dosage form treated with a commercial coffee mill, preferably type Bosch MKM6000, 180 W, Typ KM13 for 2 minutes, 42±17.5 wt.-%, more preferably 42±15 wt.-%, still more preferably 42±12.5 wt.-%, yet more preferably 42±10 wt.-%, even more preferably 42±7.5 wt.-%, most preferably 42±5 wt.-%, and in particular 42±2.5 wt.-%, of the total weight of the thus obtained material does not pass a sieve having a mesh size of 1.000 mm.

Preferably, when the pharmaceutical dosage form is/are treated with a commercial coffee mill, preferably type Bosch MKM6000, 180 W, Typ KM13, for 2 minutes, 57±17.5 wt.-%, more preferably 57±15 wt.-%, still more preferably 57±12.5 wt.-%, yet more preferably 57±10 wt.-%, even more preferably 57±7.5 wt.-%, most preferably 57±5 wt.-%, and in particular 57±2.5 wt.-%, of the total weight of the thus obtained material does not pass a sieve having a mesh size of 1.000 mm.

Preferably, when the pharmaceutical dosage form is treated with a commercial coffee mill, preferably type Bosch MKM6000, 180 W, Typ KM13, for 2 minutes, at least 50 wt.-%, more preferably at least 55 wt.-%, still more preferably at least 60 wt.-%, yet more preferably at least 65 wt.-%, even more preferably at least 70 wt.-%, most preferably at least 75 wt.-%, and in particular at least 80 wt.-%, of the total weight of the thus obtained material does not pass a sieve having a mesh size of 1.000 mm.

Particle size distributions of the ground pharmaceutical dosage form are preferably determined by sieve analysis.

In a preferred embodiment, after treatment with a commercial coffee mill as described above, more than 55%, more preferably more than 60%, still more preferably more than 65%, yet more preferably more than 70%, most preferably 75% and in particular more than 80% of the particles of the ground formed segment ($S_1$) and pharmaceutical dosage form, respectively, have a size in the range of from 0.2 to 3.3 nm, more preferably of from 0.4 to 3.1 nm, most preferably of from 0.6 to 2.9 and in particular of from 0.7 to 2.8 nm.

Preferred particle size distributions $P^1$ to $P^6$ are summarized in the table underneath:

The pharmaceutical dosage form can be tested in vitro using ethanol/simulated gastric fluid of 0%, 20% and 40% to evaluate alcohol extractability. Testing is preferably performed using standard procedures, e.g. USP Apparatus 1 (basket) or USP Apparatus 2 (paddle) at e.g. 50 rpm in e.g. 500 ml of media at 37° C., using a Perkin Elmer UV/VIS Spectrometer Lambda 20, UV at an appropriate wavelength for detection of the first pharmacologically active ingredient ($A_1$) present therein. Sample time points preferably include 0.5 and 1 hour.

Preferably, when comparing the in vitro release profile at 37° C. in simulated gastric fluid with the in vitro release profile in ethanol/simulated gastric fluid (40 vol.-%) at 37° C., the in vitro release in ethanol/simulated gastric fluid (40 vol.-%) is preferably not substantially accelerated compared to the in vitro release in simulated gastric fluid. Preferably, in this regard "substantially" means that at any given time point the in vitro release in ethanol/simulated gastric fluid (40 vol.-%) relatively deviates from the in vitro release in simulated gastric fluid by not more than +25%, more preferably not more than +20%, still more preferably not more than +15%, yet more preferably not more than +10%, even more preferably not more than +7.5%, most preferably not more than +5.0% and in particular not more than +2.5%.

A substantial relative acceleration of the in vitro release in ethanol/simulated gastric fluid (40 vol.-%) compared to the in vitro release in simulated gastric fluid is to be prevented according to the invention. However, a substantial relative deceleration of the in vitro release in ethanol/simulated gastric fluid (40 vol.-%) compared to the in vitro release in simulated gastric fluid, e.g., a relative deviation by −25% or more, may be possible and can even be desirable.

The further segment(s) ($S_2$) comprise(s) the second pharmacologically active ingredient ($A_2$) and provide immediate release thereof.

Preferably, the second pharmacologically active ingredient ($A_2$) is different from the first pharmacologically active ingredient ($A_1$).

In a preferred embodiment, the second pharmacologically active ingredient ($A_2$) exhibits no psychotropic action.

In another preferred embodiment, the second pharmacologically active ingredient ($A_2$) is selected from ATC classes [M01A], [M01C], [N02B] and [N02C] according to the WHO.

| particle size [nm] | amount [wt.-%] | | | | | |
|---|---|---|---|---|---|---|
| | $P^1$ | $P^2$ | $P^3$ | $P^4$ | $P^5$ | $P^6$ |
| <0.045 | 0.5 ± 0.4 | 0.1 ± 0.09 | 0.3 ± 0.29 | 0.3 ± 0.29 | 0.3 ± 0.29 | 0.3 ± 0.29 |
| 0.045-0.063 | 0.5 ± 0.4 | 0.3 ± 0.29 | 0.3 ± 0.29 | 0.3 ± 0.29 | 0.3 ± 0.29 | 0.3 ± 0.29 |
| 0.063-0.090 | 0.5 ± 0.4 | 0.3 ± 0.29 | 0.3 ± 0.29 | 1.0 ± 0.9 | 0.3 ± 0.29 | 0.3 ± 0.29 |
| 0.090-0.125 | 0.5 ± 0.4 | 0.3 ± 0.29 | 0.3 ± 0.29 | 1.0 ± 0.9 | 0.3 ± 0.29 | 1.0 ± 0.9 |
| 0.125-0.180 | 0.5 ± 0.4 | 3.0 ± 2.9 | 2.0 ± 1.5 | 2.0 ± 1.5 | 1.0 ± 0.9 | 1.0 ± 0.9 |
| 0.180-0.250 | 1.5 ± 1.4 | 1.0 ± 0.8 | 2.0 ± 1.5 | 1.0 ± 0.9 | 2.0 ± 1.5 | 1.0 ± 0.9 |
| 0.250-0.355 | 4.0 ± 3.5 | 5.0 ± 4.0 | 4.0 ± 3.5 | 3.5 ± 2.5 | 5.0 ± 4.0 | 3.0 ± 2.9 |
| 0.355-0.500 | 7.0 ± 6.0 | 5.0 ± 4.0 | 6.0 ± 4.5 | 7.0 ± 6.0 | 7.0 ± 6.0 | 7.0 ± 6.0 |
| 0.500-0.710 | 11.0 ± 8.0 | 9.0 ± 7.0 | 11.0 ± 8.0 | 10.0 ± 7.0 | 13.0 ± 10.0 | 9.0 ± 7.0 |
| 0.710-1.000 | 15.0 ± 12.0 | 10.0 ± 7.0 | 17.0 ± 14.0 | 18.0 ± 15.0 | 18.0 ± 15.0 | 13.0 ± 10.0 |
| 1.000-1.400 | 20.0 ± 17.0 | 18.0 ± 15.0 | 23.0 ± 20.0 | 28.0 ± 25.0 | 25.0 ± 22.0 | 20.0 ± 17.0 |
| 1.400-2.000 | 23.0 ± 20.0 | 19.0 ± 16.0 | 12.0 ± 9.0 | 18.0 ± 15.0 | 10.0 ± 7.0 | 22.0 ± 19.0 |
| 2.000-2.800 | 13.0 ± 10.0 | 16.0 ± 13.0 | 13.0 ± 10.0 | 11.0 ± 8.0 | 14.0 ± 11.0 | 12.0 ± 9.0 |
| 2.800-4.000 | 1.0 ± 0.8 | 14.0 ± 11.0 | 12.0 ± 9.0 | 0.3 ± 0.29 | 4.0 ± 3.5 | 9.0 ± 7.0 |
| >4.00 | 0.5 ± 0.45 | 0.3 ± 0.29 | 0.3 ± 0.29 | 0.5 ± 0.45 | 0.3 ± 0.29 | 0.5 ± 0.45 |

Preferably, the prolonged release matrix of the formed segment(s) ($S_1$) contained in the pharmaceutical dosage form according to the invention provides resistance against dose-dumping in aqueous ethanol.

In a particularly preferred embodiment, (i) the first pharmacologically active ingredient ($A_1$) has a psychotropic effect; and/or (ii) the second pharmacologically active ingredient ($A_2$) is selected from ATC classes [M01A], [M01C], [N02B] and [N02C] according to the WHO.

Preferably, the second pharmacologically active ingredient ($A_2$) is selected from the group consisting of acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, phenazone, metamizole sodium, aminophenazone, propyphenazone, nifenazone, paracetamol, phenacetin, bucetin, propacetamol, rimazolium, glafenine, floctafenine, viminol, nefopam, flupirtine, ziconotide, methoxyflurane, nabiximols, dihydroergotamine, ergotamine, methysergide, lisuride, flumedroxone, sumatriptan, naratriptan, zolmitriptan, rizatriptan, almotriptan, eletriptan, frovatriptan, pizotifen, clonidine, iprazochrome, dimetotiazine, oxetorone, phenylbutazone, mofebutazone, oxyphenbutazone, clofezone, kebuzone, indomethacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lornoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, naproxcinod, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, oxycinchophen, sodium aurothiomalate, sodium aurotiosulfate, auranofin, aurothioglucose, aurotioprol, penicillamine, bucillamine, their physiologically acceptable salts, as well as mixtures thereof.

In a preferred embodiment, the second pharmacologically active ingredient ($A_2$) is paracetamol (acetaminophen) or ibuprofen, more preferably paracetamol.

In a particularly preferred embodiment, the first pharmacologically active ingredient ($A_1$) is hydrocodone or a physiologically acceptable salt thereof and the second pharmacologically active ingredient ($A_2$) is paracetamol.

Preferred combinations $C^1$ to $C^{32}$ of the first pharmacologically active ingredient ($A_1$) and the second pharmacologically active ingredient ($A_2$) are summarized in the table here below, wherein the first pharmacologically active ingredient ($A_1$) as well as the second pharmacologically active ingredient ($A_2$) each also refer to the physiologically acceptable salts thereof, particularly to the hydrochlorides:

|  | $A_1$ | $A_2$ |
| --- | --- | --- |
| $C^1$ | oxycodone | ibuprofen |
| $C^2$ | oxymorphone | ibuprofen |
| $C^3$ | hydrocodone | ibuprofen |
| $C^4$ | hydromorphone | ibuprofen |
| $C^5$ | morphine | ibuprofen |
| $C^6$ | tapentadol | ibuprofen |
| $C^7$ | tramadol | ibuprofen |
| $C^8$ | buprenorphine | ibuprofen |
| $C^9$ | oxycodone | paracetamol |
| $C^{10}$ | oxymorphone | paracetamol |
| $C^{11}$ | hydrocodone | paracetamol |
| $C^{12}$ | hydromorphone | paracetamol |
| $C^{13}$ | morphine | paracetamol |
| $C^{14}$ | tapentadol | paracetamol |
| $C^{15}$ | tramadol | paracetamol |
| $C^{16}$ | buprenorphine | paracetamol |
| $C^{17}$ | oxycodone | diclofenac |
| $C^{18}$ | oxymorphone | diclofenac |
| $C^{19}$ | hydrocodone | diclofenac |
| $C^{20}$ | hydromorphone | diclofenac |
| $C^{21}$ | morphine | diclofenac |
| $C^{22}$ | tapentadol | diclofenac |
| $C^{23}$ | tramadol | diclofenac |
| $C^{24}$ | buprenorphine | diclofenac |
| $C^{25}$ | oxycodone | acetylsalicylic acid |
| $C^{26}$ | oxymorphone | acetylsalicylic acid |
| $C^{27}$ | hydrocodone | acetylsalicylic acid |
| $C^{28}$ | hydromorphone | acetylsalicylic acid |
| $C^{29}$ | morphine | acetylsalicylic acid |
| $C^{30}$ | tapentadol | acetylsalicylic acid |
| $C^{31}$ | tramadol | acetylsalicylic acid |
| $C^{32}$ | buprenorphine | acetylsalicylic acid |

The second pharmacologically active ingredient ($A_2$) is present in the pharmaceutical dosage form in a therapeutically effective amount. In general, the amount that constitutes a therapeutically effective amount varies according to the pharmacologically active ingredients being used, the condition being treated, the severity of said condition, the patient being treated, and whether the pharmaceutical dosage form or the segment in which the pharmacologically active ingredient is contained is designed for an immediate or retarded release.

The total content of the second pharmacologically active ingredient ($A_2$) preferably ranges from about 0.01 wt.-% to about 95 wt.-%, more preferably from about 0.1 wt.-% to about 80 wt.-%, even more preferably from about 1.0 wt.-% to about 50 wt.-%, yet more preferably from about 1.5 wt.-% to about 30 wt.-%, and most preferably from about 2.0 wt.-% to 20 wt.-%, based on the total weight of the further segment(s) ($S_2$) or based on the total weight of the pharmaceutical dosage form.

Preferably, the total content of the second pharmacologically active ingredient ($A_2$) is within the range of from 0.01 to 80 wt.-%, more preferably 0.1 to 50 wt.-%, still more preferably 1 to 25 wt.-%, based on the total weight of the pharmaceutical dosage form. In a preferred embodiment, the total content of the second pharmacologically active ingredient ($A_2$) is within the range of from 20±15 wt.-%, more preferably 20±12 wt.-%, still more preferably 20±10 wt.-%, most preferably 20±7 wt.-%, and in particular 20±5 wt.-%, based on the total weight of the pharmaceutical dosage form. In a preferred embodiment, the total content of the second pharmacologically active ingredient ($A_2$) is within the range of from 30±15 wt.-%, more preferably 30±12 wt.-%, still more preferably 30±10 wt.-%, most preferably 30±7 wt.-%, and in particular 30±5 wt.-%, based on the total weight of the pharmaceutical dosage form. In a preferred embodiment, the total content of the second pharmacologically active ingredient ($A_2$) is within the range of from 40±15 wt.-%, more preferably 40±12 wt.-%, still more preferably 40±10 wt.-%, most preferably 40±7 wt.-%, and in particular 40±5 wt.-%, based on the total weight of the pharmaceutical dosage form. In a preferred embodiment, the total content of the second pharmacologically active ingredient ($A_2$) is within the range of from 50±15 wt.-%, more preferably 50±12 wt.-%, still more preferably 50±10 wt.-%, most preferably 50±7 wt.-%, and in particular 50±5 wt.-%, based on the total weight of the pharmaceutical dosage form. In a preferred embodiment, the total content of the second pharmacologically active ingredient ($A_2$) is within the range of from 60±15 wt.-%, more preferably 60±12 wt.-%, still more preferably 60±10 wt.-%, most preferably 60±7 wt.-%, and in particular 60±5 wt.-%, based on the total weight of the pharmaceutical dosage form.

Preferably, the total content of the second pharmacologically active ingredient ($A_2$) is within the range of from 0.01 to more than 99.99 wt.-%, more preferably 0.1 to 99.9 wt.-%, still more preferably 5 to 95 wt.-%, based on the total weight of the further segment(s) ($S_2$). In a preferred embodiment, the total content of the second pharmacologically active ingredient ($A_2$) is within the range of from 20±6 wt.-%, 30±6 wt.-% or 40±6 wt.-%, more preferably 20±5 wt.-%, 30±5 wt.-% or 40±5 wt.-%, still more preferably 20±4 wt.-%, 30±4 wt.-% or 40±4 wt.-%, most preferably 20±3 wt.-%, 30±3 wt.-% or 40±3 wt.-% and in particular 20±2 wt.-%, 30±2 wt.-% or 40±2 wt.-%, based on the total weight of the further segment(s) ($S_2$). In another preferred embodiment, the total content of the second pharmacologically active ingredient ($A_2$) is within the range of from 50±20 wt.-%, 60±20 wt.-%, 70±20 wt.-% or 80±20 wt.-%, more preferably 50±15 wt.-%, 60±15 wt.-%, 70±15 wt.-% or 80±15 wt.-%, still more preferably 50±12 wt.-%, 60±12 wt.-%, 70±12 wt.-% or 80±12 wt.-%, most preferably 50±10 wt.-%, 60±10 wt.-%, 70±10 wt.-% or 80±10 wt.-%, and in particular 50±5 wt.-%, 60±5 wt.-%, 70±5 wt.-% or 80±5 wt.-%, based on the total weight of the further segment(s) ($S_2$). In still another preferred embodiment, the total content of the second pharmacologically active ingredient ($A_2$) is within the range of from 90±10 wt.-%, more preferably 90±8 wt.-%, still more preferably 90±6 wt.-%, most preferably 90±4 wt.-% and in particular 90±2 wt.-%, based on the total weight of the further segment(s) ($S_2$).

The total amount of the second pharmacologically active ingredient ($A_2$) in the further segment ($S_2$) and the pharmaceutical dosage form, respectively, is not limited. The total amount of the second pharmacologically active ingredient ($A_2$) which is adapted for administration preferably is in the range of 0.1 mg to 2,000 mg or 0.1 mg to 1,000 mg or 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the second pharmacologically active ingredient ($A_2$) which is contained in the further segment ($S_2$) and the pharmaceutical dosage form, respectively, is within the range of from 10 to 1,000 mg, more preferably 50 to 900 mg, still more preferably 100 to 800 mg, yet more preferably 200 to 600 mg, most preferably 250 to 500 mg and in particular 300 to 400 mg. In another preferred embodiment, the total amount of the second pharmacologically active ingredient ($A_2$) which is contained in the further segment ($S_2$) and the pharmaceutical dosage form, respectively, is within the range of from 10 to 500 mg, more preferably 12 to 450 mg, still more preferably 14 to 400 mg, yet more preferably 16 to 350 mg, most preferably 18 to 325 mg and in particular 20 to 300 mg.

In a preferred embodiment, the second pharmacologically active ingredient ($A_2$) is contained in the further segment(s) ($S_2$) and the pharmaceutical dosage form, respectively, in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, 160±5 mg, 170±5 mg, 180±5 mg, 190±5 mg, 200±5 mg, 210±5 mg, 220±5 mg, 230±5 mg, 240±5 mg, or 250±5 mg. In another preferred embodiment, the second pharmacologically active ingredient ($A_2$) is contained in the further segment(s) ($S_2$) and the pharmaceutical dosage form, respectively, in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, 160±2.5 mg, 165±2.5 mg, 170±2.5 mg, 175±2.5 mg, 180±2.5 mg, 185±2.5 mg, 190±2.5 mg, 195±2.5 mg, 200±2.5 mg, 205±2.5 mg, 210±2.5 mg, 215±2.5 mg, 220±2.5 mg, 225±2.5 mg, 230±2.5 mg, 235±2.5 mg, 240±2.5 mg, 245±2.5 mg, or 250±2.5 mg. In still another preferred embodiment, the second pharmacologically active ingredient ($A_2$) is contained in the further segment(s) ($S_2$) and the pharmaceutical dosage form, respectively, in an amount of 250±10 mg, 275±10 mg, 300±10 mg, 325±10 mg, 350±10 mg, 375±10 mg, 400±10 mg, 425±10 mg, 450±10 mg, 475±10 mg, 500±10 mg, 525±10 mg, 550±10 mg, 575±10 mg or 600±10 mg.

In a particularly preferred embodiment, the second pharmacologically active ingredient ($A_2$) is paracetamol (acetaminophen). In this embodiment, the paracetamol is preferably contained in the further segment(s) ($S_2$) or the pharmaceutical dosage form in an amount of from 100 to 600 mg, more preferably 150 to 550 mg, still more preferably 200 to 500 mg, most preferably 250 to 450 mg and in particular 275 to 400 mg.

In another particularly preferred embodiment, the second pharmacologically active ingredient ($A_2$) is ibuprofen. In this embodiment, the ibuprofen is preferably contained in the further segment(s) ($S_2$) or the pharmaceutical dosage form in an amount of from 100 to 600 mg, more preferably 150 to 550 mg, still more preferably 200 to 500 mg, most preferably 250 to 450 mg and in particular 275 to 400 mg.

In a preferred embodiment, the relative weight ratio of the total content of the first pharmacologically active ingredient ($A_1$) to the total content of the second pharmacologically active ingredient ($A_2$) [$A_1$:$A_2$] is within the range of (8±1):1, more preferably (7±1):1, still more preferably (6±1):1, yet more preferably (5±1):1, even more preferably (4±1):1, most preferably (3±1):1 and in particular (2±1):1.

In still another preferred embodiment, the relative weight ratio of the total content of the second pharmacologically active ingredient ($A_2$) to the total content of the first pharmacologically active ingredient ($A_1$) [$A_2$:$A_1$] is within the range of (8±1):1, more preferably (7±1):1, still more preferably (6±1):1, yet more preferably (5±1):1, even more preferably (4±1):1, most preferably (3±1):1 and in particular (2±1):1.

The further segment(s) ($S_2$) provide(s) immediate release of the second pharmacologically active ingredient ($A_2$).

Preferably, under physiological conditions the pharmaceutical dosage form has released after 5 minutes at least 10%, after 10 minutes at least 20%, after 15 minutes at least 30%, after 20 minutes at least 40%, after 30 minutes at least 60%, after 40 minutes at least 70%, after 50 minutes at least 80%, after 60 minutes at least 90% or 99% of the second pharmacologically active ingredient ($A_2$).

Suitable in vitro conditions are known to the skilled artisan. In this regard it can be referred to, e.g., the Eur. Ph. Preferably, the release profile is measured under the following conditions: Paddle apparatus equipped without sinker, 50 rpm, 37±5° C., 600 mL simulated intestinal fluid pH 6.8 (phosphate buffer) or pH 4.5. In a preferred embodiment, the rotational speed of the paddle is increased to 75 rpm. In another preferred embodiment, the release profile is determined under the following conditions: basket method, 75 rpm, 37±5° C., 600 mL 0.1 N HCl or 600 mL of SIF sp (pH 6.8) or 600 mL of 0.1 NHCl+40% ethanol.

In a particularly preferred embodiment; under in vitro conditions in 600 mL 0.1 N HCl, using the basket method according to Ph. Eur. at 75 rpm, after 1 h under physiological conditions the pharmaceutical dosage form has released at least 60% more preferably at least 65%, still more preferably at least 70%, yet more preferably at least 75%, even more preferably at least 80%, most preferably at least 85% and in particular at least 90% or at least 95% or at least 99% of the second pharmacologically active ingredient ($A_2$) relative to the total amount of $A_2$ originally contained in the pharmaceutical dosage form.

Preferably, the content of the further segment(s) ($S_2$) is at least 2.5 wt.-%, at least 5 wt.-%, at least 7.5 wt.-% or at least 10 wt.-%; at least 12.5 wt.-%, at least 15 wt.-%, at least 17.5 wt.-% or at least 20 wt.-%; at least 22.5 wt.-%, at least 25 wt.-%, at least 27.5 wt.-% or at least 30 wt.-%; at least 32.5 wt.-%, at least 35 wt.-%, at least 37.5 wt.-% or at least 40 wt.-%; more preferably at least 42.5 wt.-%, at least 45 wt.-%, at least 47.5 wt.-% or at least 50 wt.-%; still more preferably at least 52.5 wt.-%, at least 55 wt.-%, at least 57.5 wt.-% or at least 60 wt.-%; yet more preferably at least 62.5 wt.-%, at least 65 wt.-%, at least 67.5 wt.-% or at least 60 wt.-%; most preferably at least 72.5 wt.-%, at least 75 wt.-%, at least 77.5 wt.-% or at least 70 wt.-%; and in particular at least 82.5 wt.-%, at least 85 wt.-%, at least 87.5 wt.-% or at least 90 wt.-%; based on the total weight of the pharmaceutical dosage form.

Preferably, the content of the further segment(s) ($S_2$) is at most 90 wt.-%, at most 87.5 wt.-%, at most 85 wt.-%, or at most 82.5 wt.-%; more preferably at most 80 wt.-%, at most 77.5 wt.-%, at most 75 wt.-% or at most 72.5 wt.-%; still more preferably at most 70 wt.-%, at most 67.5 wt.-%, at most 65 wt.-% or at most 62.5 wt.-%; yet more preferably at most 60 wt.-%, at most 57.5 wt.-%, at most 55 wt.-% or at most 52.5 wt.-%; most preferably at most 50 wt.-%, at most 47.5 wt.-%, at most 45 wt.-% or at most 42.5 wt.-%; and in particular at most 40 wt.-%, at most 37.5 wt.-%, or at most 35 wt.-%; based on the total weight of the pharmaceutical dosage form.

Preferably, the relative weight ratio of the formed segment(s) ($S_1$) to the further segment(s) ($S_2$) in the pharmaceutical dosage form is from 1:10 to 10:1, more preferably 1:8 to 8:1, still more preferably 1:7 to 6:1, even more preferably 1:6 to 5:1, yet more preferably 1:5 to 4:1, most preferably 1:4 to 3:1 and in particular 1:3 to 2:1 or 1:2 to 1:1, based on the total weight of the formed segment(s) ($S_1$) and on the total weight of the further segments ($S_2$).

The further segment(s) ($S_2$) may optionally comprise conventional pharmaceutical excipients.

Preferably, the further segment(s) ($S_2$) comprise(s) one or more fillers or binders. As many fillers can be regarded as binders and vice versa, for the purpose of the specification "filler/binder" refers to any excipient that is suitable as filler, binder or both. Thus, the further segment(s) ($S_2$) preferably comprise(s) a filler/binder.

Preferred fillers (=filler/binders) are selected from the group consisting of silicium dioxide (e.g. Aerosil®), microcrystalline cellulose (e.g. Avicel®, Elcema®, Emocel®, ExCel®) Vitacell®; cellulose ether (e.g. Natrosol®, Klucel®, Methocel®, Blanose®, Pharmacoat®, Viscontran®); mannitol; dextrines; dextrose; calciumhydrogen phosphate (e.g. Emcompress®); tricalcium phosphate, maltodextrine (e.g. Emdex®); lactose (e.g. Fast-Flow Lactose®; Ludipress®, Pharmaceutical dosage Formtose®, Zeparox®); polyvinylpyrrolidone (PVP) (e.g. Kollidone®, Polyplasdone®, Polydone®); saccharose (e.g. Nu-Tab®, Sugar Tab®); magnesium salts (e.g. $MgCO_3$, MgO, $MgSiO_3$); starches and pretreated starches (e.g. Prejel®, Primotab® ET, Starch® 1500). Preferred binders are selected from the group consisting of alginates; chitosanes; and any of the fillers mentioned above (=fillers/binders).

Some fillers/binders may also serve other purposes. It is known, for example, that silicium dioxide exhibits excellent function as a glidant. Preferably, the further segment(s) ($S_2$) comprise(s) a glidant such as silicium dioxide.

In a preferred embodiment, the content of the filler/binder or mixture of fillers/binders in the further segment(s) ($S_2$) is within the range of 50±25 wt.-%, more preferably 50±20 wt.-%, still more preferably 50±15 wt.-%, yet more preferably 50±10 wt.-%, most preferably 50±7.5 wt.-%, and in particular 50±5 wt.-%, based on the total weight of further segment(s) ($S_2$). In another preferred embodiment, the content of the filler/binder or mixture of fillers/binders in the further segment(s) ($S_2$) is within the range of 65±25 wt.-%, more preferably 65±20 wt.-%, still more preferably 65±15 wt.-%, yet more preferably 65±10 wt.-%, most preferably 65±7.5 wt.-%, and in particular 65±5 wt.-%, based on the total weight of further segment(s) ($S_2$). In still another preferred embodiment, the content of the filler/binder or mixture of fillers/binders in further segment(s) ($S_2$) is within the range of 80±19 wt.-%, more preferably 80±17.5 wt.-%, still more preferably 80±15 wt.-%, yet more preferably 80±10 wt.-%, most preferably 80±7.5 wt.-%, and in particular 80±5 wt.-%, based on the total weight of further segment(s) ($S_2$). In another preferred embodiment, the content of the filler/binder or mixture of fillers/binders in the further segment(s) ($S_2$) is within the range of 90±9 wt.-%, more preferably 90±8 wt.-%, still more preferably 90±7 wt.-%, yet more preferably 90±6 wt.-%, most preferably 90±5 wt.-%, and in particular 90±4 wt.-%, based on the total weight of further segment(s) ($S_2$).

In a preferred embodiment, the total content of the filler/binder or mixture of fillers/binders in the pharmaceutical dosage form is within the range of 25±24 wt.-%, more preferably 25±20 wt.-%, still more preferably 25±16 wt.-%, yet more preferably 25±12 wt.-%, most preferably 25±8 wt.-%, and in particular 25±4 wt.-%, based on the total weight of pharmaceutical dosage form. In another preferred embodiment, the total content of the filler/binder or mixture of fillers/binders in the pharmaceutical dosage form is within the range of 30±29 wt.-%, more preferably 30±25 wt.-%, still more preferably 30±20 wt.-%, yet more preferably 30±15 wt.-%, most preferably 30±10 wt.-%, and in particular 30±5 wt.-%, based on the total weight of pharmaceutical dosage form. In still another preferred embodiment, the total content of the filler/binder or mixture of fillers/binders in the pharmaceutical dosage form is within the range of 35±34 wt.-%, more preferably 35±28 wt.-%, still more preferably 35±22 wt.-%, yet more preferably 35±16 wt.-%, most preferably 35±10 wt.-%, and in particular 35±4 wt.-%, based on the total weight of pharmaceutical dosage form. In another preferred embodiment, the total content of the filler/binder or mixture of fillers/binders in the pharmaceutical dosage form is within the range of 40±39 wt.-%, more preferably 40±32 wt.-%, still more preferably 40±25 wt.-%, yet more preferably 40±18 wt.-%, most preferably 40±11 wt.-%, and in particular 40±4 wt.-%, based on the total weight of pharmaceutical dosage form.

Preferably, the filler/binder is contained in the further segment(s) ($S_2$) but not in the formed segment(s) ($S_1$) of the pharmaceutical dosage form according to the invention.

Preferably, the further segment(s) ($S_2$) comprise(s) one or more diluents or lubricants, preferably selected from the group consisting of calcium stearate; magnesium stearate; glycerol monobehenate (e.g. Compritol®); Myvatex®; Precirol®; Precirol® Ato5; sodium stearylfumarate (e.g. Pruv®); and talcum. Magnesium stearate is particularly preferred. Preferably, the content of the lubricant in the further segment(s) ($S_2$) is at most 10.0 wt.-%, more preferably at most 7.5 wt.-%, still more preferably at most 5.0 wt.-%, yet more preferably at most 2.0 wt.-%, even more preferably at most 1.0 wt.-%, and most preferably at most 0.5 wt.-%, based on the total weight of the further segment(s) ($S_2$) or based on the total weight of pharmaceutical dosage form.

Preferably, the further segment(s) ($S_2$) comprise(s) one or more disintegrants, preferably selected from the group consisting of carmellose and salts thereof, croscarmellose sodium, crospovidone, sodium carboxymethyl starch, sodium starch glycolate, partly pregelatinized starch and low-substituted hydroxypropyl cellulose. Crosscarmellose is particularly preferred. Preferably, the content of the disintegrant in the further segment(s) ($S_2$) is at most 20.0 wt.-%, more preferably at most 15 wt.-%, still more preferably at most 12.5 wt.-%, yet more preferably at most 10 wt.-%, even more preferably at most 8.0 wt.-%, and most preferably within the range of from 6.0 wt.-% to 8.0 wt.-%, based on the total weight of the further segment(s) ($S_2$) or based on the total weight of pharmaceutical dosage form.

Preferably, the further segment(s) ($S_2$) comprise(s) one or more dispersing agents or a wetting agents, preferably selected from the group consisting of poloxamers such as Lutrol F68. Preferably, the content of the dispersing agent or a wetting agent in the further segment(s) ($S_2$) is at most 50 wt.-%, more preferably at most 45 wt.-%, still more preferably at most 40 wt.-%, yet more preferably at most 35 wt.-%, even more preferably at most 30 wt.-%, and most preferably within at most 30 wt.-%, based on the total weight of the further segment(s) ($S_2$) or based on the total weight of pharmaceutical dosage form.

In particularly preferred embodiment, the further segment(s) ($S_2$) comprise(s) a combination of filler/binder and lubricant and optionally disintegrant and optionally dispersing agent/wetting agent.

The further segment(s) ($S_2$) of the pharmaceutical dosage form according to the invention may additionally contain other excipients that are conventional in the art, e.g. diluents, binders, granulating aids, colorants, flavourants, glidants, wet-regulating agents and disintegrants. The skilled person will readily be able to determine appropriate quantities of each of these excipients.

In a preferred embodiment, however, besides the second pharmacologically active ingredient ($A_2$), the further segment(s) ($S_2$) of the pharmaceutical dosage form according to the invention consists of one or more disintegrants, one or more filler/binder's and one or more lubricants, but does not contain any other constituents.

In a particularly preferred embodiment, the further segment(s) ($S_2$) of the pharmaceutical dosage form according to the invention do(es) not contain one or more gel-forming agents and/or a silicone.

In a preferred embodiment, the further segment(s) ($S_2$) of the pharmaceutical dosage form according to the invention do(es) not contain polyalkylene oxides, acrylic polymers or waxy materials. If the further segment(s) ($S_2$) contain(s) polyalkylene oxides, acrylic polymers and/or waxy materials, the total content of polyalkylene oxides, acrylic polymers and waxy materials preferably is not more than 30 wt.-%, more preferably not more than 25 wt.-%, still more preferably not more than 20 wt.-%, yet more preferably not more than 15 wt.-%, even more preferably not more than 10 wt.-%, most preferably not more than 5.0 wt.-%, and in particular not more than 1.0 wt.-%, relative to the total weight of the further segment(s) ($S_2$).

As used herein the term "gel-forming agent" is used to refer to a compound that, upon contact with a solvent (e.g. water), absorbs the solvent and swells, thereby forming a viscous or semi-viscous substance. Preferred gel-forming agents are not cross-linked. This substance may moderate pharmacologically active ingredient release from the embedded particulates in both aqueous and aqueous alcoholic media. Upon full hydration, a thick viscous solution or dispersion is typically produced that significantly reduces and/or minimizes the amount of free solvent which can contain an amount of solubilized pharmacologically active ingredient, and which can be drawn into a syringe. The gel that is formed may also reduce the overall amount of pharmacologically active ingredient extractable with the solvent by entrapping the pharmacologically active ingredient within a gel structure. Thus the gel-forming agent may play an important role in conferring tamper-resistance to the pharmaceutical dosage forms according to the invention.

Gel-forming agents that preferably are not contained in the further segment(s) ($S_2$) include pharmaceutically acceptable polymers, typically hydrophilic polymers, such as hydrogels. Representative examples of gel-forming agent include polyalkylene oxide such as polyethylene oxide, polyvinyl alcohol, hydroxypropylmethyl cellulose, carbomers, poly(uronic) acids and mixtures thereof.

The optional excipients preferably do not impart to the further segment(s) ($S_2$) any significant resistance against dose-dumping in aqueous ethanol. According to this embodiment, the further segment(s) ($S_2$) preferably do(es) not contain any compound which would impart to the further segment(s) ($S_2$) any substantial resistance against dose-dumping in aqueous ethanol such as polyalkylene oxides, nonionic acrylic polymers or waxy materials.

The formed segment(s) ($S_1$) may be incorporated in an outer matrix material formed by the further segment(s) ($S_2$). From a macroscopic perspective, the outer matrix material formed by the further segment(s) ($S_2$) preferably forms a continuous phase in which the formed segment(s) ($S_1$) is/are embedded. When the formed segments ($S_1$) are particulate, the particles preferably form a discontinuous phase within an outer matrix material that is formed by further segment ($S_2$).

For the purpose of definition, the "outer matrix material" is preferably the further segment ($S_2$) and thus, preferably comprises the second pharmacologically active ingredient ($A_2$) and optionally conventional pharmaceutical excipients which have already been described above.

In a preferred embodiment, the further segment(s) ($S_2$) essentially consist(s) of the second pharmacologically active ingredient ($A_2$), i.e. the further segment(s) ($S_2$) do(es) not comprise any pharmaceutical excipient. According to this embodiment, the pharmaceutical dosage form is preferably a capsule that is filled with the formed segment(s) ($S_1$) and the second pharmacologically active ingredient ($A_2$), which may be powdery or agglomerated, e.g. granulated, and which preferably forms a further segment ($S_2$) as an outer matrix material.

Preferably, the outer matrix material is a homogenous powdery or coherent mass, preferably a homogeneous mixture of solid constituents, in which the monolithic or particulate formed segment(s) ($S_1$) is/are embedded. According to this embodiment, when the formed segment ($S_1$) is particulate, the particulate formed segments ($S_1$) are preferably spatially separated from one another. While it is possible that the surfaces of particulate formed segments ($S_1$) are in contact or at least in very close proximity with one another, the plurality of particulate formed segments ($S_1$) preferably cannot be regarded as a single continuous coherent mass within the pharmaceutical dosage form.

In other words, when the formed segments ($S_1$) are particulate and the particles are contained in an outer matrix material formed by the further segments ($S_2$), the pharmaceutical dosage form according to the invention preferably comprises the particles of the formed segment ($S_1$) as volume elements of a first type and the outer matrix material formed by the further segment ($S_2$) as volume element of a second type differing from the material that forms the particles of the formed segment ($S_1$), and preferably containing no prolonged release matrix.

When the formed segment(s) ($S_1$) is/are contained in an outer matrix material formed by the further segment ($S_2$), the relative weight ratio of the monolith or the particles of the formed segment(s) ($S_1$) to the outer matrix material is not particularly limited. Preferably, said relative weight ratio is within the range of 1:2.00±1.75, more preferably 1:2.00±1.50, still more preferably 1:1.00±1.00, most preferably 1:1.00±0.75, and in particular 1:1.00±0.50.

The further segment ($S_2$) in turn may also be in particulate form. When the further segment ($S_2$) is particulate form, however, the particles are preferably not thermoformed and preferably do not contain synthetic or natural polymer (C). When the further segment ($S_2$) is in particulate form, the particles are preferably obtained by conventional methods for the preparation of aggregates and agglomerates from powder mixtures such as granulating and compacting.

The further segment(s) ($S_2$) exhibit(s) a breaking strength that is lower than that of formed segment(s) ($S_1$). Typically, the breaking strength of further segment(s) is not increased compared to the breaking strength of conventional dosage forms, i.e. well below 200 N. When the further segment(s) ($S_2$) are powdery, the "breaking strength" of the powder is so low that it cannot be measured by conventional means. Thus, for the purpose of specification, the breaking strength of the powder should be regarded as "0 Newton". When quantifying the breaking strength of the further segment(s) ($S_2$) by "0 Newton", the further segment(s) is/are typically present in form of a (free-flowing) powder, and when quantifying the breaking strength of the further segment(s) ($S_2$) by values above "0 Newton", this implies that according to these embodiments the further segment(s) ($S_2$) is/are at least to some minimal degree present in form of granulated, compacted, congealed or otherwise agglomerated matter, but not as a (free-flowing) powder.

In a preferred embodiment, the further segment(s) ($S_2$) exhibit(s) a breaking strength within the range of from 0 N to at most 500 N. Preferably, the further segment(s) ($S_2$) exhibit(s) a breaking strength within the range of from 0 N to 450 N, more preferably 0 N to 400 N, still more preferably 0 N to 350 N, yet more preferably 0 N to 300 N, most preferably 0 N to 250 N and in particular 0 N to 200 N.

The at least one formed segment ($S_1$) of the pharmaceutical dosage form exhibits a higher breaking strength than the at least one further segment ($S_2$) of the pharmaceutical dosage form.

Preferably, the breaking strength of the formed segment(s) ($S_1$) is relatively at least 50 N higher, more preferably at least 100 N higher, still more preferably at least 150 N higher, yet more preferably at least 200 N higher, even more preferably at least 250 N higher, most preferably at least 300 N higher, and in particular at least 350 N higher than the breaking strength of the further segment(s) ($S_2$).

In a preferred embodiment, the further segment ($S_2$) exhibits a breaking strength of at most 500 N, more preferably at most 300 N, still more preferably at most 250 N, yet more preferably at most 200 N, even more preferably at most 150 N, most preferably at most 100 N, and in particular at most 50 N.

According to this embodiment, the second pharmacologically active ingredient ($A_2$) preferably does not have potential for being abused; more preferably, the second pharmacologically active ingredient ($A_2$) is selected from ATC classes [M01A], [M01C], [N02B] and [N02C] according to the WHO; and most preferably, the second pharmacologically active ingredient ($A_2$) is selected from paracetamol and ibuprofen.

In general, it is very difficult to provide any segment exhibiting a high breaking strength, preferably such a high breaking strength that crushing of the segment is impeded, while at the same time providing immediate release of a pharmacologically active ingredient contained in said segment. This is because the breaking strength typically relies on the presence of polymers that act as release matrix material slowing down the release of the pharmacologically active ingredient. Therefore, it is only meaningful to provide a segment exhibiting a combination of a high breaking strength and immediate release of the pharmacologically active ingredient contained therein when said pharmacologically active ingredient has a potential for being abused.

In a preferred embodiment,
(i) the formed segment ($S_1$) exhibits a breaking strength of preferably at least 750 N, more preferably at least 1000 N, most preferably at least 1250 N, and in particular at least 1500 N; and/or
(ii) the further segment ($S_2$) exhibits a breaking strength of at most 500 N, more preferably at most 300 N, still more preferably at most 250 N, yet more preferably at most 200 N, even more preferably at most 150 N, most preferably at most 100 N, and in particular at most 50 N.

Because of the different breaking strength of the formed segment(s) ($S_1$) and the further segment(s) ($S_2$), when measuring the breaking strength of the pharmaceutical dosage form according to the invention, a distance-to-force diagram can be obtained that contains at least two steps; the first platform in the distance-to-force diagram is reached once the further segment(s) ($S_2$) fracture and the second platform in the distance-to-force diagram is reached once the formed segment(s) ($S_1$) fracture. When the further segment ($S_2$) is present in powdery form, however, the "first platform" corresponds to the baseline, i.e. is not visible. Furthermore, depending upon the upper measuring limit of the breaking strength tester, the formed segment(s) ($S_1$) might not have fractured once said upper limit is reached.

In a preferred embodiment, the at least one formed segment ($S_1$) of the pharmaceutical dosage form exhibits a higher breaking strength than the overall pharmaceutical dosage form comprising the formed segment(s) ($S_1$) and the further segment(s) ($S_2$). According to this embodiment, the breaking strength of the pharmaceutical dosage form is preferably defined as the amount of force that is necessary in order to fracture a pharmaceutical dosage form into two or more fragments, wherein said fragments preferably contain the still intact formed segment(s) ($S_1$).

Preferably, the breaking strength of the formed segment(s) ($S_1$) is relatively at least 50 N higher, more preferably at least 100 N higher, still more preferably at least 150 N higher, yet more preferably at least 200 N higher, even more preferably at least 250 N higher, most preferably at least 300 N higher, and in particular at least 350 N higher than the breaking strength of the pharmaceutical dosage form comprising the formed segment(s) ($S_1$) and the further segment(s) ($S_2$).

Another aspect of the invention relates to a process for the production of a pharmaceutical dosage form comprising the steps of
(i) thermoforming at least one formed segment ($S_1$) comprising a first pharmacologically active ingredient ($A_1$) and a natural or synthetic polymer (C);
(ii) providing at least one further segment ($S_2$) comprising a second pharmacologically active ingredient ($A_2$); and
(iii) combining the at least one formed segment ($S_1$), the at least one further segment ($S_2$) and optionally further excipients.

In a preferred embodiment, the formed segment(s) ($S_1$) is/are thermoformed. According to this embodiment, the formed segment(s) ($S_1$) is/are preferably melt-extruded. Further according to this embodiment, the formed segment(s) ($S_1$) is/are preferably monolithic or particulate.

Thermoforming preferably means that in the course of the manufacture of the formed segment(s) ($S_1$) the mass is heated to a temperature above ambient temperature, preferably to at least 30° C., at least 40° C., at least 50° C., at least 60° C., at least 70° C., or at least 80° C., and compressed, preferably at pressures that are sufficient to yield a coherent, not dripping form, preferably at pressures of at least 10 bar or at least 30 bar. The compression force may be exerted prior to, during or subsequent to application of heat.

The formed segment(s) ($S_1$) is/are preferably thermoformed, preferably by melt-extrusion, although also other methods of thermoforming may be useful, such as press-molding at elevated temperature or heating of compacts that were manufactured by conventional compression in a first step and then heated above the softening temperature of the prolonged release matrix material in a second step to form break resistant, hardened compacts, i.e. monolithic formed segment(s) ($S_1$). In this regard, thermoforming preferably means the forming, or molding of a mass after, before or during the application of heat. In a preferred embodiment, thermoforming is performed by hot-melt extrusion.

In a preferred embodiment, hot melt-extrusion is performed by means of a twin-screw-extruder. Melt extrusion preferably provides a melt-extruded strand that is preferably cut into monoliths, which are then optionally compressed and formed. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C.

The strands obtained by way of extrusion can either be subjected to the compression step as such or can be cut prior to the compression step. This cutting can be performed by usual techniques, for example using rotating knives or compressed air, at elevated temperature, e.g. when the extruded stand is still warm due to hot-melt extrusion, or at ambient temperature, i.e. after the extruded strand has been allowed to cool down. When the extruded strand is still warm, singulation of the extruded strand into extruded monoliths and particles, respectively, is preferably performed by cutting the extruded strand immediately after it has exited the extrusion die.

However, when the extruded strand is cut in the cooled state, subsequent singulation of the extruded strand is preferably performed by optionally transporting the still hot extruded strand by means of conveyor belts, allowing it to cool down and to congeal, and subsequently cutting it. Alternatively, the shaping can take place as described in EP-A 240 906 by the extrudate being passed between two counter-rotating calender rolls and being shaped directly to the formed segment ($S_1$). It is of course also possible to subject the extruded strands to the compression step or to the cutting step when still warm, that is more or less immediately after the extrusion step. The extrusion is preferably carried out by means of a twin-screw extruder.

The preferably monolithic or particulate formed segment ($S_1$) according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In general, the process for the production of the preferably monolithic or particulate formed segment ($S_1$), according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the prolonged release matrix material, preferably the natural or synthetic polymer (C), up to its softening point;
(c) hardening the mixture by applying heat and force, it being possible to supply the heat during and/or before and/or after the application of force and the quantity of heat supplied being sufficient to heat the prolonged release matrix material, preferably the natural or synthetic polymer (C), at least up to its softening point; and thereafter allowing the material to cool and removing the force;
(d) optionally singulating the hardened mixture;
(e) optionally shaping the monoliths or particles; and
(f) optionally providing a film coating.

Heat may be supplied directly, e.g. by contact or by means of hot gas such as hot air, or with the assistance of ultrasound; or is indirectly supplied by friction and/or shear. Force may be applied and/or the monoliths or particles may be shaped for example by direct formed segment ($S_1$) forming or with the assistance of a suitable extruder, particularly by means of a screw extruder equipped with one or two screws (single-screw-extruder and twin-screw-extruder, respectively) or by means of a planetary gear extruder.

The final shape of the monoliths and particles, respectively, may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the prolonged release matrix material. However, extrusion at lower temperatures, e.g. ambient temperature, is also possible and may be preferred.

Shaping can be performed, e.g., by means of a forming press comprising die and punches of appropriate shape.

A particularly preferred process for the manufacture of the formed segment(s) ($S_1$) according to the invention involves hot-melt extrusion. In this process, the formed segment(s) ($S_1$) is/are produced by thermoforming with the assistance of an extruder, preferably without there being any observable consequent discoloration of the extrudate.

This process is preferably characterized in that
a) all components are mixed,
b) the resultant mixture is heated in the extruder at least up to the softening point of the prolonged release matrix material and extruded through the outlet orifice of the extruder by application of force,
c) the still plastic extrudate is singulated and formed into the monoliths or particles of the formed segment ($S_1$), or
d) the cooled and optionally reheated singulated extrudate is formed into the monoliths or particles of the formed segment ($S_1$), respectively.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of prolonged release matrix material is extruded from the extruder through a die with at least one bore.

The hot-melt extrusion process according to the invention requires the use of suitable extruders, preferably screw extruders. Screw extruders which are equipped with two screws (twin-screw-extruders) are particularly preferred.

In a preferred embodiment, extrusion is performed in the absence of water, i.e., no water is added. However, traces of water (e.g., caused by atmospheric humidity) may be present.

In another preferred embodiment, particularly when the prolonged release matrix material is employed in the form of an aqueous dispersion, extrusion is performed in the presence of water and the water is evaporated from the extruded material in the course of the extrusion process, i.e. preferably before the extruded material exits the outlet orifice of the extruder. Therefore a vacuum pump mechanism is used to extract the (evaporated) water from the extruded material. Thus, the extruded strand is preferably water-free, which preferably means that the water content of the extruded strand is preferably at most 10 wt.-%, or at most 7.5 wt.-%, or at most 5.0 wt.-%, or at most 4.0 wt.-%, or at most 3.0 wt.-%, or at most 2.0 wt.-%, more preferably at most 1.7 wt.-%, still more preferably at most 1.5 wt.-%, yet more preferably at most 1.3 wt.-%, even more preferably at most 1.0 wt.-%, most preferably at most 0.7 wt.-%, and in particular at most 0.5 wt.-%. For that purpose, extrusion is preferably performed at a temperature above the boiling point of water under the given conditions; when extrusion is performed under vacuum, the boiling point of water may be substantially below 100° C. However, even if extrusion is performed under vacuum the preferred extrusion temperature is above 100° C.

The extruder preferably comprises at least two temperature zones, with heating of the mixture at least up to the softening point of the prolonged release matrix material proceeding in the first zone, which is downstream from a feed zone and optionally mixing zone. The throughput of the mixture is preferably from 1.0 kg to 15 kg/hour. In a preferred embodiment, the throughput is from 0.2 kg/hour to 3.5 kg/hour. In another preferred embodiment, the throughput is from 4 to 15 kg/hour.

In a preferred embodiment, the die head pressure is within the range of from 0.5 to 200 bar. The die head pressure can be adjusted inter alia by die geometry, temperature profile, extrusion speed, number of bores in the dies, screw configuration, first feeding steps in the extruder, and the like.

In a preferred embodiment, the die head pressure is within the range of from 20±19 bar, more preferably 20±15 bar, and in particular 20±10 bar; or the die head pressure is within the range of from 30±20 bar, more preferably 30±15 bar, and in particular 30±10 bar; or the die head pressure is within the range of from 40±20 bar, more preferably 40±15 bar, and in particular 40±10 bar; or the die head pressure is within the range of from 50±20 bar, more preferably 50±15 bar, and in particular 50±10 bar; or the die head pressure is within the range of from 60±20 bar, more preferably 60±15 bar, and in particular 60±10 bar; or the die head pressure is within the range of from 70±20 bar, more preferably 70±15 bar, and in particular 70±10 bar; or the die head pressure is within the range of from 80±20 bar, more preferably 80±15 bar, and in particular 80±10 bar; or the die head pressure is within the range of from 90±20 bar, more preferably 90±15 bar, and in particular 90±10 bar; or the die head pressure is within the range of from 100±20 bar, more preferably 100±15 bar, and in particular 100±10 bar.

The die geometry or the geometry of the bores is freely selectable. The die or the bores may accordingly exhibit a flat (film), round, oblong or oval cross-section, wherein the round cross-section preferably has a diameter of 0.1 mm to 2 mm for extruded particles and a larger diameter for extruded monolithic pharmaceutical dosage forms. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the prolonged release matrix material and does not rise above a temperature at which the pharmacologically active ingredient to be processed may be damaged. Preferably, the temperature of the mixture to be extruded is adjusted to below 180° C., preferably below 150° C., but at least to the softening temperature of prolonged release matrix material. Typical extrusion temperatures are 120° C. and 150° C.

In a preferred embodiment, the extruder torque is within the range of from 30 to 95%. Extruder torque can be adjusted inter alia by die geometry, temperature profile, extrusion speed, number of bores in the dies, screw configuration, first feeding steps in the extruder, and the like.

After extrusion of the molten mixture and optional cooling of the extruded strand or extruded strands, the extrudates are preferably singulated. This singulation may preferably be performed by cutting up the extrudates by means of revolving or rotating knives, wires, blades or with the assistance of laser cutters.

Preferably, intermediate or final storage of the optionally singulated extrudate or the final shape of the monoliths or particles of the formed segment ($S_1$) is performed under oxygen-free atmosphere which may be achieved, e.g., by means of oxygen-scavengers.

The singulated extrudate may be press-formed in order to impart the final shape to the monolithic or particulate formed segment(s) ($S_1$).

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nurnberg, Germany), screw diameters of 18 or 27 mm. Screws having eccentric or blunt ends may be used. A heatable die with a round bore or with a multitude of bores each having a diameter of 0.2, 0.3, 0.4, 0.5, 0.6, 0.7, 0.8, 0.9, 1.0, 2.0, 3.0, 4.0, 5.0 or 0.6 mm may be used. The extrusion parameters may be adjusted e.g. to the following values: rotational speed of the screws: 120 Upm; delivery rate 2 kg/h for a ZSE 18 or 8 kg/h for a ZSE27; product temperature: in front of die 125° C. and behind die 135° C.; and jacket temperature: 110° C. Another suitable extruder that is equipped with a vacuum pump is a Thermo Scientific* Pharma 16 HME hot melt twin-screw extruder.

Preferably, extrusion is performed by means of twin-screw-extruders or planetary-gear-extruders, twin-screw extruders (co-rotating or contra-rotating) being particularly preferred.

The preferably monolithic or particulate formed segment(s) ($S_1$) according to the invention is preferably produced by thermoforming with the assistance of an extruder without any observable consequent discoloration of the extrudates.

The process for the preparation of the preferably monolithic or particulate formed segment ($S_1$) according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the formed segment(s) ($S_1$) is/are monolithic or particulate, preferably oligoparticular or multiparticulate, and the monolith or particles according to the invention can be regarded as "extruded pellet(s)". The term "extruded pellets" has structural implications which are understood by persons skilled in the art. A person skilled in the art knows that pelletized segments or pharmaceutical dosage forms can be prepared by a number of techniques, including:
drug layering on nonpareil sugar or microcrystalline cellulose beads,
spray drying,
spray congealing,
rotogranulation,
hot-melt extrusion,
spheronization of low melting materials, or
extrusion-spheronization of a wet mass.

Accordingly, "extruded pellets" can be obtained either by hot-melt extrusion or by extrusion-spheronization.

"Extruded pellets" can be distinguished from other types of pellets because they are structurally different. For example, drug layering on nonpareils yields multilayered pellets having a core, whereas extrusion typically yields a monolithic mass comprising a homogeneous mixture of all ingredients. Similarly, spray drying and spray congealing typically yield spheres, whereas extrusion typically yields cylindrical extrudates which can be subsequently spheronized.

The structural differences between "extruded pellets" and "agglomerated pellets" are significant because they may affect the release of active substances from the pellets and consequently result in different pharmacological profiles. Therefore, a person skilled in the pharmaceutical formulation art would not consider "extruded pellets" to be equivalent to "agglomerated pellets".

The pharmaceutical dosage forms according to the invention may be prepared from the formed segment(s) ($S_1$) and the further segment(s) ($S_2$) by any conventional method.

When the pharmaceutical dosage forms are prepared by compression, the particles or monoliths of the formed segment(s) ($S_1$), are preferably mixed, e.g. blended and/or granulated (e.g. wet granulated), with the material of the further segment(s) ($S_2$) as outer matrix material and the resulting mix (e.g. blend or granulate) is then either filled in capsules or compressed, preferably in molds, to form pharmaceutical dosage forms. It is also envisaged that the monoliths or particles herein described may be incorporated into a matrix using other processes, such as by melt granulation (e.g. using fatty alcohols and/or water-soluble waxes and/or water-insoluble waxes) or high shear granulation, followed by compression.

When the pharmaceutical dosage forms according to the invention are manufactured by means of an eccentric press, the compression force is preferably within the range of from 5 to 15 kN. When the pharmaceutical dosage forms according to the invention are manufactured by means of a rotating press, the compression force is preferably within the range of from 5 to 40 kN, in certain embodiments >25 kN, in other embodiments about 13 kN.

Another aspect of the invention relates to a pharmaceutical dosage for that is obtainable by any of the methods described above.

Examples of pharmaceutical dosage forms according to the invention include, but are not limited to, capsules, tablets, pills, granules, pellets, films, sachets and effervescent, powders, and the like.

In a preferred embodiment, the pharmaceutical dosage form is selected from the group consisting of capsules, sugar-coated tablets, dry-coated tablets, mantle tablets, and layered tablets.

In a particularly preferred embodiment of the invention, the composition is formulated in a capsule. In accordance with this embodiment, the pharmaceutical dosage form comprises a hard or soft gelatin capsule.

Most pharmaceutical dosage forms are intended to be swallowed whole and accordingly, preferred pharmaceutical dosage forms according to the invention are designed for oral administration.

In a preferred embodiment, the pharmaceutical dosage form is to be administered orally.

Particularly preferably, the pharmaceutical dosage form is to be administered as a whole. This preferably means that the dosage form is neither intended to be chewed on nor to be sucked on prior to being swallowed. Further, the dosage forms are preferably not intended to adhere to the oral mucosa. It is preferably not possible to completely crush or comminute the dosage form by chewing because of the high breaking strength of the segment(s) ($S_1$). Thus, preferably the dosage form according to the invention is swallowed as a whole, i.e. in one piece.

However, alternatively pharmaceutical dosage forms may be dissolved in the mouth, chewed, and some may be placed in a body cavity. Thus, the pharmaceutical dosage form according to the invention may alternatively be adapted for buccal, lingual, rectal or vaginal administration. Implants are also possible.

The pharmaceutical dosage form according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g. In a preferred embodiment, the total weight of the pharmaceutical dosage form is within the range of 600±450 mg, more preferably 600±300 mg, still more preferably 600±200 mg, yet more preferably 600±150 mg, most preferably 600±100 mg, and in particular 600±50 mg.

In a preferred embodiment, the pharmaceutical dosage form according to the invention is a capsule, more preferably a hard capsule and most preferably a hard gelatin capsule. Pharmaceutical dosage forms of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the pharmaceutical dosage form according to the invention is a round pharmaceutical dosage form. Pharmaceutical dosage forms of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In still another preferred embodiment, the pharmaceutical dosage form according to the invention is an oblong pharmaceutical dosage form. Pharmaceutical dosage forms of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

Preferably, the pharmaceutical dosage form according to the invention is not in form of a film.

The pharmaceutical dosage form according to the invention may optionally comprise a coating, e.g. a cosmetic coating. In a preferred embodiment, the coated pharmaceutical dosage form according to the invention is monolithic. The coating is preferably applied after formation of the pharmaceutical dosage form. The coating may be applied prior to or after the curing process. The pharmaceutical dosage forms according to the invention are preferably film coated with conventional film coating compositions. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), poly(meth)-acrylates, such as aminoalkylmethacrylate copolymers, methacrylic acid methylmethacrylate copolymers, methacrylic acid methylmethacrylate copolymers; vinyl polymers, such as polyvinylpyrrolidone, polyvinyl alcohol, polyvinylacetate; and natural film formers.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5.

The coating can also be applied e.g. to improve the aesthetic impression and/or the taste of the pharmaceutical dosage forms and the ease with which they can be swallowed. Coating the pharmaceutical dosage forms according to the invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Coated pharmaceutical dosage forms according to the invention are preferably prepared by first making the cores and subsequently coating said cores using conventional techniques, such as coating in a coating pan.

Preferably, the coating does not contain the second pharmacologically active ingredient ($A_2$), more preferably the coating does not contain any pharmacologically active ingredient.

Apart from the formed segment(s) ($S_1$) and the further segment(s) ($S_2$), the pharmaceutical dosage form may optionally further comprise conventional pharmaceutical excipients.

Preferred pharmaceutical excipients are those which may also be contained in the further segment ($S_2$) and have already been disclosed above, in particular fillers/binders, lubricants, diluents, granulating aids, colorants, flavourants, glidants, wet-regulating agents and disintegrants.

The skilled person will readily be able to determine appropriate quantities of each of these excipients.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen and ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredients, preferably no antagonists against psychotropic substances, in particular no antagonists against opioids. Antagonists suitable for a given pharmacologically active ingredient are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen and ihre Inhaltsstoffe" by Prof. Dr. Hildebert Wagner, 2nd, revised edition, Gustav Fischer Verlag, Stuttgart, New York, 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredients, nor emetics, nor bitter substances.

Preferably, the formed segment(s) ($S_1$), more preferably the entire pharmaceutical dosage form according to the invention contains more than 20 wt.-%, more preferably more than 30 wt.-%, still more preferably more than 40 wt.-%, yet more preferably more than 50 wt.-%, most preferably more than 60 wt.-%, and in particular more than 70 wt.-% of compounds which are not or hardly soluble in ethanol with respect to the total weight of the pharmaceutical dosage form.

For the purpose of specification, compounds which are not or hardly soluble in ethanol have a maximum solubility in aqueous ethanol (96%) at room temperature of preferably less than 1000 mg/L, more preferably less than 800 mg/L, even more preferably less than 500 mg/L, most preferably less than 100 mg/L and in particular less than 10 mg/L or less than 1 mg/L.

Preferably, the formed segment ($S_1$), more preferably the entire pharmaceutical dosage form according to the invention contains more than 50 wt.-%, more preferably more than 60 wt.-%, still more preferably more than 70 wt.-%, yet more preferably more than 80 wt.-%, most preferably more than 90 wt.-%, and in particular more than 95 wt.-% of polymers which are not or hardly soluble in ethanol with respect to the overall amount of polymers contained in the pharmaceutical dosage form.

Preferred polymers which are not or hardly soluble in ethanol according to the invention are xanthan, guar gum and some types of HPMC. The skilled person knows what types of HPMC are not or hardly soluble in ethanol within the sense of the invention.

In a particularly preferred embodiment, formed segment ($S_1$), more preferably the entire pharmaceutical dosage form according to the invention contains polymers which are not or hardly soluble in ethanol and polymers which are soluble in ethanol, wherein the amount of polymers which are not or hardly soluble in ethanol relative to the total amount of polymers contained in the dosage form is 30 to 100 wt.-%, more preferably 50 to 100 wt.-%, still more preferably 60 to 95 wt.-% or 100 wt.-%, yet more preferably 70 to 90 wt.-% or 100 wt.-%, most preferably 80 to 90 wt.-% or 90 to 100 wt.-%, and in particular more than 95 wt.-% or more than 99 wt.-%.

In a preferred embodiment, the pharmaceutical dosage form according to the invention is adapted for administration once daily, preferably orally. In another preferred embodiment, the pharmaceutical dosage form according to the invention is adapted for administration twice daily, preferably orally. In still another preferred embodiment, the pharmaceutical dosage form according to the invention is adapted for administration thrice daily, preferably orally. In yet another preferred embodiment, the pharmaceutical dosage form according to the invention is adapted for administration more frequently than thrice daily, for example 4 times daily, 5 times daily, 6 times daily, 7 times daily or 8 times daily, in each case preferably orally.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

In preferred embodiments, the pharmaceutical dosage form according to the invention is a tablet, preferably selected from the group consisting of bilayer tablets, mantle tablets, trilayer tablets, multilayer tablets (preferably having more than three layers), multicomponent tablets, and sugar coated tablets (dragées). As all these embodiments relate to tablets, the formed segment(s) ($S_1$) and further segment(s) ($S_2$) form a coherent compacted mass so that the overall tablet constitutes a single unit of matter that can be administered to a patient. In particular, the further segment(s) ($S_2$) contained in the tablets is/are not present in form of a powdery material. The total weight of the tablets is not particularly limited. Typically, it is within the range of from 50 mg to 1250 mg. The number of formed segment(s) ($S_1$) and further segment(s) ($S_2$) that are contained in the tablets according to the invention is not particularly limited. Typically, the tablets according to the invention contain 1, 2, or 3, but not more formed segments ($S_1$), as well as 1, 2, or 3, but not more further segments ($S_2$). All preferred embodiments that have been generally defined above fully apply to the preferred tablets according to the invention and are therefore not reiterated. Nevertheless, particularly preferred embodiments of tablets according to the invention will be described in further detail hereinafter.

Preferably,
(a) the tablet is configured for oral administration once daily, twice daily or thrice daily; and/or
(b) the formed segment(s) ($S_1$) contain(s) as first pharmacologically active ingredient ($A_1$) an opioid, preferably selected from the group consisting of oxycodone, oxymorphone, hydromorphone, hydrocodone, morphine, tapentadol, tramadol, buprenorphine, and the physiologically acceptable salts thereof; and/or
(c) the formed segment(s) ($S_1$) contain(s) a release matrix material in which the first pharmacologically active ingredient ($A_1$) is embedded such that prolonged release thereof is achieved; and/or
(d) the formed segment(s) ($S_1$) contain(s) a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;
(e) the formed segment(s) ($S_1$) contain(s) a release matrix material comprising a polymer (C), wherein the content of said polymer (C) is preferably at least 20 wt.-%, at least 25 wt.-% or at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of the single formed segment ($S_1$); and/or
(f) the further segment(s) ($S_2$) contain(s) as second pharmacologically active ingredient ($A_2$) an analgesic, preferably selected from the group consisting of ibuprofen, diclofenac, paracetamol, acetylsalicylic acid and the physiologically acceptable salts thereof; and/or
(g) the first pharmacologically active ingredient ($A_1$) is hydrocodone or a physiologically acceptable salt thereof and the second pharmacologically active ingredient ($A_2$) is paracetamol; and/or
(h) the tablet is to be administered as a whole.

In the above definition, the features (a), (b), (c) . . . (h) are linked with "and/or". For the purpose of specification, this means that the tablet according to the invention preferably realizes all of said features (a), (b), (c) . . . (h) or merely a subgroup of said features (a), (b), (c) . . . (h). Preferred tablets according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e) and (f); or at least features (a), (b), (c), (d), (e), (f) and (g).

Preferably, the pharmaceutical dosage form according to the invention is a bilayer tablet. In the bilayer tablet according to the invention, a single formed segment ($S_1$) and a single further segment ($S_2$) are arranged to form a bilayer tablet (cf. FIG. 1A). Optionally, the bilayer tablet can be sugar coated (dragée).

Preferably,
(a) the bilayer tablet is configured for oral administration once daily, twice daily or thrice daily; and/or
(b) the total weight of the single formed segment ($S_1$) that forms one layer of the bilayer tablet is within the range of 210±200 mg (i.e. 10 mg to 410 mg), more preferably 210±180 mg, still more preferably 210±160 mg, yet more preferably 210±140 mg, even more preferably 210±120 mg, most preferably 210±100 mg, and in particular 210±80 mg; and/or
(c) the single formed segment ($S_1$) contains as first pharmacologically active ingredient ($A_1$) an opioid, preferably selected from the group consisting of oxycodone, oxymorphone, hydromorphone, hydrocodone, morphine, tapentadol, tramadol, buprenorphine, and the physiologically acceptable salts thereof; and/or
(d) the single formed segment ($S_1$) contains a release matrix material in which the first pharmacologically active ingredient ($A_1$) is embedded such that prolonged release thereof is achieved; and/or
(e) the single formed segment ($S_1$) contains a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;
(f) the single formed segment ($S_1$) contains a release matrix material comprising a polymer (C), wherein the content of said polymer (C) is preferably at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of the single formed segment ($S_1$); and/or
(g) the total weight of the single further segment ($S_2$) that forms another layer of the bilayer tablet is within the range of 485±450 mg (i.e. 35 mg to 935 mg), more preferably 485±300 mg, still more preferably 485±250 mg, yet more preferably 485±200 mg, even more preferably 485±150 mg, most preferably 485±75 mg, and in particular 485±35 mg; and/or
(h) the single further segment ($S_2$) contains as second pharmacologically active ingredient ($A_2$) an analgesic, preferably selected from the group consisting of ibuprofen, diclofenac, paracetamol, acetylsalicylic acid and the physiologically acceptable salts thereof; and/or
(i) the single further segment ($S_2$) contains a filler, preferably microcrystalline cellulose; wherein the content of said filler is preferably 30±25 wt.-%, more preferably 30±20 wt.-%, still more preferably 30±15 wt.-%, yet more preferably 30±13 wt.-%, even more preferably 30±10 wt.-%, most preferably 30±7 wt.-%, and in particular 30±5 wt.-%, relative to the total weight of the single further segment ($S_2$); and/or (j) the first pharmacologically active ingredient ($A_1$) is hydrocodone or a physiologically acceptable salt thereof and the second pharmacologically active ingredient ($A_2$) is paracetamol; and/or (k) the bilayer tablet is to be administered as a whole.

In the above definition, the features (a), (b), (c) . . . (k) are linked with "and/or". For the purpose of specification, this means that the bilayer tablet according to the invention preferably realizes all of said features (a), (b), (c) . . . (k) or merely a subgroup of said features (a), (b), (c) . . . (k). Preferred bilayer tablets according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f); or at least features (a), (b), (c), (d), (e), (f), and (g); or at least features (a), (b), (c), (d), (e), (f), (g) and (h); or at least features (a), (b), (c), (d), (e), (f), (g), (h) and (i); or at least features (a), (b), (c), (d), (e), (f), (g), (h), (i) and (j).

Preferably, the pharmaceutical dosage form according to the invention is a mantle tablet. In the mantle tablet according to the invention, a single formed segment ($S_1$) forming a core is surrounded by a single further segment ($S_2$) forming a shell such that formed segment ($S_1$) and further segment ($S_2$) are arranged to form a mantle tablet (cf. FIG. 1B). Optionally, the mantle tablet can be sugar coated (dragée).

Preferably, (a) the mantle tablet is configured for oral administration once daily, twice daily or thrice daily; and/or (b) the total weight of the single formed segment ($S_1$) that forms the core of the mantle tablet is within the range of 210±200 mg (i.e. 10 mg to 410 mg), more preferably 210±180 mg, still more preferably 210±160 mg, yet more preferably 210±140 mg, even more preferably 210±120 mg, most preferably 210±100 mg, and in particular 210±80 mg; and/or (c) the single formed segment ($S_1$) contains as first pharmacologically active ingredient ($A_1$) an opioid, preferably selected from the group consisting of oxycodone, oxymorphone, hydromorphone, hydrocodone, morphine, tapentadol, tramadol, burprenorphine, and the physiologically acceptable salts thereof; and/or (d) the single formed segment ($S_1$) contains a release matrix material in which the first pharmacologically active ingredient ($A_1$) is embedded such that prolonged release thereof is achieved; and/or (e) the single formed segment ($S_1$) contains a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;

(f) the single formed segment ($S_1$) contains a release matrix material comprising a polymer (C), wherein the content of said polymer (C) is preferably at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of the single formed segment ($S_1$); and/or (g) the total weight of the single further segment ($S_2$) that forms the shell of the mantle tablet is within the range of 485±450 mg (i.e. 35 mg to 935 mg), more preferably 485±300 mg, still more preferably 485±250 mg, yet more preferably 485±200 mg, even more preferably 485±150 mg, most preferably 485±75 mg, and in particular 485±35 mg; and/or (h) the single further segment ($S_2$) contains as second pharmacologically active ingredient ($A_2$) an analgesic, preferably selected from the group consisting of ibuprofen, diclofenac, paracetamol, acetylsalicylic acid and the physiologically acceptable salts thereof; and/or (i) the single further segment ($S_2$) contains a filler, preferably microcrystalline cellulose; wherein the content of said filler is preferably 30±25 wt.-%, more preferably 30±20 wt.-%, still more preferably 30±15 wt.-%, yet more preferably 30±13 wt.-%, even more preferably 30±10 wt.-%, most preferably 30±7 wt.-%, and in particular 30±5 wt.-%, relative to the total weight of the single further segment ($S_2$); and/or (j) the first pharmacologically active ingredient ($A_1$) is hydrocodone or a physiologically acceptable salt thereof and the second pharmacologically active ingredient ($A_2$) is paracetamol; and/or (k) the mantle tablet is to be administered as a whole.

In the above definition, the features (a), (b), (c) . . . (k) are linked with "and/or". For the purpose of specification, this means that the mantle tablet according to the invention preferably realizes all of said features (a), (b), (c) . . . (k) or merely a subgroup of said features (a), (b), (c) . . . (k). Preferred mantle tablets according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f); or at least features (a), (b), (c), (d), (e), (f), and (g); or at least features (a), (b), (c), (d), (e), (f), (g) and (h); or at least features (a), (b), (c), (d), (e), (f), (g), (h) and (i); or at least features (a), (b), (c), (d), (e), (f), (g), (h), (i) and (j).

Preferably, the pharmaceutical dosage form according to the invention is a trilayer tablet. In the trilayer tablet according to the invention, a single formed segment ($S_1$) and two further segments ($S_2$) are arranged to form a trilayer tablet, wherein formed segment ($S_1$) forms the middle layer and the two further segments ($S_2$) form the outer layers (cf. FIG. 1C). Preferably, the outer layers of the trilayer tablet formed by said two further segments ($S_2$) have essentially the same composition and total weight. Optionally, the trilayer tablet can be sugar coated (dragée).

Preferably, (a) the trilayer tablet is configured for oral administration once daily, twice daily or thrice daily; and/or (b) the total weight of the single formed segment ($S_1$) that forms the middle layer of the trilayer tablet is within the range of 210±200 mg (i.e. 10 mg to 410 mg), more preferably 210±180 mg, still more preferably 210±160 mg, yet more preferably 210±140 mg, even more preferably 210±120 mg, most preferably 210±100 mg, and in particular 210±80 mg; and/or (c) the single formed segment ($S_1$) contains as first pharmacologically active ingredient ($A_1$) an opioid, preferably selected from the group consisting of oxycodone, oxymorphone, hydromorphone, hydrocodone, morphine, tapentadol, tramadol, buprenorphine, and the physiologically acceptable salts thereof; and/or (d) the single formed segment ($S_1$) contains a release matrix material in which the first pharmacologically active ingredient ($A_1$) is embedded such that prolonged release thereof is achieved; and/or (e) the single formed segment ($S_1$) contains a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;

(f) the single formed segment ($S_1$) contains a release matrix material comprising a polymer (C), wherein the content of said polymer (C) is preferably at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of the single formed segment ($S_1$); and/or (g) the total weight of each of the two further segment ($S_2$) that form the outer layers of the trilayer tablet is within the range of 250±220 mg (i.e. 30 mg to 470 mg), more preferably 250±200 mg, still more preferably 250±175 mg, yet more preferably 250±150 mg, even more preferably 250±100 mg, most preferably 250±75 mg, and in particular 250±35 mg; and/or (h) each of the two further segments ($S_2$) contains as second pharmacologically active ingredient ($A_2$) an analgesic, preferably selected from the group consisting of ibuprofen, diclofenac, paracetamol, acetylsalicylic acid and the physiologically acceptable salts thereof; and/or (i) each of the two further segments ($S_2$) contains a filler, preferably microcrystalline cellulose; wherein the content of said filler is preferably 30±25 wt.-%, more preferably 30±20 wt.-%, still more preferably 30±15 wt.-%, yet more preferably 30±13 wt.-%, even more preferably 30±10 wt.-%, most preferably 30±7 wt.-%, and in particular 30±5 wt.-%, relative to the total weight of one of the two further segments ($S_2$); and/or (j) the first pharmacologically active ingredient ($A_1$) is hydrocodone or a physiologically acceptable salt thereof and the second pharmacologically active ingredient ($A_2$) is paracetamol; and/or (k) the trilayer tablet is to be administered as a whole.

In the above definition, the features (a), (b), (c) . . . (k) are linked with "and/or". For the purpose of specification, this means that the trilayer tablet according to the invention preferably realizes all of said features (a), (b), (c) . . . (k) or merely a subgroup of said features (a), (b), (c) . . . (k). Preferred trilayer tablets according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f); or at least features (a), (b), (c), (d), (e), (f), and (g); or at least features (a), (b), (c), (d), (e), (f), (g) and (h); or at least features (a), (b), (c), (d), (e), (f), (g), (h) and (i); or at least features (a), (b), (c), (d), (e), (f), (g), (h), (i) and (j).

Preferably, the pharmaceutical dosage form according to the invention is a multilayer tablet. In the multilayer tablet according to the invention, a plurality of formed segments ($S_1$) and a plurality of further segments ($S_2$) are arranged to form a multilayer tablet, wherein preferably each of the formed segments ($S_1$) is arranged in between two adjacent further segments ($S_2$). Preferably, the multilayer tablet comprises 4, 5, or 6 layers, but not more. Preferably, the multilayer tablet comprises m layers that are each formed by a formed segment ($S_1$), i.e. m formed segments ($S_1$), and n layers that are each formed by a further segment ($S_2$), i.e. m further segment ($S_2$), wherein m and n are independently integers of 1, 2, 3 or 4, preferably with the proviso that m+n≤6. Optionally, the multilayer tablet can be sugar coated (dragée).

Preferably, (a) the multilayer tablet is configured for oral administration once daily, twice daily or thrice daily; and/or (b) the total weight of each of the m formed segments ($S_1$) that form layers of the multilayer tablet is within the range of 120±90 mg (i.e. 30 mg to 210 mg), more preferably 120±80 mg, still more preferably 120±70 mg, yet more preferably 120±60 mg, even more preferably 120±50 mg, most preferably 120±40 mg, and in particular 120±30 mg; and/or (c) each of the m formed segments ($S_1$) contains as first pharmacologically active ingredient ($A_1$) an opioid, preferably selected from the group consisting of oxycodone, oxymorphone, hydromorphone, hydrocodone, morphine, tapentadol, tramadol, buprenorphine, and the physiologically acceptable salts thereof; and/or (d) each of the m formed segments ($S_1$) contains a release matrix material in which the first pharmacologically active ingredient ($A_1$) is embedded such that prolonged release thereof is achieved; and/or (e) each of the m formed segments ($S_1$) contains a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;

(f) each of the m formed segments ($S_1$) contains a release matrix material comprising a polymer (C), wherein the content of said polymer (C) is preferably at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of one of the m formed segments ($S_1$); and/or (g) the total weight of each of the n further segments ($S_2$) that form layers of the multilayer tablet is within the range of 160±120 mg (i.e. 40 mg to 280 mg), more preferably 160±105 mg, still more preferably 160±80 mg, yet more preferably 160±65 mg, even more preferably 160±50 mg, most preferably 160±35 mg, and in particular 160±20 mg; and/or (h) each of the n further segments ($S_2$) contains as second pharmacologically active ingredient ($A_2$) an analgesic, preferably selected from the group consisting of ibuprofen, diclofenac, paracetamol, acetylsalicylic acid and the physiologically acceptable salts thereof; and/or (i) each of the n further segments ($S_2$) contains a filler, preferably microcrystalline cellulose; wherein the content of said filler is preferably 30±25 wt.-%, more preferably 30±20 wt.-%, still more preferably 30±15 wt.-%, yet more preferably 30±13 wt.-%, even more preferably 30±10 wt.-%, most preferably 30±7 wt.-%, and in particular 30±5 wt.-%, relative to the total weight of one of the n further segments ($S_2$); and/or (j) the first pharmacologically active ingredient ($A_1$) is hydrocodone or a physiologically acceptable salt thereof and the second pharmacologically active ingredient ($A_2$) is paracetamol; and/or (k) the multilayer tablet is to be administered as a whole.

In the above definition, the features (a), (b), (c) . . . (k) are linked with "and/or". For the purpose of specification, this means that the multilayer tablet according to the invention preferably realizes all of said features (a), (b), (c) . . . (k) or merely a subgroup of said features (a), (b), (c) . . . (k). Preferred multilayer tablets according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f); or at least features (a), (b), (c), (d), (e), (f), and (g); or at least features (a), (b), (c), (d), (e), (f), (g) and (h); or at least features (a), (b), (c), (d), (e), (f), (g), (h) and (i); or at least features (a), (b), (c), (d), (e), (f), (g), (h), (i) and (j).

Preferably, the pharmaceutical dosage form according to the invention is a multicomponent tablet. In the multicomponent tablet according to the invention, a plurality of formed segments ($S_1$) form a discontinuous phase embedded in a single further segment ($S_2$) which forms a matrix (cf. FIG. 1D). Preferably, the multicomponent tablet comprises m formed segments ($S_1$) and a single further segment ($S_2$) forming a matrix in which the m formed segments ($S_1$) are embedded, wherein m is an integer of 2, 3, 4, 5 or 6; preferably 2 or 3. Optionally, the multicomponent tablet can be sugar coated (dragée).

Preferably,
(a) the multicomponent tablet is configured for oral administration once daily, twice daily or thrice daily; and/or
(b) the total weight of each of the m formed segments ($S_1$) that form layers of the multilayer tablet is within the range of 120±90 mg (i.e. 30 mg to 210 mg), more preferably 120±80 mg, still more preferably 120±70 mg, yet more preferably 120±60 mg, even more preferably 120±50 mg, most preferably 120±40 mg, and in particular 120±30 mg; and/or
(c) each of the m formed segments ($S_1$) contains as first pharmacologically active ingredient ($A_1$) an opioid, preferably selected from the group consisting of oxycodone, oxymorphone, hydromorphone, hydrocodone, morphine, tapentadol, tramadol, buprenorphine, and the physiologically acceptable salts thereof; and/or
(d) each of the m formed segments ($S_1$) contains a release matrix material in which the first pharmacologically active ingredient ($A_1$) is embedded such that prolonged release thereof is achieved; and/or
(e) each of the m formed segments ($S_1$) contains a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;
(f) each of the m formed segments ($S_1$) contains a release matrix material comprising a polymer (C), wherein the content of said polymer (C) is preferably at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of one of the m formed segments ($S_1$); and/or
(g) the total weight of the single further segment ($S_2$) that forms a matrix of the multicomponent tablet in which the m formed segments ($S_1$) are embedded is within the range of 485±450 mg (i.e. 35 mg to 935 mg), more preferably 485±300 mg, still more preferably 485±250 mg, yet more preferably 485±200 mg, even more preferably 485±150 mg, most preferably 485±75 mg, and in particular 485±35 mg; and/or
(h) the single further segment ($S_2$) contains as second pharmacologically active ingredient ($A_2$) an analgesic, preferably selected from the group consisting of ibuprofen, diclofenac, paracetamol, acetylsalicylic acid and the physiologically acceptable salts thereof; and/or
(i) the single further segment ($S_2$) contains a filler, preferably microcrystalline cellulose; wherein the content of said filler is preferably 30±25 wt.-%, more preferably 30±20 wt.-%, still more preferably 30±15 wt.-%, yet more preferably 30±13 wt.-%, even more preferably 30±10 wt.-%, most preferably 30±7 wt.-%, and in particular 30±5 wt.-%, relative to the total weight of one of the two further segments ($S_2$); and/or
(j) the first pharmacologically active ingredient ($A_1$) is hydrocodone or a physiologically acceptable salt thereof and the second pharmacologically active ingredient ($A_2$) is paracetamol; and/or
(k) the multicomponent tablet is to be administered as a whole.

In the above definition, the features (a), (b), (c) . . . (k) are linked with "and/or". For the purpose of specification, this means that the multicomponent tablet according to the invention preferably realizes all of said features (a), (b), (c) . . . (k) or merely a subgroup of said features (a), (b), (c) . . . (k). Preferred multicomponent tablets according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f); or at least features (a), (b), (c), (d), (e), (f), and (g); or at least features (a), (b), (c), (d), (e), (f), (g) and (h); or at least features (a), (b), (c), (d), (e), (f), (g), (h) and (i); or at least features (a), (b), (c), (d), (e), (f), (g), (h), (i) and (j).

In other preferred embodiments, the pharmaceutical dosage form according to the invention is a capsule, preferably selected from the group consisting of capsules filled with a single formed segment ($S_1$) and a single further segment ($S_2$), capsules filled with a single formed segment ($S_1$) and a plurality of further segments ($S_2$), capsules filled with a plurality of formed segments ($S_1$) and a single further segment ($S_2$), and capsules filled with a plurality of formed segments ($S_1$) and a plurality of further segment ($S_2$). As all these embodiments relate to capsules that are filled with the formed segment(s) ($S_1$) and further segment(s) ($S_2$). While formed segment(s) ($S_1$) typically form(s) a coherent compacted mass, the further segment(s) may either form a coherent compacted mass or may be present in form of a powdery material. The overall capsule constitutes a single unit of matter that can be administered to a patient. The total weight of the capsules is not particularly limited. Typically, it is within the range of from 50 mg to 1250 mg. The number of formed segment(s) ($S_1$) and further segment(s) ($S_2$) that are contained in the capsules according to the invention is not particularly limited. Typically, the capsules according to the invention contain 1, 2, or 3, but not more formed segments ($S_1$), as well as 1, 2, or 3, but not more further segments ($S_2$). All preferred embodiments that have been generally defined above fully apply to the preferred capsules according to the invention and are therefore not reiterated. Nevertheless, particularly preferred embodiments of capsules according to the invention will be described in further detail hereinafter.

Preferably, the pharmaceutical dosage form according to the invention is a capsule filled with formed segment(s) ($S_1$) and further segment(s) ($S_2$). In these capsules according to the invention, the formed segment(s) ($S_1$) is/are preferably present as cut rods and the further segment(s) ($S_2$) is/are preferably present as tablets of such a size that they fit into the interior of the capsule.

Preferably,
(a) the capsule is configured for oral administration once daily, twice daily or thrice daily; and/or (b) the total weight of each of the formed segment(s) ($S_1$) is within the range of 270±210 mg (i.e. 60 mg to 480 mg), more preferably 270±180 mg, still more preferably 270±150 mg, yet more preferably 270±120 mg, even more preferably 270±90 mg, most preferably 270±60 mg, and in particular 270±30 mg; and/or (c) each of the formed segment(s) ($S_1$) contain(s) as first pharmacologically active ingredient ($A_1$) an opioid, preferably selected from the group consisting of oxycodone, oxymorphone, hydromorphone, hydrocodone, morphine, tapentadol, tramadol, buprenorphine, and the physiologically acceptable salts thereof; and/or (d) each of the formed segment(s) ($S_1$) contain(s) a release matrix material in which the first pharmacologically active ingredient ($A_1$) is embedded such that prolonged release thereof is achieved; and/or (e) each of the formed segment(s) ($S_1$) contain(s) a release matrix material comprising a polymer (C) that is preferably selected from the group consisting of polyalkylene oxides, nonionic acrylates, anionic acrylates or cationic acrylates; more preferably a polyethylene oxide having a weight average molecular weight of at least 500,000 g/mol;

(f) each of the formed segment(s) ($S_1$) contain(s) a release matrix material comprising a polymer (C), wherein the content of said polymer (C) is preferably at least 30 wt.-%, still more preferably at least 35 wt.-%, yet more preferably at least 40 wt.-%, even more preferably at least 45 wt.-%, most preferably at least 50 wt.-%, and in particular at least 55 wt.-%, relative to the total weight of one formed segment ($S_1$); and/or (g) the total weight of each of the further segment(s) ($S_2$) is within the range of 360±350 mg (i.e. 10 mg to 710 mg), more preferably 360±300 mg, still more preferably 360±250 mg, yet more preferably 360±200 mg, even more preferably 360±150 mg, most preferably 360±100 mg, and in particular 360±50 mg; and/or (h) each of the further segment(s) ($S_2$) contain(s) as second pharmacologically active ingredient ($A_2$) an analgesic, preferably selected from the group consisting of ibuprofen, diclofenac, paracetamol, acetylsalicylic acid and the physiologically acceptable salts thereof; and/or (i) each of the further segment(s) ($S_2$) contain(s) a filler, preferably pregelled maize starch; wherein the content of said filler is preferably 10±9 wt.-%, more preferably 10±8 wt.-%, still more preferably 10±7 wt.-%, yet more preferably 10±6 wt.-%, even more preferably 10±5 wt.-%, most preferably 10±4 wt.-%, and in particular 10±3 wt.-%, relative to the total weight of one further segment ($S_2$); and/or (j) the first pharmacologically active ingredient ($A_1$) is hydrocodone or a physiologically acceptable salt thereof and the second pharmacologically active ingredient ($A_2$) is paracetamol; and/or (k) the capsule is to be administered as a whole.

In the above definition, the features (a), (b), (c) . . . (k) are linked with "and/or". For the purpose of specification, this means that the capsule according to the invention preferably realizes all of said features (a), (b), (c) . . . (k) or merely a subgroup of said features (a), (b), (c) . . . (k). Preferred capsules according to the invention realize at least feature (a); or at least features (a) and (b); or at least features (a), (b) and (c); or at least features (a), (b), (c) and (d); or at least features (a), (b), (c), (d), and (e); or at least features (a), (b), (c), (d), (e), and (f); or at least features (a), (b), (c), (d), (e), (f), and (g); or at least features (a), (b), (c), (d), (e), (f), (g) and (h); or at least features (a), (b), (c), (d), (e), (f), (g), (h) and (i); or at least features (a), (b), (c), (d), (e), (f), (g), (h), (i) and (j).

The pharmaceutical dosage forms according to the invention may be used in medicine, e.g. as an analgesic. The pharmaceutical dosage forms are therefore particularly suitable for the treatment or management of pain. In such pharmaceutical dosage forms, the pharmacologically active ingredients ($A_1$) and ($A_2$) preferably are analgesically effective. Preferably, the first pharmacologically active ingredient ($A_1$) is hydrocodone or a physiologically acceptable salt thereof and the second pharmacologically active ingredient ($A_2$) is paracetamol.

A further aspect of the invention relates to the pharmaceutical dosage form as described above for use in the treatment of pain.

A further aspect of the invention relates to the use of the first pharmacologically active ingredient ($A_1$) and of the second pharmacologically active ingredient ($A_2$) for the manufacture of a pharmaceutical dosage form as described above for treating pain.

A further aspect of the invention relates to the pharmaceutical dosage form as described above for use in the treatment of pain, wherein the dosage form is swallowed as a whole.

A further aspect of the invention relates to a method of treating pain comprising the administration of the pharmaceutical dosage form as described above to a subject in need thereof.

A further aspect according to the invention relates to the use of a pharmaceutical dosage form as described above for avoiding or hindering the abuse of the first pharmacologically active ingredient ($A_1$) contained therein.

A further aspect according to the invention relates to the use of a pharmaceutical dosage form as described above for avoiding or hindering the unintentional overdose of the first pharmacologically active ingredient ($A_1$) contained therein.

In this regard, the invention also relates to the use of a pharmaceutical dosage form as described above for the prophylaxis and/or the treatment of a disorder, thereby preventing an overdose of the first pharmacologically active ingredient ($A_1$), particularly due to comminution of the pharmaceutical dosage form by mechanical action.

EXAMPLES

The following prophetic and non-prophetic examples further illustrate the invention but are not to be construed as limiting its scope:

Prophetic Examples A1 to A6

Tablets

Example A1

A single formed segment ($S_1$) and a single further segment ($S_2$) that are arranged to form a bilayer tablet (cf. FIG. 1A). Bilayer tablets of the following composition can be prepared:

Formed segment ($S_1$):

| Excipient | A1-$S_1$-1 mg | wt.-% | A1-$S_1$-2 mg | wt.-% | A1-$S_1$-3 mg | wt.-% | A1-$S_1$-4 mg | wt.-% |
|---|---|---|---|---|---|---|---|---|
| Oxycodone HCl | 5.00 | 2.33 | 5.00 | 3.33 | 50.00 | 18.60 | 50.00 | 20.00 |
| Polyethylene Oxide 7,000,000 | 150.51 | 70.00 | 143.50 | 95.67 | 152.65 | 56.80 | 197.50 | 79.00 |
| Hypromellose | 21.50 | 10.00 | — | | 26.88 | 10.00 | — | |
| Polyethylene Glycol | 35.75 | 16.63 | — | | 36.44 | 13.56 | — | |
| Alpha - Tocopherole | 0.43 | 0.20 | — | | 0.54 | 0.20 | — | |
| Citric acid, anhydrous | 1.81 | 0.84 | — | | 2.26 | 0.84 | — | |
| Magnesium stearate | — | | 1.50 | 1.00 | — | | 2.50 | 1.00 |
| Total | 215.00 | 100.00 | 150.00 | 100.00 | 268.77 | 100.00 | 250.00 | 100.00 |

Further segment ($S_2$):

| Excipient | A1-$S_2$-1 mg | wt.-% | A1-$S_2$-2 mg | wt.-% |
|---|---|---|---|---|
| Paracetamol | 325.00 | 64.94 | 325.00 | 69.04 |
| Microcrystalline cellulose | 174.96 | 34.96 | 115.24 | 24.48 |
| Crosscarmellose | — | | 30.03 | 6.38 |
| Magnesium stearate | 0.50 | 0.10 | 0.47 | 0.10 |
| Total | 500.46 | 100.00 | 470.74 | 100.00 |

Example A2

A single formed segment ($S_1$) forming a core that is surrounded by a single further segment ($S_2$) forming a shell such that formed segment ($S_1$) and further segment ($S_2$) are arranged to form a mantle tablet (cf. FIG. 1B). Mantle tablets of the following composition can be prepared:

Formed segment ($S_1$)—core:

| Excipient | A2-$S_1$-1 mg | wt.-% | A2-$S_1$-2 mg | wt.-% | A2-$S_1$-3 mg | wt.-% | A2-$S_1$-4 mg | wt.-% |
|---|---|---|---|---|---|---|---|---|
| Oxycodone HCl | 5.00 | 2.33 | 5.00 | 3.33 | 50.00 | 18.60 | 50.00 | 20.00 |
| Polyethylene Oxide 7.000.000 | 150.51 | 70.00 | 143.50 | 95.67 | 152.65 | 56.80 | 197.50 | 79.00 |
| Hypromellose | 21.50 | 10.00 | — | | 26.88 | 10.00 | — | |
| Polyethylene Glycol | 35.75 | 16.63 | — | | 36.44 | 13.56 | — | |
| Alpha - Tocopherole | 0.43 | 0.20 | — | | 0.54 | 0.20 | — | |
| Citric acid, anhydrous | 1.81 | 0.84 | — | | 2.26 | 0.84 | — | |
| Magnesium stearate | — | | 1.50 | 1.00 | — | | 2.50 | 1.00 |
| Total | 215.00 | 100.00 | 150.00 | 100.00 | 268.77 | 100.00 | 250.00 | 100.00 |

Further segment ($S_2$)—shell:

| Excipient | A2-$S_2$-1 mg | wt.-% | A2-$S_2$-2 mg | wt.-% |
|---|---|---|---|---|
| Paracetamol | 325.00 | 64.94 | 325.00 | 69.04 |
| Microcrystalline cellulose | 174.96 | 34.96 | 115.24 | 24.48 |
| Crosscarmellose | — | | 30.03 | 6.38 |
| Magnesium stearate | 0.50 | 0.10 | 0.47 | 0.10 |
| Total | 500.46 | 100.00 | 470.74 | 100.00 |

Example A3

A single formed segment ($S_1$) and two further segments ($S_2$) that are arranged to form a trilayer tablet, wherein formed segment ($S_1$) forms the middle layer and the two further segments ($S_2$) form the outer layers (cf. FIG. 1C). Trilayer tablets of the following composition can be prepared:

Formed segment (S₁):

|  | A3-S₁-1 | | A3-S₁-2 | | A3-S₁-3 | | A3-S₁-4 | |
| --- | --- | --- | --- | --- | --- | --- | --- | --- |
| Excipient | mg | wt.-% | mg | wt.-% | mg | wt.-% | mg | wt.-% |
| Oxycodone HCl | 5.00 | 2.33 | 5.00 | 3.33 | 50.00 | 18.60 | 50.00 | 20.00 |
| Polyethylene Oxide 7.000.000 | 150.51 | 70.00 | 143.50 | 95.67 | 152.65 | 56.80 | 197.50 | 79.00 |
| Hypromellose | 21.50 | 10.00 | — | — | 26.88 | 10.00 | — | — |
| Polyethylene Glycol | 35.75 | 16.63 | — | — | 36.44 | 13.56 | — | — |
| Alpha - Tocopherole | 0.43 | 0.20 | — | — | 0.54 | 0.20 | — | — |
| Citric acid, anhydrous | 1.81 | 0.84 | — | — | 2.26 | 0.84 | — | — |
| Magnesium stearate | — | — | 1.50 | 1.00 | — | — | 2.50 | 1.00 |
| Total | 215.00 | 100.00 | 150.00 | 100.00 | 268.77 | 100.00 | 250.00 | 100.00 |

Further segments (S₂):

|  | A3-S₂-1 | | A3-S₂-2 | |
| --- | --- | --- | --- | --- |
| Excipient | mg | wt.-% | mg | wt.-% |
| Paracetamol | 162.50 | 64.94 | 162.50 | 69.04 |
| Microcrystalline cellulose | 87.48 | 34.96 | 57.62 | 24.48 |
| Crosscarmellose | — | — | 15.02 | 6.38 |
| Magnesium stearate | 0.25 | 0.10 | 0.24 | 0.10 |
| Total | 250.23 | 100.00 | 235.38 | 100.00 |

Example A4

A plurality of formed segments (S₁) and a plurality of further segments (S₂) that are arranged to form a multilayer tablet, wherein preferably each of the formed segments (S₁) is arranged in between two adjacent further segments (S₂). Multilayer tablets of the following composition can be prepared:

Formed segments (S₁):

|  | A4-S₁-1 | | A4-S₁-2 | | A4-S₁-3 | |
| --- | --- | --- | --- | --- | --- | --- |
| Excipient | mg | wt.-% | mg | wt.-% | mg | wt.-% |
| Oxycodone HCl | 2.50 | 2.33 | 25.00 | 18.60 | 25.00 | 18.60 |
| Polyethylene Oxide 7.000.000 | 75.25 | 70.00 | 76.33 | 56.80 | 72.30 | 53.80 |
| Hypromellose | 10.75 | 10.00 | 13.44 | 10.00 | 13.44 | 10.00 |
| Xanthan-Gum | — | — | — | — | 4.03 | 3.00 |
| Polyethylene Glycol | 17.87 | 16.62 | 18.22 | 13.56 | 18.22 | 13.56 |
| Alpha - Tocopherole | 0.22 | 0.20 | 0.27 | 0.20 | 0.27 | 0.20 |
| Citric acid, anhydrous | 0.91 | 0.85 | 1.13 | 0.84 | 1.13 | 0.84 |
| Total | 107.50 | 100.00 | 134.39 | 100.00 | 134.39 | 100.00 |

Further segments (S₂):

|  | A4-S₂-1 | | A4-S₂-2 | |
| --- | --- | --- | --- | --- |
| Excipient | mg | wt.-% | mg | wt.-% |
| Paracetamol | 108.33 | 64.94 | 108.33 | 69.04 |
| Microcrystalline cellulose | 58.32 | 34.96 | 38.41 | 24.48 |
| Crosscarmellose | — | — | 10.01 | 6.38 |
| Magnesium stearate | 0.16 | 0.10 | 0.16 | 0.10 |
| Total | 166.81 | 100.00 | 156.91 | 100.00 |

Example A5

A plurality of formed segments (S₁) which form a discontinuous phase embedded in further segment (S₂) which forms a matrix (cf. FIG. 1D). Multicomponent tablets of the following composition can be prepared:

Formed segments (S₁):

|  | A5-S₁-1 | | A5-S₁-2 | |
| --- | --- | --- | --- | --- |
| Excipient | mg | wt.-% | mg | wt.-% |
| Oxycodone HCl | 2.50 | 2.33 | 25.00 | 18.60 |
| Polyethylene Oxide 7.000.000 | 75.25 | 70.00 | 76.33 | 56.80 |
| Hypromellose | 10.75 | 10.00 | 13.44 | 10.00 |
| Polyethylene Glycol | 17.87 | 16.62 | 18.22 | 13.56 |
| Alpha-Tocopherole | 0.22 | 0.20 | 0.27 | 0.20 |
| Citric acid, anhydrous | 0.91 | 0.85 | 1.13 | 0.84 |
| Total | 107.50 | 100.00 | 134.39 | 100.00 |

Further segment (S₂):

|  | A5-S₂-1 | | A5-S₂-2 | |
| --- | --- | --- | --- | --- |
| Excipient | mg | wt.-% | mg | wt.-% |
| Paracetamol | 325.00 | 64.94 | 325.00 | 69.04 |
| Microcrystalline cellulose | 174.96 | 34.96 | 115.24 | 24.48 |
| Crosscarmellose | — | — | 30.03 | 6.38 |
| Magnesium stearate | 0.50 | 0.10 | 0.47 | 0.10 |
| Total | 500.46 | 100.00 | 470.74 | 100.00 |

Example A6

A single formed segment ($S_1$) and one or more further segments ($S_2$) that are together coated by a sugar coating thus forming a sugar-coated tablet (dragée). Sugar coated tablets of the compositions according to any of above Examples A1 to A3 can be prepared.

Prophetic Examples B1 to B4

Filled Capsules

Example B1

A single formed segment ($S_1$) and a single further segment ($S_2$) (cf. FIG. 2A). Capsules of the following composition can be prepared:

| Excipient | mg | wt.-% | Segment |
|---|---|---|---|
| Oxycodone HCl | 50.00 | 6.31 | $S_1$ |
| Polyethylene oxide 7.000.000 | 152.65 | 19.28 | |
| Hypromellose 100000 mPa*s Ph.Eur | 26.88 | 3.65 | |
| Macrogol 6000 Ph.Eur. | 36.44 | 4.60 | |
| α-Tocopherol Ph.Eur. | 0.54 | 0.06 | |
| Critic acid anhydrous Ph.Eur. | 2.26 | 0.28 | |
| Paracetamol | 325.00 | 41.05 | $S_2$ |
| Pregelled maize starch | 36.00 | 4.55 | |
| Hard gelatin capsule size 000 | 162.00 | 20.46 | Capsule |
| Total | 791.77 | 100.00 | |

Capsule containing paracetamol and a cut rod comprising oxycodone HCl

Cut rods of 268.77 mg can be produced by weighing the ingredients ($S_1$), sieving (Mesh size 1.0 mm), blending in a Bohle LM 40 MC 20, followed by extrusion using a ZSE 27 Micro PH 40 D (melt temperature 124° C., screw rotation speed 100 rpm, die diameter 5.0 mm, melt pressure ca. 80 bar) equipped with 6 cooling injectors. The extruded strands can be cut with a Combi Cutting unit CC 250.

Tablets of 361.00 mg can be prepared by directly compressing a granulate of the ingredients ($S_2$) by direct compression. The granulate is commercially available as "Paracetamol DC APC 230 F/MS" from manufacturer Atabay/Turkey.

One cut rod and one tablet can be filled in a hard gelatin capsule.

Example B2

A single formed segment ($S_1$) and a plurality of further segments ($S_2$) (cf. FIG. 2B). Capsules of the following composition can be prepared:

| Excipient | mg | wt.-% | Segment |
|---|---|---|---|
| Oxycodone HCl | 50.00 | 6.31 | $S_1$ |
| Polyethylene oxide 7.000.000 | 152.65 | 19.28 | |
| Hypromellose 100000 mPa*s Ph.Eur | 26.88 | 3.65 | |
| Macrogol 6000 Ph.Eur. | 36.44 | 4.60 | |
| α-Tocopherol Ph.Eur. | 0.54 | 0.06 | |
| Critic acid anhydrous Ph.Eur. | 2.26 | 0.28 | |
| Paracetamol | 325.00 | 41.05 | $S_2$ |
| Pregelled maize starch | 36.00 | 4.55 | |
| Hard gelatin capsule size 000 | 162.00 | 20.46 | Capsule |
| Total | 791.77 | 100.00 | |

Capsule containing paracetamol and a cut rod comprising oxycodone HCl

Cut rods of 268.77 mg can be produced by weighing the ingredients ($S_1$), sieving (Mesh size 1.0 mm), blending in a Bohle LM 40 MC 20, followed by extrusion using a ZSE 27 Micro PH 40 D (melt temperature 124° C., screw rotation speed 100 rpm, die diameter 5.0 mm, melt pressure ca. 80 bar) equipped with 6 cooling injectors. The extruded strands can be cut with a Combi Cutting unit CC 250.

Tablets of 180.50 mg can be prepared by directly compressing a granulate of the ingredients ($S_2$) by direct compression. The granulate is commercially available as "Paracetamol DC APC 230 F/MS" from manufacturer Atabay/Turkey.

One cut rod and two tablets can be filled in a hard gelatin capsule.

Example B3

A plurality of formed segments ($S_1$) and a single further segment ($S_2$), which can optionally be present in form of a monolith or in form of a powdery material (cf. FIG. 2F). Capsules of the following composition can be prepared:

| Excipient | mg | wt.-% | Segment |
|---|---|---|---|
| Oxycodone HCl | 50.00 | 6.31 | $S_1$ |
| Polyethylene oxide 7.000.000 | 152.65 | 19.28 | |
| Hypromellose 100000 mPa*s Ph.Eur | 26.88 | 3.65 | |
| Macrogol 6000 Ph.Eur. | 36.44 | 4.60 | |
| α-Tocopherol Ph.Eur. | 0.54 | 0.06 | |
| Critic acid anhydrous Ph.Eur. | 2.26 | 0.28 | |
| Paracetamol | 325.00 | 41.05 | $S_2$ |
| Pregelled maize starch | 36.00 | 4.55 | |
| Hard gelatin capsule size 000 | 162.00 | 20.46 | Capsule |
| Total | 791.77 | 100.00 | |

Capsule containing paracetamol and a cut rod comprising oxycodone HCl

Cut rods of 134.385 mg can be produced by weighing the ingredients ($S_1$), sieving (Mesh size 1.0 mm), blending in a Bohle LM 40 MC 20, followed by extrusion using a ZSE 27 Micro PH 40 D (melt temperature 124° C., screw rotation speed 100 rpm, die diameter 5.0 mm, melt pressure ca. 80 bar) equipped with 6 cooling injectors. The extruded strands can be cut with a Combi Cutting unit CC 250.

Tablets of 361.00 mg can be prepared by directly compressing a granulate of the ingredients ($S_2$) by direct compression. The granulate is commercially available as "Paracetamol DC APC 230 F/MS" from manufacturer Atabay/Turkey.

Two cut rods and one tablet can be filled in a hard gelatin capsule.

Example B4

A plurality of formed segments ($S_1$) and a plurality of further segment ($S_2$) (cf. FIGS. 2C, D and E). Capsules of the following composition can be prepared:

| Excipient | mg | wt.-% | Segment |
|---|---|---|---|
| Oxycodone HCl | 50.00 | 6.31 | $S_1$ |
| Polyethylene oxide 7.000.000 | 152.65 | 19.28 | |
| Hypromellose 100000 mPa*s Ph.Eur | 26.88 | 3.65 | |
| Macrogol 6000 Ph.Eur. | 36.44 | 4.60 | |

-continued

| Excipient | mg | wt.-% | Segment |
|---|---|---|---|
| α-Tocopherol Ph.Eur. | 0.54 | 0.06 | |
| Critic acid anhydrous Ph.Eur. | 2.26 | 0.28 | |
| Paracetamol | 325.00 | 41.05 | $S_2$ |
| Pregelled maize starch | 36.00 | 4.55 | |
| Hard gelatin capsule size 000 | 162.00 | 20.46 | Capsule |
| Total | 791.77 | 100.00 | |

Capsule containing paracetamol and a cut rod comprising oxycodone HCl

Cut rods of 134.385 mg can be produced by weighing the ingredients ($S_1$), sieving (Mesh size 1.0 mm), blending in a Bohle LM 40 MC 20, followed by extrusion using a ZSE 27 Micro PH 40 D (melt temperature 124° C., screw rotation speed 100 rpm, die diameter 5.0 mm, melt pressure ca. 80 bar) equipped with 6 cooling injectors. The extruded strands can be cut with a Combi Cutting unit CC 250.

Tablets of 180.50 mg can be prepared by directly compressing a granulate of the ingredients ($S_2$) by direct compression. The granulate is commercially available as "Paracetamol DC APC 230 F/MS" from manufacturer Atabay/Turkey.

Two cut rods and two tablets can be filled in a hard gelatin capsule.

Non Prophetic Examples

Example 1

Capsule containing paracetamol and a cut rod comprising oxycodone HCl

Cut rods were produced by weighing the ingredients, sieving (Mesh size 1.0 mm), blending in a Bohle LM 40 MC 20, followed by extrusion using a ZSE 27 Micro PH 40 D (melt temperature 124° C., screw rotation speed 100 rpm, die diameter 5.0 mm, melt pressure ca. 80 bar) equipped with 6 cooling injectors. The extruded strands were cut with a Combi Cutting unit CC 250. One cut rod and paracetamol in powder form were filled in a hard gelatin capsule. Composition of capsule containing paracetamol and a cut rod comprising oxycodone HCl:

| Excipient | mg | wt.-% |
|---|---|---|
| Oxycodone HCl | 50.00 | 7.26 |
| Polyethylene oxide 7.000.000 | 152.65 | 22.16 |
| Hypromellose 100000 mPa*s Ph.Eur | 26.88 | 3.90 |
| Macrogol 6000 Ph.Eur. | 36.44 | 5.29 |
| α-Tocopherol Ph.Eur. | 0.54 | 0.08 |
| Critic acid anhydrous Ph.Eur. | 2.26 | 0.33 |
| Paracetamol Ph.Eur. | 325.00 | 47.19 |
| Hard gelatin capsule size 0 | 95.00 | 13.79 |
| Total | 688.77 | 100 |

The capsules were subjected to different tests in order to assess the tamper-resistance with respect to the oxycodone HCl contained in the cut rods.

The hammer test was performed with a weight of 500 g falling from a height of 1000 mm. After the test, the cut rods were still intact.

The breaking strength (resistance to crushing) was measured using a Zwick Z 2.5 materials tester, $F_{max}$=2.5 kN with a maximum draw of 1150 mm. The cut rods displayed a breaking strength of >500 N. FIG. 3 shows the corresponding force distance diagram.

The release profiles of oxycodone HCl from the capsules were determined under in vitro conditions using the basket method according to Ph. Eur. at 75 rpm in 600 mL of 0.1 N HCl, SIF sp (pH 6.8) and 0.1 NHCl+40% ethanol, respectively. The results are summarized in the table here below.

Results of the dissolution tests:

| | dissolution [%] | | |
|---|---|---|---|
| t [min] | in 0.1N HCl | in SIFsp pH 6.8 | in 0.1N HCl + 40% ethanol |
| 60 | 23 | 25 | 16 |
| 120 | 36 | 39 | 26 |
| 480 | 82 | 84 | 65 |
| 600 | 88 | 90 | 73 |
| 720 | 93 | 93 | 78 |

Extraction of oxycodone HCl from the capsule was tested (30 mL, 30 min) in 40% ethanol, water at room temperature and boiling water, respectively. The results are summarized in the below table.

To simulate an addict's attempt at preparing an i.v. injection, a capsule was ground with a commercial coffee mill, type Bosch MKM6000, 180W, Typ KM13 for 2 min followed by extraction in boiled water for 5 min. The results are summarized in the below table.

Results of the extraction test and the i.v. injection preparation:

| | amount of oxycodone HCl [%] |
|---|---|
| intact dosage form | 96.5 |
| extraction in water at room temperature | 0.6 |
| extraction in boiled water | 25.7 |
| extraction in 40% ethanol | 0.9 |
| i.v. injection preparation | 21.9 (n = 2) |

Reference Examples

The following Examples 2-7 are Reference Examples which relate to segments comprising a pharmacologically active ingredient and having a breaking strength of more than 500 N.

Reference Examples 2 to 4 and 6 relate to only one segment and a dosage form comprising said one segment, respectively. Reference Example 5 relates to a dosage form comprising two identical segments having the same breaking strength.

The skilled person is able to combine any of these segments exemplified in the Reference Examples with another segment comprising a pharmacologically active ingredient and having e.g. a lower breaking strength than the segments of the Reference Examples.

Reference Example 2

Cut rods were produced according to the procedure disclosed in Example 1 and having the composition as disclosed in $A_1$-$S_1$-1 with a total weight of each cut rod of 215 mg. The composition is summarized in the table below:

|  | m per capsule [mg] | wt.-% |
|---|---|---|
| Oxycodone HCl | 5.00 | 2.33 |
| Polyethylene oxide 7.000.000 | 150.51 | 70.00 |
| Hypromellose 100000 mPa*s Ph.Eur | 21.50 | 10.00 |
| Macrogol 6000 Ph.Eur. | 35.75 | 16.63 |
| α-Tocopherol Ph.Eur. | 0.43 | 0.20 |
| Critic acid anhydrous Ph.Eur. | 1.81 | 0.84 |
| Total | 215.00 | 100.00 |

The breaking strength (resistance to crushing) was measured using a Sotax HT 100 (DEAC-IN-00705). The cut rods displayed a breaking strength of 1000 N (mean value; n=3, with measured values $b_1=b_2=b_3=1000N$).

FIG. 4 shows the release profiles of one cut rod determined under in vitro conditions (n=3) using the basket method with sinker according to Ph. Eur. at 75 rpm in 600 mL of SGF (pH 1.2) and SGF (pH 1.2)+40% ethanol, respectively.

Reference Example 3

Cut rods were produced according to the procedure disclosed in Example 1 and having the composition as disclosed in $A_1$-$S_1$-1 with the only exception that the total weight of each cut rod was adjusted to 107.5 mg. The composition is summarized in the table below:

|  | m per capsule [mg] | wt.-% |
|---|---|---|
| Oxycodone HCl | 2.50 | 2.33 |
| Polyethylene oxide 7.000.000 | 75.255 | 70.00 |
| Hypromellose 100000 mPa*s Ph.Eur | 10.75 | 10.00 |
| Macrogol 6000 Ph.Eur. | 17.875 | 16.63 |
| α-Tocopherol Ph.Eur. | 0.215 | 0.20 |
| Critic acid anhydrous Ph.Eur. | 0.905 | 0.84 |
| Total | 107.50 | 100.00 |

FIG. 5 shows the release profiles of two cut rods determined under in vitro conditions (n=3) using the basket method with sinker according to Ph. Eur. (one sinker per cut rod) at 75 rpm in 600 mL of SGF (pH 1.2) and SGF (pH 1.2)+40% ethanol, respectively.

Reference Example 4

Capsules comprising one cut rod were produced according to the procedure disclosed in Example 1. One cut rod (215 mg) was filled in a capsule (size 1). The composition of the capsule is summarized in the table below:

|  | m per capsule [mg] | wt.-% |
|---|---|---|
| Oxycodone HCl | 5.00 | 1.72 |
| Polyethylene oxide 7.000.000 | 150.51 | 51.90 |
| Hypromellose 100000 mPa*s Ph.Eur | 21.50 | 7.41 |
| Macrogol 6000 Ph.Eur. | 35.75 | 12.33 |
| α-Tocopherol Ph.Eur. | 0.43 | 0.15 |
| Critic acid anhydrous Ph.Eur. | 1.81 | 0.62 |
| empy capsule size 1 | 75.00 | 25.86 |
| Total | 290.00 | 100.00 |

The breaking strength (resistance to crushing) was measured using a Sotax HT 100 (DEAC-IN-00705). The capsules displayed a breaking strength of 63 N (mean value; n=3*; with measured values $b_1=50$ N; $b_2=76$ N; $b_3=1000$ N*).

*The measured value $b_3$ was not included in the mean value of the breaking strength because it was obtained from an incorrect measurement (the capsule was crushed and the breaking strength of the cut rod was measured instead).

FIG. 6 shows the release profiles of one cut rod in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Reference Example 5

Capsules comprising two cut rods and a lactose tablet were produced according to the procedure disclosed in Example 1. Two cut rods (107.5 mg each) and a lactose tablet (72 mg) as spacer were filled in a capsule (size 1). The composition of the capsule is summarized in the table below:

|  | m per capsule [mg] | wt.-% |
|---|---|---|
| Oxycodone HCl | 5.00 | 1.38 |
| Polyethylene oxide 7.000.000 | 150.51 | 41.58 |
| Hypromellose 100000 mPa*s Ph.Eur | 21.50 | 5.94 |
| Macrogol 6000 Ph.Eur. | 35.75 | 9.88 |
| α-Tocopherol Ph.Eur. | 0.43 | 0.12 |
| Critic acid anhydrous Ph.Eur. | 1.81 | 0.50 |
| empy capsule size 1 | 75.00 | 20.72 |
| Lactose tablet | 72.00 | 19.89 |
| Total | 362.00 | 100.00 |

The breaking strength (resistance to crushing) was measured using a Sotax HT 100 (DEAC-IN-00705). The capsules displayed a breaking strength of 38 N (mean value; n=3*; with measured values $b_1=1000$ N*; $b_2=31$ N; $b_3=45$ N).

*The measured value $b_1$ was not included in the mean value of the breaking strength because it was obtained from an incorrect measurement (the capsule was crushed and the breaking strength of the cut rod was measured instead).

FIG. 7 shows the release profiles of two cut rods and a lactose tablet in a capsule determined under in vitro conditions (n=3) using the basket method with sinker according to Ph. Eur. at 75 rpm in 600 mL of SGF (pH 1.2) and SGF (pH 1.2)+40% ethanol, respectively.

Reference Example 6

Layer-core-tablets (mantle-core-tablets) (9×21 mm, oblong) were produced using one cut rod (215 mg) as the core and an MCC-based mixture as the mantle. The MCC-based mixture was a mixture of microcrystalline cellulose (MCC) with 2 wt.-% maize starch as disintegrant and 1 wt.-% magnesium stearate. The composition of the mantle-core-tablets is summarized in the table below:

|  | m per capsule [mg] | wt.-% |
|---|---|---|
| Oxycodone HCl | 5.00 | 0.61 |
| Polyethylene oxide 7.000.000 | 150.51 | 18.47 |
| Hypromellose 100000 mPa*s Ph.Eur | 21.50 | 2.64 |
| Macrogol 6000 Ph.Eur. | 35.75 | 4.39 |
| α-Tocopherol Ph.Eur. | 0.43 | 0.05 |
| Critic acid anhydrous Ph.Eur. | 1.81 | 0.22 |

-continued

|  | m per capsule [mg] | wt.-% |
|---|---|---|
| MCC | 582.00 | 71.41 |
| Maize starch | 12.00 | 1.47 |
| Magnesium stearate | 6.00 | 0.74 |
| Total | 815.00 | 100.00 |

The breaking strength (resistance to crushing) was measured using a Sotax HT 100 (DEAC-IN-00705). The mantle tablets displayed a breaking strength of 65 N (mean value; n=3; with measured values $b_1$=63 N; $b_2$=58 N; $b_3$=73 N).

FIG. 8 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

Reference Example 7

Layer-core-tablets (mantle-core-tablets) (9×21 mm, oblong) were produced using two cut rods and a lactose tablet (72 mg) as cores and an MCC-based mixture as the mantle. The MCC-based mixture was a mixture of microcrystalline cellulose (MCC) with 2 wt.-% maize starch as disintegrant and 1 wt.-% magnesium stearate. The composition of the mantle-core-tablets is summarized in the table below:

|  | m per capsule [mg] | wt.-% |
|---|---|---|
| Oxycodone HCl | 5.00 | 0.64 |
| Polyethylene oxide 7.000.000 | 150.51 | 19.12 |
| Hypromellose 100000 mPa*s Ph.Eur | 21.50 | 2.73 |
| Macrogol 6000 Ph.Eur. | 35.75 | 4.54 |
| α-Tocopherol Ph.Eur. | 0.43 | 0.05 |
| Critic acid anhydrous Ph.Eur. | 1.81 | 0.23 |
| Lactose tablet | 72.00 | 9.15 |
| MCC | 485.00 | 61.63 |
| Maize starch | 10.00 | 1.27 |
| Magnesium stearate | 5.00 | 0.64 |
| Total | 787.00 | 100.00 |

The breaking strength (resistance to crushing) was measured using a Sotax HT 100 (DEAC-IN-00705). The mantle tablets displayed a breaking strength of 19 N (mean value; n=3; with measured values $b_1$=18 N; $b_2$=21 N; $b_3$=17 N).

FIG. 9 shows the release profiles of a mantle tablet determined under in vitro conditions (n=3) using the basket method with sinker according to Ph. Eur. at 75 rpm in 600 mL of SGF (pH 1.2) and SGF (pH 1.2)+40% ethanol, respectively.

FIGS. 10 to 14

FIGS. 10 to 14 show combinations of the release profiles obtained in Reference Examples 2 to 7.

Figure 10:
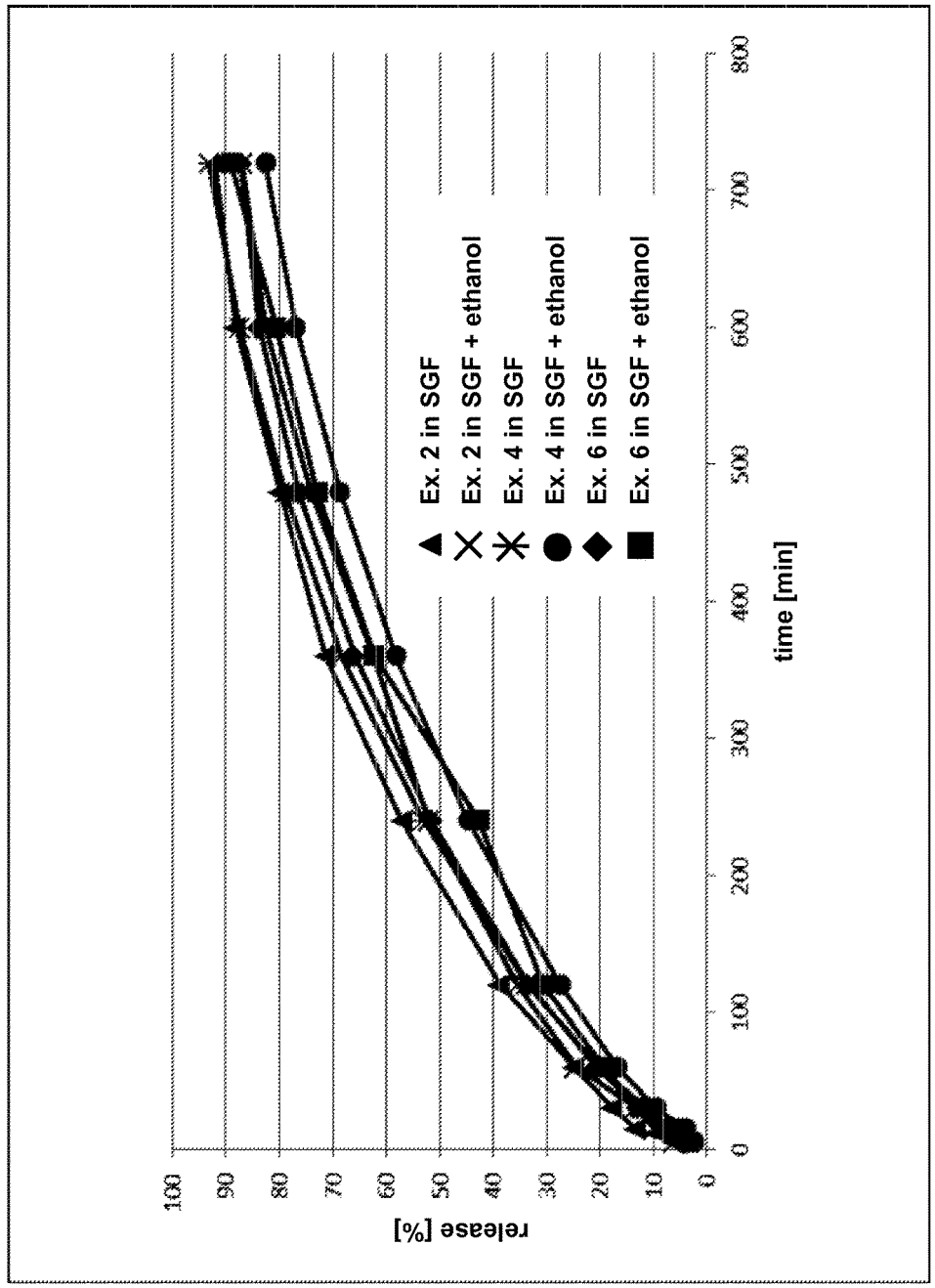

FIG. 10 shows the release profiles of the cut rod (m=215 mg) as such (Reference Example 2, FIG. 4), in a capsule (Reference Example 4, FIG. 6), and in form of a mantle tablet (Reference Example 6, FIG. 8).

Figure 11:
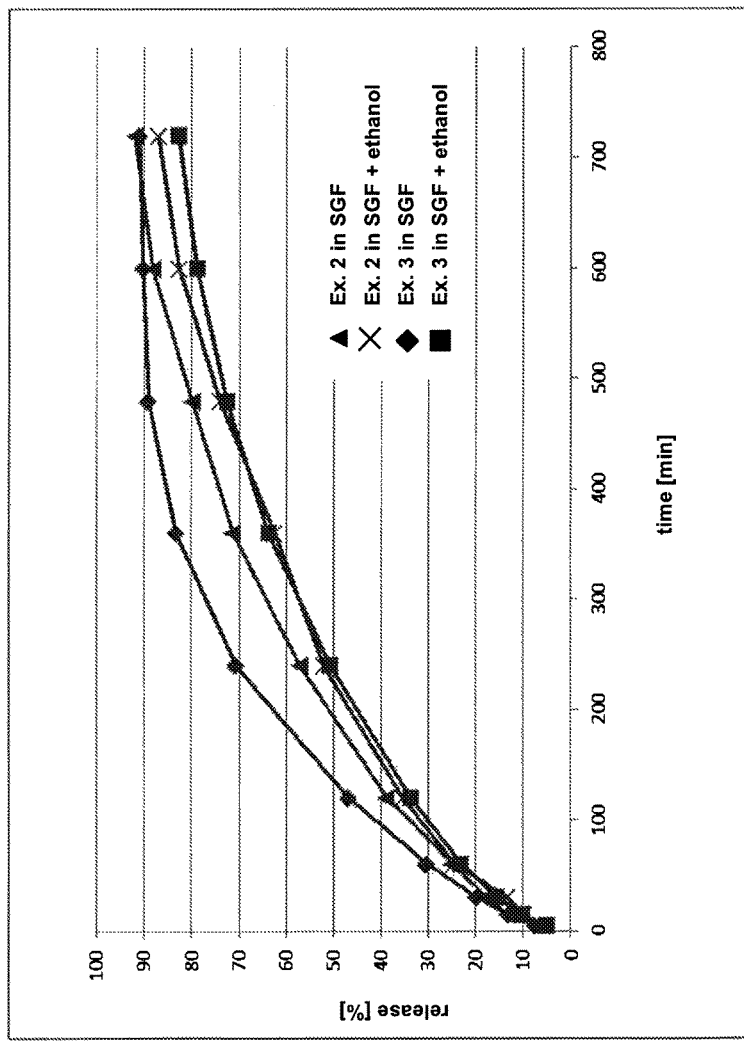

FIG. 11 shows the release profiles of one cut rod (m=215 mg) (Reference Example 2, FIG. 4) and two cut rods (m=107.5 mg) (Reference Example 3, FIG. 5).

Figure 12:
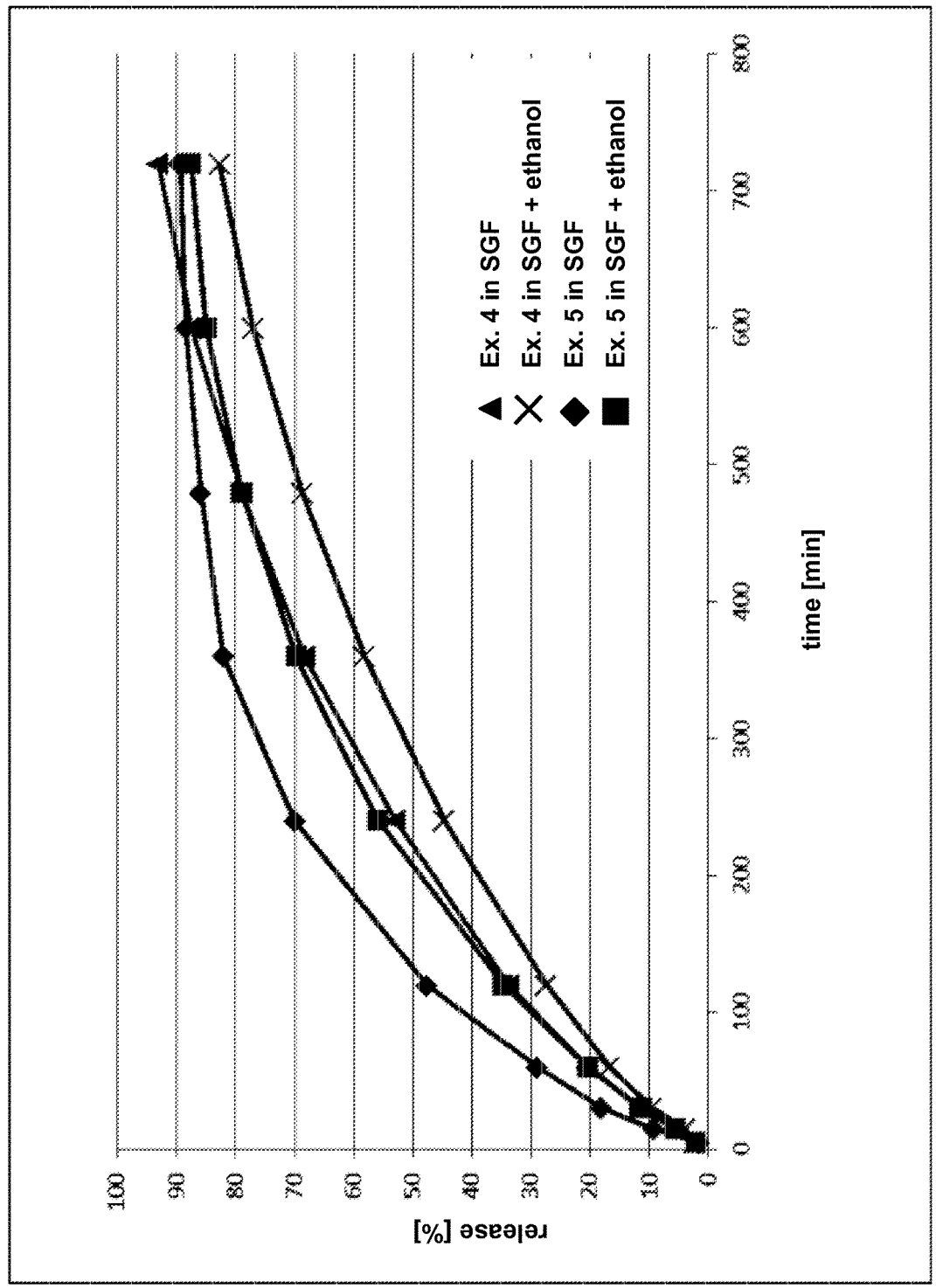

FIG. 12 shows the release profile of a capsule containing one cut rod (Reference Example 4, FIG. 6) and a capsule containing two cut rods (Reference Example 5, FIG. 7).

Figure 13:
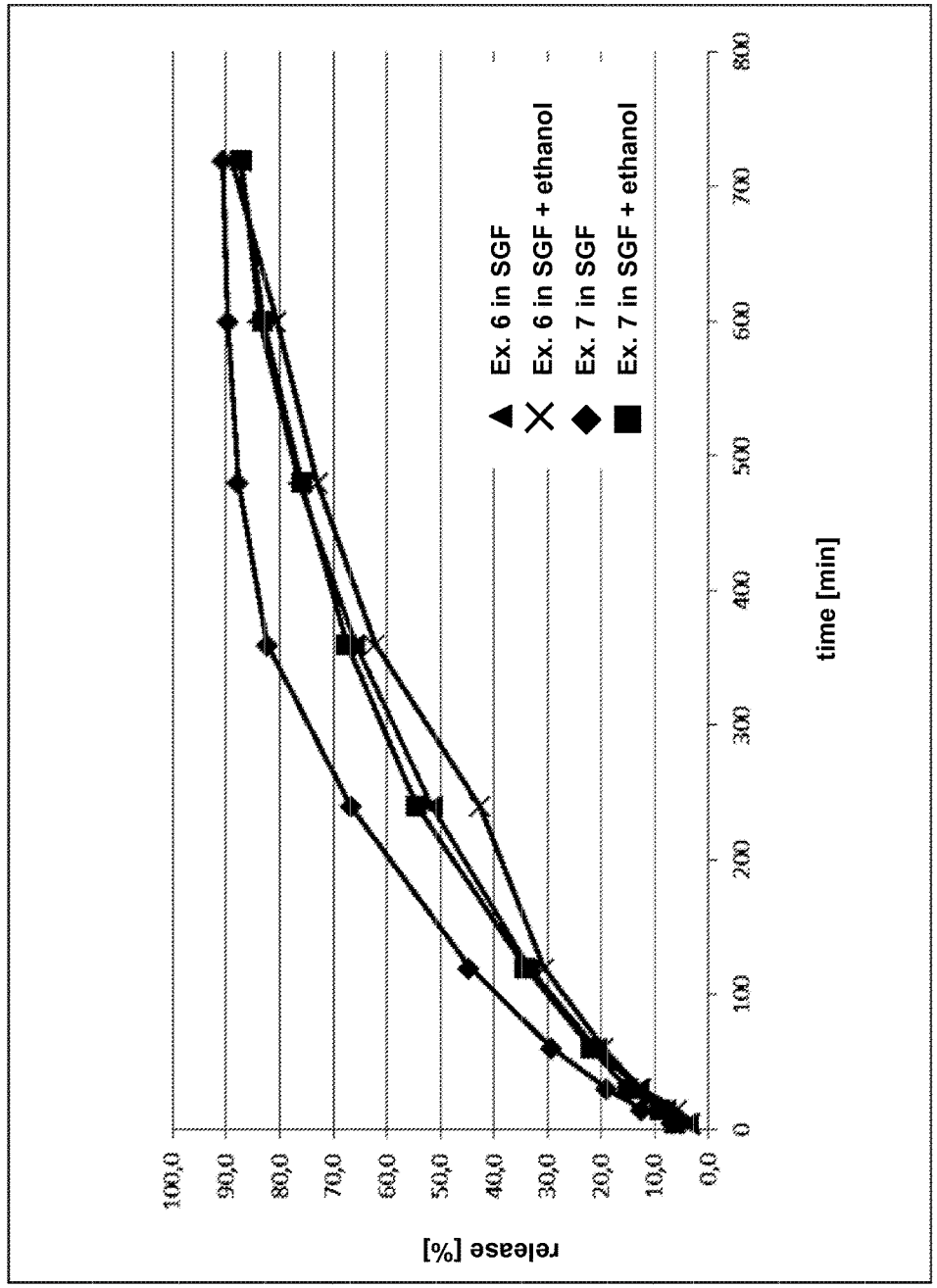

FIG. 13 shows the release profiles of a mantle tablet containing one cut rod (Reference Example 6, FIG. 8) and a mantle tablet containing two cut rods (Reference Example 7, FIG. 9).

Figure 14:
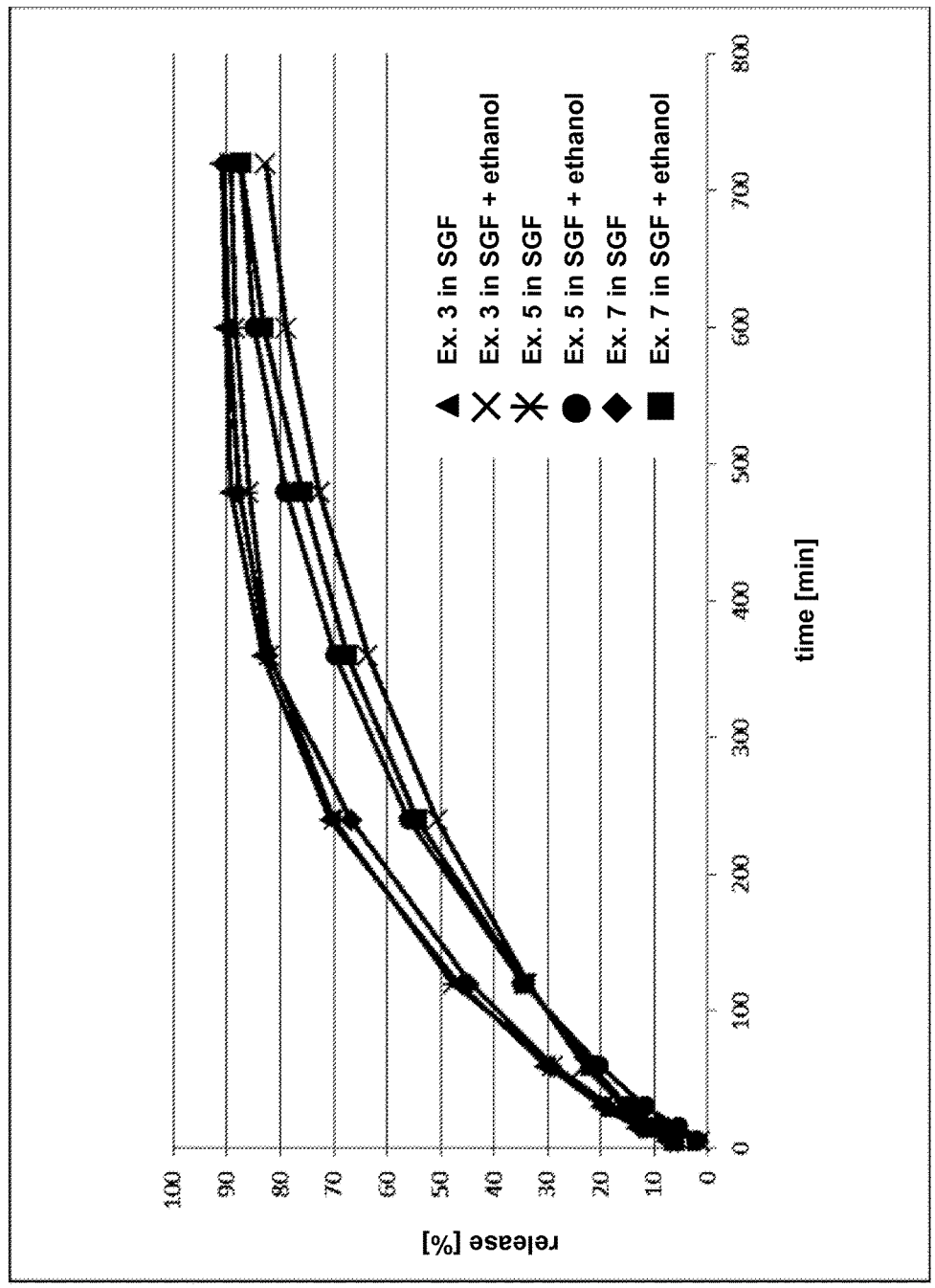

FIG. 14 shows the release profiles of two cut rods (m=107.5 mg) as such (Reference Example 3, FIG. 5), in a capsule (Reference Example 5, FIG. 7), and in form of a mantle tablet (Reference Example 7, FIG. 9).

The invention claimed is:

1. A pharmaceutical dosage form comprising:
   (i) a plurality of formed segments ($S_1$), each of which contains a first pharmacologically active ingredient ($A_1$) and provides prolonged release thereof, said first pharmacologically active ingredient $A_1$ being selected from the group consisting of opioids and physiologically acceptable salts thereof; and
   (ii) a plurality of formed segments ($S_2$), each of which contains a second pharmacologically active ingredient ($A_2$) and provides immediate release thereof, said second pharmacologically active ingredient $A_2$ being selected from the group consisting of non-opioid analgesics and physiologically acceptable salts thereof;
   wherein the plurality of formed segments ($S_1$) and the plurality of further segments ($S_2$) are oligoparticulate, wherein the plurality of formed segments ($S_1$) do not contain any non-opioid analgesics or physiologically acceptable salts thereof, wherein the plurality of further segments ($S_2$) do not contain any opioids or physiologically acceptable salts thereof, wherein the plurality of formed segments ($S_1$) exhibit a higher breaking strength than the plurality of further segments ($S_2$), and wherein the plurality of formed segments ($S_1$) exhibit a breaking strength of more than 500 N.

2. The pharmaceutical dosage form according to claim 1, wherein the plurality of further segments ($S_2$) exhibit a breaking strength of at most 500 N.

3. The pharmaceutical dosage form according to claim 1, wherein the second pharmacologically active ingredient ($A_2$) is selected from the group consisting of acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, phenazone, metamizole sodium, aminophenazone, propyphenazone, nifenazone, paracetamol, phenacetin, bucetin, propacetamol, rimazolium, glafenine, floctafenine, viminol, nefopam, flupirtine, ziconotide, methoxyflurane, nabiximols, dihydroergotamine, ergotamine, methysergide, lisuride, flumedroxone, sumatriptan, naratriptan, zolmitriptan, rizatriptan, almotriptan, eletriptan, frovatriptan, pizotifen, clonidine, iprazochrome, dimetotiazine, oxetorone, phenylbutazone, mofebutazone, oxyphenbutazone, clofezone, kebuzone, indomethacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lornoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, naproxcinod, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, oxycinchophen, sodium aurothiomalate, sodium aurotiosulfate, auranofin, aurothioglucose, aurotioprol, penicillamine and bucillamine.

4. The pharmaceutical dosage form according to claim 1, wherein the first pharmacologically active ingredient ($A_1$) is hydrocodone or a physiologically acceptable salt thereof and the second pharmacologically active ingredient ($A_2$) is paracetamol.

5. The pharmaceutical dosage form according to claim 1, wherein the first pharmacologically active ingredient ($A_1$) is embedded in a prolonged release matrix comprising a synthetic or natural polymer (C).

6. The pharmaceutical dosage form according to claim 5, wherein
   (i) the content of the synthetic or natural polymer (C) is at least 30 wt.-% relative to the total weight of the formed segments ($S_1$); and/or
   (ii) the synthetic or natural polymer (C) is selected from acrylic polymers and polyalkylene oxides.

7. The pharmaceutical dosage form according to claim 1, which under in vitro conditions in 600 mL 0.1 N HCl, using the basket method according to Ph. Eur. at 75 rpm, after 1 h under physiological conditions has released at most 50% of the first pharmacologically active ingredient ($A_1$) relative to the total amount of $A_1$ originally contained in the pharmaceutical dosage form.

8. The pharmaceutical dosage form according to claim 1, which under in vitro conditions in 600 mL 0.1 N HCl, using the basket method according to Ph. Eur. at 75 rpm, after 1 h under physiological conditions has released at least 60% of the second pharmacologically active ingredient ($A_2$) relative to the total amount of the second pharmacologically active ingredient ($A_2$) originally contained in the pharmaceutical dosage form.

9. The pharmaceutical dosage form according to claim 1, wherein the plurality of formed segments ($S_1$) are tamper resistant and provide resistance against grinding and/or resistance against solvent extraction and/or resistance against dose-dumping in aqueous ethanol.

10. The pharmaceutical dosage form according to claim 1, which is selected from the group consisting of capsules, sugar-coated tablets, dry-coated tablets, mantle tablets, and layered tablets.

11. The pharmaceutical dosage form according to claim 1, wherein the plurality of formed segments ($S_1$) are thermoformed.

12. The pharmaceutical dosage form according to claim 1, wherein the formed segments ($S_1$) have an extension in any direction of at least 2.0 mm.

13. The pharmaceutical dosage form according to claim 1, which is to be administered orally.

14. The pharmaceutical dosage form according to claim 1, which is to be administered as a whole.

15. A process for the production of a pharmaceutical dosage form according to claim 1 comprising the steps of:
   (i) thermoforming a plurality of formed segments ($S_1$) comprising a first pharmacologically active ingredient ($A_1$) and a natural or synthetic polymer (C);
   (ii) providing a plurality of further segments ($S_2$) comprising a second pharmacologically active ingredient ($A_2$); and
   (iii) combining the plurality of formed segments ($S_1$), the plurality of further segments ($S_2$) and optionally further excipients.

16. A method of treating pain in a patient in need of such treating, said method comprising orally administering to said patient a pharmaceutical dosage form according to claim 1, wherein the dosage form is swallowed by said patient as a whole.

\* \* \* \* \*